(12) United States Patent
Johnson et al.

(10) Patent No.: US 11,008,626 B2
(45) Date of Patent: May 18, 2021

(54) **COMPOSITIONS AND METHODS FOR DETECTION OF DRUG RESISTANT *MYCOBACTERIUM TUBERCULOSIS***

(71) Applicant: ROCHE MOLECULAR SYSTEMS, INC., Pleasanton, CA (US)

(72) Inventors: Jenny A. Johnson, Castro Valley, CA (US); Rochak Mehta, Union City, CA (US); Andy Yuen, Dublin, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 145 days.

(21) Appl. No.: 16/109,551

(22) Filed: Aug. 22, 2018

(65) Prior Publication Data
US 2018/0355412 A1 Dec. 13, 2018

(51) Int. Cl.
*C12Q 1/68* (2018.01)
*C12Q 1/689* (2018.01)

(52) U.S. Cl.
CPC ....... *C12Q 1/689* (2013.01); *C12Q 2600/156* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | |
|---|---|---|
| 5,643,723 A | 7/1997 | Persing et al. |
| 2010/0261163 A1 | 10/2010 | Zasedatelev et al. |

FOREIGN PATENT DOCUMENTS

| | | |
|---|---|---|
| CN | 102719537 A | 10/2012 |
| CN | 102559916 B | 4/2014 |
| KR | 20090121611 A | 11/2009 |
| WO | 2011140237 A2 | 11/2011 |

OTHER PUBLICATIONS

BIORAD (Real Time PCR Applications guide, 2006, pp. 1-74).*
Didenko (Biotechniques, vol. 31, pp. 1106-1121; 2001).*
Applied Biosystems (Applied Biosystems TaqMan SNP Gentoyping Assays Protocol, 2010).*
Garcia De Viedma D. et al., New Real-Time PCR Able to Detect in a Single Tube Multiple Rifampin Resistance Mutations and High-Level Isoniazid Resistance Mutations in *Mycobacterium tuberculosis*, Journal of Clinical Microbiology, Mar. 1, 2002, p. 988-995, vol. 40, No. 3, American Society for Microbiology.
Goncalves M.G. et al., Fast test for assessing the susceptibility of *Mycobacterium tuberculosis* to isoniazid and rifampin by real-time PCR, Memorias do Instituto Oswaldo Cruz, Rio de Janeiro, Nov. 1, 2012, p. 903-908, vol. 107, No. 7.
International Search Report dated Apr. 25, 2016 in Application No. PCT/EP2015/080484, 4 pages.
Nikolayevsky V. et al., Detection of Mutations Associated with Isoniazid and Rifampin Resistance in *Mycobacterium tuberculosis* Isolates from Samara Region, Russian Federation, Journal of Clinical Microbiology, Oct. 1, 2004, p. 4498-4502, vol. 42, No. 10, American Society for Microbiology.
Ong D.C.T. et al., Rapid Detection of Rifampicin- and Isoniazid-Resistant *Mycobacterium tuberculosis* by High-Resolution Melting Analysis, Journal of Clinical Microbiology, Feb. 17, 2010, p. 1047-1054, vol. 48, No. 4, American Society for Microbiology.
Torres M.J. et al., Use of Real-Time PCR and Fluorimetry for Rapid Detection of Rifampin and Isoniazid Resistance-Associated Mutations in *Mycobacterium tuberculosis*, Journal of Clinical Microbiology, Sep. 1, 2000, p. 3194-3199, vol. 38, No. 9, American Society for Microbiology.
Khosravi et al., Braz. J. Infect. Dis., 2012, 16(1):57-62.
Bostanabad et al., Tanaffos, 2006, 5(1):31-36.
Dantes et al., PLoS One, vol. 7, issue 5, May 2012, pp. 1-5.
Blakemore et al., Journal of Clinical Microbiology, val 48, pp. 2495-2501; 2010.

* cited by examiner

*Primary Examiner* — Jehanne S Sitton
(74) *Attorney, Agent, or Firm* — David J. Chang

(57) ABSTRACT

Methods for the rapid detection of the presence or absence of *Mycobacterium tuberculosis* (MTB) resistant to rifampicin (MTB-RIF) and/or MTB resistant to isoniazid (MTB-INH) in a biological or non-biological sample are described. The methods can include performing an amplifying step, a hybridizing step, and a detecting step. Furthermore, primers, probes targeting the genes for rpoB, inhA, and katG, along with kits are provided that are designed for the detection of MTB-RIF and/or MTB-INH.

5 Claims, 8 Drawing Sheets
Specification includes a Sequence Listing.

TTCGGCCCGGCCGGGCGCCGAGACGATAGGTTGTCGGGGTGACTGCCACAGCCACTGAAGGGGGCCAAACCCCCATTCGTATCCCGTTCAGTCC SEQ ID NO: 425 (continued)

TTCGGCCCGGCCGGGCGCCGAGATGATAGGTTGTCGGGGTGACTGCCACAGCCACTGAAGGGGGCCAAACCCCCATTCGTATCCCGTTCAGTCC SEQ ID NO: 426 (continued)

TTCGGCCCGGCCGGGCGCCGAGACGATAGGTAGTCGGGGTGACTGCCACAGCCACTGAAGGGGGCCAAACCCCCATTCGTATCCCGTTCAGTCC SEQ ID NO: 427 (continued)

TTCGGCCCGGCCGGGCGCCGAGACGATAGGTCGTCGGGGTGACTGCCACAGCCACTGAAGGGGGCCAAACCCCCATTCGTATCCCGTTCAGTCC SEQ ID NO: 428 (continued)

FIG. 3B

SEQUENCE LISTING

```
<160> NUMBER OF SEQ ID NOS: 433

<210> SEQ ID NO 1
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3SP531L09

<400> SEQUENCE: 1
gttggcgctg gggc                                                       14

<210> SEQ ID NO 2
<211> LENGTH: 15
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3SP531L18

<400> SEQUENCE: 2
actgttggcg ctggg                                                  15

<210> SEQ ID NO 3
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3SP531L19

<400> SEQUENCE: 3
ctgttggcgc uggg                                                   14

<210> SEQ ID NO 4
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3S531L18B

<400> SEQUENCE: 4
actgttggcg cuggg                                                  15

<210> SEQ ID NO 5
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3S531L18C

<400> SEQUENCE: 5
ctgtuggcgc uggg                                                   14

<210> SEQ ID NO 6
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
```

<223> OTHER INFORMATION: RMRPO3531L1B

<400> SEQUENCE: 6
ctgttggcgc tggggc                                                16

<210> SEQ ID NO 7
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3SP531L20

<400> SEQUENCE: 7
acugttggcg cugg                                                  14

<210> SEQ ID NO 8
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3S531L20

<400> SEQUENCE: 8
ccgactgttg gcgcu                                                 15

<210> SEQ ID NO 9
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3SP531L22

<400> SEQUENCE: 9
ctgttggcgc uggg                                                  14

<210> SEQ ID NO 10
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3SP531L24

<400> SEQUENCE: 10
cuguuggcgc tggggc                                                16

-continued

```
<210> SEQ ID NO 11
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3SP531L25

<400> SEQUENCE: 11 cguuggcgc tgggg                                                      15

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3SP531L26

<400> SEQUENCE: 12
uguuggcgct ggggccc                                                   17

<210> SEQ ID NO 13
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3S531L20B

<400> SEQUENCE: 13
acuguuggcg cugg                                                      14

<210> SEQ ID NO 14
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3S531L20C

<400> SEQUENCE: 14
acuguuggcg cugg                                                      14

<210> SEQ ID NO 15
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide
<220> FEATURE:
<223> OTHER INFORMATION: RMRPO3S531L20D

<400> SEQUENCE: 15
acugutggcg cugg                                                          14

<210> SEQ ID NO 16
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3S531L25B

<400> SEQUENCE: 16
cuguuggcgc uggg                                                          14

<210> SEQ ID NO 17
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3S531L25C

<400> SEQUENCE: 17
cuguuggcgc uggc                                                          14

<210> SEQ ID NO 18
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3S531L20F

<400> SEQUENCE: 18
acuguuggcg cugcagc                                                       17

<210> SEQ ID NO 19
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3531L20HS

<400> SEQUENCE: 19
```

```
acuguucggc gcugg                                                        15
```

<210> SEQ ID NO 20
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3531L25C2

<400> SEQUENCE: 20

```
cuguuggcgc uggc                                                         14
```

<210> SEQ ID NO 21
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3531L20C2

<400> SEQUENCE: 21

```
acuguuggcg cugc                                                         14
```

<210> SEQ ID NO 22
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3531L25C3

<400> SEQUENCE: 22

```
acuguuggcg cuggc                                                        15
```

<210> SEQ ID NO 23
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3S531F1

<400> SEQUENCE: 23

```
acuguucgcg cugg                                                         14
```

<210> SEQ ID NO 24
<211> LENGTH: 14
<212> TYPE: DNA

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3531L25B2

<400> SEQUENCE: 24 cguuggcgc tggg                                                          14

<210> SEQ ID NO 25
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3531L31

<400> SEQUENCE: 25
uguuggcgct gggg                                                         14

<210> SEQ ID NO 26
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3531L25B3

<400> SEQUENCE: 26 cguuggcgc tggg                                                          14

<210> SEQ ID NO 27
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3531L25B4

<400> SEQUENCE: 27 cguuggcgc tggc                                                          14

<210> SEQ ID NO 28
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3F531L -continued

<400> SEQUENCE: 28
ccaacagtcg gcgcttg                                                    17

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3F531L 02

<400> SEQUENCE: 29
ccaacagtcg gcgcttgtgg gtc                                             23

<210> SEQ ID NO 30
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3F531L 04

<400> SEQUENCE: 30
ccaacagtcg gcgcttg                                                    17

<210> SEQ ID NO 31
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3F531L05

<400> SEQUENCE: 31
ccaacagtcg gcgcttg                                                    17

<210> SEQ ID NO 32
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3F531L06

<400> SEQUENCE: 32
ccaacagucg gcgctug                                                    17

<210> SEQ ID NO 33
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3AP531L11

<400> SEQUENCE: 33

```
ccaacagtcg gcgcttg                                                    17

<210> SEQ ID NO 34
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3AP531L12

<400> SEQUENCE: 34
ccaacagtcg gcgcttg                                                    17

<210> SEQ ID NO 35
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3AP531L13

<400> SEQUENCE: 35
ccaacagtcg gcgcttg                                                    17

<210> SEQ ID NO 36
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3AP531L14

<400> SEQUENCE: 36
ccaacagtcg gcgcttg                                                    17

<210> SEQ ID NO 37
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3A531L12B

<400> SEQUENCE: 37
ccaacagucg gcgcttg                                                    17

<210> SEQ ID NO 38
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3AP531L17

<400> SEQUENCE: 38
```
ccaacagtcg gcgc                                                    14

<210> SEQ ID NO 39
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3A531L17B

<400> SEQUENCE: 39
ccaacagtcg gcgc                                                    14

<210> SEQ ID NO 40
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3A531L19

<400> SEQUENCE: 40
ccaacagtcg gcgct                                                   15

<210> SEQ ID NO 41
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3A531L20

<400> SEQUENCE: 41
ccaacagtcg gcgct                                                   15

<210> SEQ ID NO 42
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3A531L18D

<400> SEQUENCE: 42
ccaacagucg gcgct                                                   15

<210> SEQ ID NO 43
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3A531L12C

```
<400> SEQUENCE: 43
ccaacagucg gcgcttg                                                  17

<210> SEQ ID NO 44
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3A531L12D

<400> SEQUENCE: 44
ccaacagucg gcgcttg                                                  17

<210> SEQ ID NO 45
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3531L17B2

<400> SEQUENCE: 45
ccaacagucg gcgc                                                     14

<210> SEQ ID NO 46
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3531L17B3

<400> SEQUENCE: 46
ccaacagucg gcgc                                                     14

<210> SEQ ID NO 47
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3A531L21

<400> SEQUENCE: 47
ccaacagucg gcgcu                                                    15

<210> SEQ ID NO 48
<211> LENGTH: 14
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3A531L22

<400> SEQUENCE: 48
cccacagucg gcgc                                                           14

<210> SEQ ID NO 49
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3531L17B4

<400> SEQUENCE: 49
ccaacagucg gcgc                                                           14

<210> SEQ ID NO 50
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3531L17B5

<400> SEQUENCE: 50
ccaacagucg gcgc                                                           14

<210> SEQ ID NO 51
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3A531L20B

<400> SEQUENCE: 51 ccaacgucg gcgc                                                            14

<210> SEQ ID NO 52
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RM5L17B3a
```

```
<400> SEQUENCE: 52
ccaacagtcg gcgc                                                14

<210> SEQ ID NO 53
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3F531W

<400> SEQUENCE: 53
cccacagtcg gcgcttg                                             17

<210> SEQ ID NO 54
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3F531W02

<400> SEQUENCE: 54
cccacagtcg gcgcttgt                                            18

<210> SEQ ID NO 55
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3F531W06

<400> SEQUENCE: 55
cccacagtcg gcgc                                                14

<210> SEQ ID NO 56
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3A07

<400> SEQUENCE: 56
cuugaggguc aacccc                                              16

<210> SEQ ID NO 57
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3A07B2
```

-continued

```
<400> SEQUENCE: 57
ttgagggtca accccgacgg gg                                              22

<210> SEQ ID NO 58
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3A08

<400> SEQUENCE: 58
acccucaagc gccg                                                       14

<210> SEQ ID NO 59
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3A08B

<400> SEQUENCE: 59
acccucaagc gcc                                                        13

<210> SEQ ID NO 60
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3A08C

<400> SEQUENCE: 60
acccucaagc gccg                                                       14

<210> SEQ ID NO 61
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3A09

<400> SEQUENCE: 61
cuugaggguc aacccc                                                     16

<210> SEQ ID NO 62
<211> LENGTH: 18
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: AYRPO3526LFM07

<400> SEQUENCE: 62
cuugaggguc aaccccga                                                   18

<210> SEQ ID NO 63
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: AYRPO3526LFM08

<400> SEQUENCE: 63
gcuugagggu caaccccga                                                  19

<210> SEQ ID NO 64
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: AYRPO3526LFM09

<400> SEQUENCE: 64
gcuugagggu caacccga                                                   19

<210> SEQ ID NO 65
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: AYRPO3526LFM10

<400> SEQUENCE: 65
gcuugagggu caacccga                                                   19

<210> SEQ ID NO 66
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

```
      Synthetic oligonucleotide
<220> FEATURE:
<223> OTHER INFORMATION: AYRPO3526LFM11

<400> SEQUENCE: 66
gcuugagggc caaccccga                                                  19

<210> SEQ ID NO 67
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: AYRPO3526LFM12

<400> SEQUENCE: 67
gcuugagggu caaccccga                                                  19

<210> SEQ ID NO 68
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: AYRPO3526LJA01

<400> SEQUENCE: 68
gcuugagggu caaccccga                                                  19

<210> SEQ ID NO 69
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: AYRPO3526LJA02

<400> SEQUENCE: 69
gcuugagggu caaccccga                                                  19

<210> SEQ ID NO 70
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: AYRPO3526LJA03

<400> SEQUENCE: 70
gcuugagggc caaccccga                                                  19
```

```
<210> SEQ ID NO 71
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: AYRPO3526LJA04

<400> SEQUENCE: 71
gcuugagggu caaccccga                                                   19

<210> SEQ ID NO 72
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: AYRPO3526LJA05

<400> SEQUENCE: 72
gcuugagggc caaccccga                                                   19

<210> SEQ ID NO 73
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: AYRPO3526LJA06

<400> SEQUENCE: 73
gcuugagggc caaccccga                                                   19

<210> SEQ ID NO 74
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3A06E

<400> SEQUENCE: 74
uuguagguca accccga                                                     17

<210> SEQ ID NO 75
<211> LENGTH: 18
<212> TYPE: DNA
<213> ORGANISM: Artificial Sequence
<220> FEATURE:
```

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: AYRPO3526YFM07

<400> SEQUENCE: 75
cuuguagguc aaccccga                                                       18

<210> SEQ ID NO 76
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: AYRPO3526YFM08

<400> SEQUENCE: 76
cuuguagguc aaccccga                                                       18

<210> SEQ ID NO 77
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: AYRPO3526YFM09

<400> SEQUENCE: 77
cuuguagguc aaccccga                                                       18

<210> SEQ ID NO 78
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: AYRPO3526YFM10

<400> SEQUENCE: 78
cuuguagguc aaccccga                                                       18

<210> SEQ ID NO 79
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: AYRPO3526YHX01

```
<400> SEQUENCE: 79
cuuguagguc aaccccga                                              18

<210> SEQ ID NO 80
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: AYRPO3526YHX02

<400> SEQUENCE: 80 cuuguaggguc aacccccga                                            18

<210> SEQ ID NO 81
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: AYRPO3526YHX03

<400> SEQUENCE: 81
uuguagguca accccga                                               17

<210> SEQ ID NO 82
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: AYRPO3526YHX04

<400> SEQUENCE: 82
uuguagguca acccc                                                 15

<210> SEQ ID NO 83
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: AYRPO3526YHX05

<400> SEQUENCE: 83
uuguagguca acccc                                                 15

<210> SEQ ID NO 84
```

<210> SEQ ID NO 84
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide
<220> FEATURE:
<223> OTHER INFORMATION: AYRPO3526YHX06

<400> SEQUENCE: 84
cuuguaggcc aaccccga                                         18

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide
<220> FEATURE:
<223> OTHER INFORMATION: AYRPO3526YHX07

<400> SEQUENCE: 85
cuuguagguc aaccccgaca                                       20

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide
<220> FEATURE:
<223> OTHER INFORMATION: AYRPO3526YHX08

<400> SEQUENCE: 86
cgcuuguagg ucaaccccga                                       20

<210> SEQ ID NO 87
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide
<220> FEATURE:
<223> OTHER INFORMATION: AYRPO3526YHX09

<400> SEQUENCE: 87
gcuuguaggu caaccccgac a                                     21

<210> SEQ ID NO 88
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:

```
<223> OTHER INFORMATION: Description of Combined DNA/RNA Molecule:
      Synthetic oligonucleotide
<220> FEATURE:
<223> OTHER INFORMATION: AYRPO3526YHX10

<400> SEQUENCE: 88
cgcuuguagg ucaaccccga ca                                          22

<210> SEQ ID NO 89
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3A03C

<400> SEQUENCE: 89
cuugucgguc aacccc                                                 16

<210> SEQ ID NO 90
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3A03D

<400> SEQUENCE: 90
cuugucgguc aacccc                                                 16

<210> SEQ ID NO 91
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AYRPO3526DFM03

<400> SEQUENCE: 91
tgtcggtcaa ccccga                                                 16

<210> SEQ ID NO 92
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AYRPO3526DFM04

<400> SEQUENCE: 92
tgtcggtcaa ccccga                                                 16

<210> SEQ ID NO 93
<211> LENGTH: 18
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AYRPO3526DFM05

<400> SEQUENCE: 93
gttgtcggtc aaccccga                                                        18

<210> SEQ ID NO 94
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AYRPO3526DFM06

<400> SEQUENCE: 94
gttgtcggtc aaccccga                                                        18

<210> SEQ ID NO 95
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: AYRPO3526DJA07

<400> SEQUENCE: 95
uugucgguca ccccc                                                           15

<210> SEQ ID NO 96
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: AYRPO3526DJA08

<400> SEQUENCE: 96
cuugucgguc aaccccc                                                         16

<210> SEQ ID NO 97
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: AYRPO3526DJA09

<400> SEQUENCE: 97
uugucgguca accccga                                                         17
```

```
<210> SEQ ID NO 98
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: AYRPO3526DJA10

<400> SEQUENCE: 98
cuugucgguc aaccccga                                                 18

<210> SEQ ID NO 99
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: AYRPO3526DJA11

<400> SEQUENCE: 99
gcuugucggu caaccccga                                                19

<210> SEQ ID NO 100
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3SP526R2

<400> SEQUENCE: 100
accaacaagc gccg                                                     14

<210> SEQ ID NO 101
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3SP526R3

<400> SEQUENCE: 101
accaacaagc gccg                                                     14

<210> SEQ ID NO 102
<211> LENGTH: 17
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: RMRPO3AP526R1

<400> SEQUENCE: 102
ttgttggtca accccga                                                17

<210> SEQ ID NO 103
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3AP526N1

<400> SEQUENCE: 103
uuguugguca accc                                                   14

<210> SEQ ID NO 104
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3AP526N2

<400> SEQUENCE: 104
uuguugguca acccg                                                  15

<210> SEQ ID NO 105
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3AP526N2B

<400> SEQUENCE: 105
uuguugguca accc                                                   14

<210> SEQ ID NO 106
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3SP526N4

<400> SEQUENCE: 106
```
accaacaagc gccgacu                                                17

<210> SEQ ID NO 107
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3SP526N4B

<400> SEQUENCE: 107
accaacaagc gccgacu                                                17

<210> SEQ ID NO 108
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3SP526N4B2

<400> SEQUENCE: 108
accaacaagc gccgac                                                 16

<210> SEQ ID NO 109
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3SP526N4B2b

<400> SEQUENCE: 109
accaacaagc gccga                                                  15

<210> SEQ ID NO 110
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3SP526N4B3

<400> SEQUENCE: 110
caacaagcgc cgacug                                                 16

<210> SEQ ID NO 111
<211> LENGTH: 14
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3SP526N4C

<400> SEQUENCE: 111
accaacaagc gccg                                                   14

<210> SEQ ID NO 112
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3SP526N5

<400> SEQUENCE: 112
accaacaagc gccgacu                                                17

<210> SEQ ID NO 113
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3AP526N6

<400> SEQUENCE: 113
uuguugguca accccga                                                17

<210> SEQ ID NO 114
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3AP526N7

<400> SEQUENCE: 114
uuguugguca accccga                                                17

<210> SEQ ID NO 115
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
```

```
<223> OTHER INFORMATION: RMRPO3AP526N8

<400> SEQUENCE: 115
uuguugguca ccccc                                                       15

<210> SEQ ID NO 116
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3AP526N9

<400> SEQUENCE: 116
uuguugguca ccccc                                                       15

<210> SEQ ID NO 117
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3AP526N1B

<400> SEQUENCE: 117
uuguugguca accc                                                        14

<210> SEQ ID NO 118
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3A526N8B

<400> SEQUENCE: 118
uuguugguca ccccc                                                       15

<210> SEQ ID NO 119
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3H533P10B

<400> SEQUENCE: 119
cgccggggcc cggc                                                        14
```

```
<210> SEQ ID NO 120
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3H533P10D

<400> SEQUENCE: 120
cgccggggcc cggcgg                                                    16

<210> SEQ ID NO 121
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3H533P10

<400> SEQUENCE: 121
cgccggggcc cggcgg                                                    16

<210> SEQ ID NO 122
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJS513L44PJ12

<400> SEQUENCE: 122
cagcugagcc uauuc                                                     15

<210> SEQ ID NO 123
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJS513L68PJ12

<400> SEQUENCE: 123
ccuauucaug gaccag                                                    16

<210> SEQ ID NO 124
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide
<220> FEATURE:
<223> OTHER INFORMATION: JJS513L59PJ12

<400> SEQUENCE: 124
ccagcugagc cuauuc                                                   16

<210> SEQ ID NO 125
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJS513L101PJ12

<400> SEQUENCE: 125
agccuauuca uggaccag                                                 18

<210> SEQ ID NO 126
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJS513L84PJ12

<400> SEQUENCE: 126
gccuauucat ggaccag                                                  17

<210> SEQ ID NO 127
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJA513L60PJ12

<400> SEQUENCE: 127
ugaauaggcu cagcug                                                   16

<210> SEQ ID NO 128
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJA513L68PJ12

<400> SEQUENCE: 128
```
cugguccaug aataag                                                   16

<210> SEQ ID NO 129
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJA513L103PJ12

<400> SEQUENCE: 129
uucuggucca ugaauagg                                                 18

<210> SEQ ID NO 130
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJA513L61PJ12

<400> SEQUENCE: 130
augaauaggc ucagcu                                                   16

<210> SEQ ID NO 131
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJA513L76PJ12

<400> SEQUENCE: 131
ugaauaggcu cagcugg                                                  17

<210> SEQ ID NO 132
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJA513L59PJ12

<400> SEQUENCE: 132
gaauaggcuc agcugg                                                   16

<210> SEQ ID NO 133
<211> LENGTH: 18
<212> TYPE: DNA

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJA513L95PJ12

<400> SEQUENCE: 133
caugaauagg cucagcug                                                  18

<210> SEQ ID NO 134
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJA513L924PJ2

<400> SEQUENCE: 134
gaauaggcuc aguuggcu                                                  18

<210> SEQ ID NO 135
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJA513L928PJ2

<400> SEQUENCE: 135
gaauagguuc agcuggcu                                                  18

<210> SEQ ID NO 136
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJA513L927PJ2

<400> SEQUENCE: 136
gaauaggcuu agcuggcu                                                  18

<210> SEQ ID NO 137
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<220> FEATURE:
<223> OTHER INFORMATION: JJA513L9232PJ2

<400> SEQUENCE: 137
gaauaggcug agcuggcu                                                 18

<210> SEQ ID NO 138
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJA513L9243PJ2

<400> SEQUENCE: 138
gaauaggcuc cgcuggcu                                                 18

<210> SEQ ID NO 139
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJA513L9217PJ2

<400> SEQUENCE: 139
gaauaggcuc agcaggcu                                                 18

<210> SEQ ID NO 140
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJA513L9218PJ2

<400> SEQUENCE: 140
gaauaggcuc agauggcu                                                 18

<210> SEQ ID NO 141
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJA513L9222PJ2

<400> SEQUENCE: 141
gaauaggauc agcuggcu                                                 18
```

```
<210> SEQ ID NO 142
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJA513L75PJ12

<400> SEQUENCE: 142
gaauaggcuc agcuggc                                                    17

<210> SEQ ID NO 143
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJA513L75PCA12

<400> SEQUENCE: 143
gaauaggcuc agcuggc                                                    17

<210> SEQ ID NO 144
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJA513L75PCB12

<400> SEQUENCE: 144
tgaauaggcu cagcuggc                                                   18

<210> SEQ ID NO 145
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJA513L77PJ12

<400> SEQUENCE: 145
augaauaggc ucagcug                                                    17

<210> SEQ ID NO 146
<211> LENGTH: 18
<212> TYPE: DNA
<213> ORGANISM: Artificial Sequence
<220> FEATURE:
<223> OTHER INFORMATION: Description of Artificial Sequence: Synthetic
```

```
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJA513L93PJ12

<400> SEQUENCE: 146
ugaauaggcu cagcuggc                                                   18

<210> SEQ ID NO 147
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJS513L85PJ12

<400> SEQUENCE: 147
ccuauucaug gaccaga                                                    17

<210> SEQ ID NO 148
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJS513K84PJ12

<400> SEQUENCE: 148
agcaaauuca uggacca                                                    17

<210> SEQ ID NO 149
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJS513K77PJ12

<400> SEQUENCE: 149
ccagcugagc aaauuca                                                    17

<210> SEQ ID NO 150
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJS513K79PJ12
```

```
<400> SEQUENCE: 150
agcugagcaa auucaug                                              17

<210> SEQ ID NO 151
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJS513K85PJ12

<400> SEQUENCE: 151
gcaaauucau ggaccag                                              17

<210> SEQ ID NO 152
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJA513K43PJ12

<400> SEQUENCE: 152
auuugcucag cuggc                                                15

<210> SEQ ID NO 153
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJA513K77PJ12

<400> SEQUENCE: 153
ugaauuugcu cagcugg                                              17

<210> SEQ ID NO 154
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJA513K60PJ12

<400> SEQUENCE: 154
gaauuugcuc agcugg                                               16

<210> SEQ ID NO 155
<211> LENGTH: 17
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJA513K76PJ12

<400> SEQUENCE: 155
gaauuugcuc agcuggc                                                   17

<210> SEQ ID NO 156
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJA513K76PCA12

<400> SEQUENCE: 156
gaauuugcuc agcuggc                                                   17

<210> SEQ ID NO 157
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJA513K76PCB12

<400> SEQUENCE: 157
tgaauuugcu cagcuggc                                                  18

<210> SEQ ID NO 158
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJA513K44PJ12

<400> SEQUENCE: 158
aauuugcuca gcugg                                                     15

<210> SEQ ID NO 159
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

Synthetic oligonucleotide
<220> FEATURE:
<223> OTHER INFORMATION: JJA513K80PJ12

<400> SEQUENCE: 159
ccaugaauuu gcucagc                                                    17

<210> SEQ ID NO 160
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJA513K59PJ12

<400> SEQUENCE: 160
aauuugcuca gcuggc                                                     16

<210> SEQ ID NO 161
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJA513K75PJ12

<400> SEQUENCE: 161
aauuugcuca gcuggcu                                                    17

<210> SEQ ID NO 162
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJS513P66PJ12

<400> SEQUENCE: 162
agcccauuca uggacc                                                     16

<210> SEQ ID NO 163
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJS513P83PJ12

<400> SEQUENCE: 163
agcccauuca uggacca                                                    17

<210> SEQ ID NO 164
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJS513P68PJ12

<400> SEQUENCE: 164
cccauucaug gaccag                                                     16

<210> SEQ ID NO 165
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JS513P81PJ12

<400> SEQUENCE: 165
ugagcccauu cauggac                                                    17

<210> SEQ ID NO 166
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJA513P60PJ12

<400> SEQUENCE: 166
ugaaugggcu cagcug                                                     16

<210> SEQ ID NO 167
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJA513P76PJ12

<400> SEQUENCE: 167
ugaaugggct cagcugg                                                    17

<210> SEQ ID NO 168
<211> LENGTH: 16
<212> TYPE: DNA
<213> ORGANISM: Artificial Sequence
<220> FEATURE:

<223> OTHER INFORMATION: Description of Artificial Sequence: Synthetic
     oligonucleotide
<220> FEATURE:
<223> OTHER INFORMATION: Description of Combined DNA/RNA Molecule:
     Synthetic oligonucleotide
<220> FEATURE:
<223> OTHER INFORMATION: JJS513P66GJ12

<400> SEQUENCE: 168
agcccauuca uggacc                                                     16

<210> SEQ ID NO 169
<211> LENGTH: 17
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: Description of Combined DNA/RNA Molecule:
     Synthetic oligonucleotide
<220> FEATURE:
<223> OTHER INFORMATION: JJS513P83GJ12

<400> SEQUENCE: 169
agcccauuca uggacca                                                    17

<210> SEQ ID NO 170
<211> LENGTH: 17
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: Description of Combined DNA/RNA Molecule:
     Synthetic oligonucleotide
<220> FEATURE:
<223> OTHER INFORMATION: JJS513P84PJ12

<400> SEQUENCE: 170
gcccauucau ggaccag                                                    17

<210> SEQ ID NO 171
<211> LENGTH: 17
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: Description of Combined DNA/RNA Molecule:
     Synthetic oligonucleotide
<220> FEATURE:
<223> OTHER INFORMATION: JJS513P82PJ12

<400> SEQUENCE: 171
gagcccauuc auggacc                                                    17

<210> SEQ ID NO 172
<211> LENGTH: 17
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: Description of Combined DNA/RNA Molecule:
     Synthetic oligonucleotide
<220> FEATURE:
<223> OTHER INFORMATION: JJS513P84GJ12

```
<400> SEQUENCE: 172
gcccauucau ggaccag                                                  17

<210> SEQ ID NO 173
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJS513P82GJ12

<400> SEQUENCE: 173
gagcccauuc auggacc                                                  17

<210> SEQ ID NO 174
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJA522L50PJ12

<400> SEQUENCE: 174
ggucaacccc aacag                                                    15

<210> SEQ ID NO 175
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: JJA522L18PJ12

<400> SEQUENCE: 175
accccaacag cgg                                                      13

<210> SEQ ID NO 176
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJA522L16PJ12

<400> SEQUENCE: 176
cccaacagcg ggu                                                      13

<210> SEQ ID NO 177
<211> LENGTH: 13
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: JJA522L17PJ12

<400> SEQUENCE: 177
ccccaacagc ggg                                                          13

<210> SEQ ID NO 178
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJA522L83PJ12

<400> SEQUENCE: 178
ugggucaacc ccaacag                                                      17

<210> SEQ ID NO 179
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: JJA522L32PJ12

<400> SEQUENCE: 179
aaccccaaca gcgg                                                         14

<210> SEQ ID NO 180
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: JJA522L33PJ12

<400> SEQUENCE: 180
caaccccaac agcg                                                         14

<210> SEQ ID NO 181
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJA522L48PJ12

<400> SEQUENCE: 181
ucaaccccaa cagcg                                                        15

<210> SEQ ID NO 182
<211> LENGTH: 14
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJA522L30PJ12

<400> SEQUENCE: 182
ccccaacagc gggu                                                         14

<210> SEQ ID NO 183
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: JJA522L31PJ12

<400> SEQUENCE: 183
accccaacag cggg                                                         14

<210> SEQ ID NO 184
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJA522L63PJ12

<400> SEQUENCE: 184
ucaaccccaa cagcgg                                                       16

<210> SEQ ID NO 185
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: JJA522L47PJ12

<400> SEQUENCE: 185
caaccccaac agcgg                                                        15

<210> SEQ ID NO 186
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: JJS522Q48J12

<400> SEQUENCE: 186
ccgctgcagg ggttga                                                       16
```

```
<210> SEQ ID NO 187
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: JJS522Q32J12

<400> SEQUENCE: 187
cccgctgcag gggtt                                                15

<210> SEQ ID NO 188
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: JJS522Q49J12

<400> SEQUENCE: 188
cgctgcaggg gttgac                                               16

<210> SEQ ID NO 189
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: JJA522Q31J12

<400> SEQUENCE: 189
acccctgcag cgggt                                                15

<210> SEQ ID NO 190
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: JJA522Q33J12

<400> SEQUENCE: 190
caacccctgc agcgg                                                15

<210> SEQ ID NO 191
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: JJA522Q43J12

<400> SEQUENCE: 191
ccctgcagcg ggttgt                                               16

<210> SEQ ID NO 192
<211> LENGTH: 15
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJA522Q31PJ12

<400> SEQUENCE: 192
accccugcag cgggu                                                      15

<210> SEQ ID NO 193
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJS522Q49PJ12

<400> SEQUENCE: 193
cgcugcaggg guugac                                                     16

<210> SEQ ID NO 194
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJA522Q18PJ12

<400> SEQUENCE: 194
accccugcag cggg                                                       14

<210> SEQ ID NO 195
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJS522Q34PJ12

<400> SEQUENCE: 195
cgcugcaggg guuga                                                      15

<210> SEQ ID NO 196
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
```

```
<223> OTHER INFORMATION: JJA522Q20PJ12

<400> SEQUENCE: 196 caacccougc agcg                                                         14

<210> SEQ ID NO 197
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJA522Q33PJ12

<400> SEQUENCE: 197 caacccougc agcgg                                                        15

<210> SEQ ID NO 198
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJA522Q47PJ12

<400> SEQUENCE: 198 caacccougc agcggg                                                       16

<210> SEQ ID NO 199
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJA522W33PJ12

<400> SEQUENCE: 199 caaccccac agcg                                                          14

<210> SEQ ID NO 200
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJA522W33GJ12

<400> SEQUENCE: 200 caaccccac agcg                                                          14
```

```
<210> SEQ ID NO 201
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJA522W47J12

<400> SEQUENCE: 201 caaccccac agcgg                                                       15

<210> SEQ ID NO 202
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJA522W47GJ12

<400> SEQUENCE: 202 caaccccac agcgg                                                       15

<210> SEQ ID NO 203
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJA522W48PJ12

<400> SEQUENCE: 203 ucaacccca cagcg                                                       15

<210> SEQ ID NO 204
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: JJA522W48GJ12

<400> SEQUENCE: 204 ucaacccca cagcg                                                       15

<210> SEQ ID NO 205
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
```

<220> FEATURE:
<223> OTHER INFORMATION: RMRPO3F516V

<400> SEQUENCE: 205
ctggaccatg aattggctc                                                19

<210> SEQ ID NO 206
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3UNF516V

<400> SEQUENCE: 206
ctggaccatg aattggctc                                                19

<210> SEQ ID NO 207
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3SP516V

<400> SEQUENCE: 207
tggtccagaa caacccgct                                                19

<210> SEQ ID NO 208
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3SP516Y

<400> SEQUENCE: 208
atgtaccaga acaacccgct g                                             21

<210> SEQ ID NO 209
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3AP516Y

<400> SEQUENCE: 209
ctggtacatg aattggctc                                                19

<210> SEQ ID NO 210
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3A2P516Y

<400> SEQUENCE: 210
ctggtacatg aattggctca gc                                          22

<210> SEQ ID NO 211
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3F516V02

<400> SEQUENCE: 211
ctggaccatg aattggctc                                              19

<210> SEQ ID NO 212
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3SP516V03

<400> SEQUENCE: 212
tggtccagaa caacccgctg cgg                                         23

<210> SEQ ID NO 213
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3SP516V04

<400> SEQUENCE: 213
tggtccaaaa caacccgct                                              19

<210> SEQ ID NO 214
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3SP516V05

<400> SEQUENCE: 214
tggtccagaa caacccgct                                              19

<210> SEQ ID NO 215
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3SP516V06

<400> SEQUENCE: 215
tggtccagaa caacccgct                                              19

```
<210> SEQ ID NO 216
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3SP516Y02

<400> SEQUENCE: 216
atgtaccaga acaacccggg gt                                               22

<210> SEQ ID NO 217
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3SP516V07

<400> SEQUENCE: 217
tggtccagaa taacccgctg cgg                                              23

<210> SEQ ID NO 218
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3SP516V08

<400> SEQUENCE: 218
tggtccaaaa caacccgctg cgg                                              23

<210> SEQ ID NO 219
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3SP516V09

<400> SEQUENCE: 219
ggtccagaac aacccgctg                                                   19

<210> SEQ ID NO 220
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3SP516V10

<400> SEQUENCE: 220
atggtccaga acaacccgct                                                  20

<210> SEQ ID NO 221
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: RMRPO3SP516V11

<400> SEQUENCE: 221
catggtccag aacaacccg                                                    19

<210> SEQ ID NO 222
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3SP516V12

<400> SEQUENCE: 222
atggtccaga acaaccggtt g                                                 21

<210> SEQ ID NO 223
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3S516V11B

<400> SEQUENCE: 223
catggtccag aacaacccg                                                    19

<210> SEQ ID NO 224
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3S516V11C

<400> SEQUENCE: 224
caugguccag aacaacccg                                                    19

<210> SEQ ID NO 225
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3S516V11D

<400> SEQUENCE: 225
catggtccag aacaacccg                                                    19

<210> SEQ ID NO 226
<211> LENGTH: 18
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: RMRPO3S516V11E

<400> SEQUENCE: 226
atggtccaga acaacccg                                                      18

<210> SEQ ID NO 227
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3S516V11F

<400> SEQUENCE: 227
catggtccag aacaacccg                                                     19

<210> SEQ ID NO 228
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3S516V11G

<400> SEQUENCE: 228
caugguccag aacaac                                                        16

<210> SEQ ID NO 229
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3516V11C2

<400> SEQUENCE: 229
caugguccag aacaac                                                        16

<210> SEQ ID NO 230
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RM516V11G2

<400> SEQUENCE: 230
ccugguccag aacaac                                                        16
```

```
<210> SEQ ID NO 231
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3516V11G2

<400> SEQUENCE: 231
caugguccag aaca                                                        14

<210> SEQ ID NO 232
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3516V11G3

<400> SEQUENCE: 232
cauggtccag aaca                                                        14

<210> SEQ ID NO 233
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3S516V12B

<400> SEQUENCE: 233
catggtccag aacaaccggt tg                                               22

<210> SEQ ID NO 234
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: RMRPO3516V11C4

<400> SEQUENCE: 234
caugguccag aacaacc                                                     17

<210> SEQ ID NO 235
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3516V11E2
```

```
<400> SEQUENCE: 235
tggtccagaa caacccgctg                                              20

<210> SEQ ID NO 236
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3516V11E3

<400> SEQUENCE: 236
atggtccaga acaacagttg                                              20

<210> SEQ ID NO 237
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3516V11E5

<400> SEQUENCE: 237
tggtccagaa caacccgct                                               19

<210> SEQ ID NO 238
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3516V11E6

<400> SEQUENCE: 238
tggtccagaa caacccgct                                               19

<210> SEQ ID NO 239
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3SP516Y03

<400> SEQUENCE: 239
atgtaccaga acaacccgc                                               19

<210> SEQ ID NO 240
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3S516YB2

<400> SEQUENCE: 240
atgtaccaga acaacccgct g                                            21
```

<210> SEQ ID NO 241
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3SP516Y

<400> SEQUENCE: 241
atgtaccaga acaacccgct g                                             21

<210> SEQ ID NO 242
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3AP516Y

<400> SEQUENCE: 242
ctggtacatg aattggctc                                                19

<210> SEQ ID NO 243
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3A2P516Y

<400> SEQUENCE: 243
ctggtacatg aattggctca gc                                            22

<210> SEQ ID NO 244
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3SP516Y02

<400> SEQUENCE: 244
atgtaccaga acaacccggg gt                                            22

<210> SEQ ID NO 245
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3SP516Y4B

<400> SEQUENCE: 245
atgtaccaga acaacccgct gt                                            22

<210> SEQ ID NO 246
<211> LENGTH: 21
<212> TYPE: DNA

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3S516YB

<400> SEQUENCE: 246
atgtaccaga acaacccgct g                                            21

<210> SEQ ID NO 247
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3S516YC

<400> SEQUENCE: 247
atgtaccaga acaacccgct g                                            21

<210> SEQ ID NO 248
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3H533P10B

<400> SEQUENCE: 248
cgccggggcc cggc                                                    14

<210> SEQ ID NO 249
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3H533P10D

<400> SEQUENCE: 249
cgccggggcc cggcgg                                                  16

<210> SEQ ID NO 250
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3H533

<400> SEQUENCE: 250
ccggcgccga cagtcggcg                                               19

<210> SEQ ID NO 251
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: RMRPO3H533P02

<400> SEQUENCE: 251
ccggcgccga cagtcgg                                              17

<210> SEQ ID NO 252
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3H533P03

<400> SEQUENCE: 252
ccggcgccta cagtcggcg                                            19

<210> SEQ ID NO 253
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3H533P04

<400> SEQUENCE: 253
ccggcgccaa cagtcggcg                                            19

<210> SEQ ID NO 254
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3H533P05

<400> SEQUENCE: 254
ccggcgccca cagtcggcg                                            19

<210> SEQ ID NO 255
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3H533P06

<400> SEQUENCE: 255
ccggcaccga cagtcgg                                              17

<210> SEQ ID NO 256
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3H533P07

<400> SEQUENCE: 256
```

-continued ccggcgtcga cagtcgg        17

<210> SEQ ID NO 257
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3H533P08

<400> SEQUENCE: 257
ccggcgccga cagtcggc        18

<210> SEQ ID NO 258
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3H533P09

<400> SEQUENCE: 258
ccggcaccga cagtcggc        18

<210> SEQ ID NO 259
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3H533P10

<400> SEQUENCE: 259
cgccggggcc cggcgg        16

<210> SEQ ID NO 260
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3H533P11

<400> SEQUENCE: 260
cgccggggcc cggcg        15

<210> SEQ ID NO 261
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3H533P12

<400> SEQUENCE: 261
cgccggggcc cggc        14

```
<210> SEQ ID NO 262
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3H533P8B

<400> SEQUENCE: 262
ccggcgccga cagtcgg                                                    17

<210> SEQ ID NO 263
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3H533P8C

<400> SEQUENCE: 263
ccggcgccga cagtcg                                                     16

<210> SEQ ID NO 264
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3H533P13

<400> SEQUENCE: 264
cgccggggcc ggcc                                                       14

<210> SEQ ID NO 265
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3H533P10C

<400> SEQUENCE: 265
cgccggggcc cggcgg                                                     16

<210> SEQ ID NO 266
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3H533P10E

<400> SEQUENCE: 266
cgccggggcc cggcgg                                                     16

<210> SEQ ID NO 267
<211> LENGTH: 14
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: RMRPO3533P10C2

<400> SEQUENCE: 267
cgccggggcc cggc                                                    14

<210> SEQ ID NO 268
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3533P12B

<400> SEQUENCE: 268
cgccggggcc cggc                                                    14

<210> SEQ ID NO 269
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3533P12C

<400> SEQUENCE: 269
cgccggggcc cggc                                                    14

<210> SEQ ID NO 270
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3533P12B2

<400> SEQUENCE: 270
cgccggggcc cggcgc                                                  16

<210> SEQ ID NO 271
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3533P12C2

<400> SEQUENCE: 271
cgccggggcc cggcgg                                                  16

<210> SEQ ID NO 272
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

<223> OTHER INFORMATION: RMRPO3533P12C3

<400> SEQUENCE: 272
cgccgaggcc cggcgg                                                          16

<210> SEQ ID NO 273
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3533P12C4

<400> SEQUENCE: 273
agccggggcc cggcgg                                                          16

<210> SEQ ID NO 274
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3533P13

<400> SEQUENCE: 274
ccggggcccg gcgg                                                            14

<210> SEQ ID NO 275
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3533P14

<400> SEQUENCE: 275
ccggggcccg gcgg                                                            14

<210> SEQ ID NO 276
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RMRPO3H533P02B

<400> SEQUENCE: 276
ccggcgccga cagtc                                                           15

<210> SEQ ID NO 277
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AYRPO3511PFM01

<400> SEQUENCE: 277

```
cagccgagcc aattcatg                                                 18

<210> SEQ ID NO 278
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AYRPO3511PFM02

<400> SEQUENCE: 278
cagccgagcc aattcatg                                                 18

<210> SEQ ID NO 279
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AYRPO3511PFM03

<400> SEQUENCE: 279
cagccgagcc aattcatg                                                 18

<210> SEQ ID NO 280
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AYRPO3511PFM04

<400> SEQUENCE: 280
cagccgagcc aattcatg                                                 18

<210> SEQ ID NO 281
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AYRPO3511PFM05

<400> SEQUENCE: 281
cagccgagcc aattcatg                                                 18

<210> SEQ ID NO 282
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AYRPO3526RFM01

<400> SEQUENCE: 282
cttgcgggtc aaccccga                                                 18

<210> SEQ ID NO 283
```

```
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AYRPO3526RFM02

<400> SEQUENCE: 283
tgcgggtcaa ccccga                                                      16

<210> SEQ ID NO 284
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AYRPO3526RFM03

<400> SEQUENCE: 284
tgcgggtcaa ccccga                                                      16

<210> SEQ ID NO 285
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AYRPO3526RFM04

<400> SEQUENCE: 285
cttgcgggtc aaccccga                                                    18

<210> SEQ ID NO 286
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AYRPO3526RFM05

<400> SEQUENCE: 286
cttgcgggtc aaccccga                                                    18

<210> SEQ ID NO 287
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AYRPO3526RFM06

<400> SEQUENCE: 287
tgcgggtcaa ccccga                                                      16

<210> SEQ ID NO 288
<211> LENGTH: 16
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: AYRPO3526RFM07

<400> SEQUENCE: 288
tgcgggtcaa ccccga                                                         16

<210> SEQ ID NO 289
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AYRPO3526RFM08

<400> SEQUENCE: 289
cttgcgggtc aaccccga                                                       18

<210> SEQ ID NO 290
<211> LENGTH: 18
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYKAT315ICM01

<400> SEQUENCE: 290
gatcaccatc ggcatcga                                                       18

<210> SEQ ID NO 291
<211> LENGTH: 19
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYKAT315ICM02

<400> SEQUENCE: 291
caccatcggc atcgaggtc                                                      19

<210> SEQ ID NO 292
<211> LENGTH: 19
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYKAT315ICM03

<400> SEQUENCE: 292
catcggcatc gaggtcgta                                                      19

<210> SEQ ID NO 293
<211> LENGTH: 22
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYKAT315ICM04
```

```
<400> SEQUENCE: 293
caccatcggc atcgaggtcg ta                                              22

<210> SEQ ID NO 294
<211> LENGTH: 18
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYKAT315ICM05

<400> SEQUENCE: 294
atcggcatcg aggtcgta                                                   18

<210> SEQ ID NO 295
<211> LENGTH: 18
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: AYKAT315ICM06

<400> SEQUENCE: 295
aucggcaucg aggucgua                                                   18

<210> SEQ ID NO 296
<211> LENGTH: 18
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: AYKAT315ICM07

<400> SEQUENCE: 296
aucggcaucg aggucgua                                                   18

<210> SEQ ID NO 297
<211> LENGTH: 19
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYKAT315ICM03a

<400> SEQUENCE: 297
catcggcatc gaggtcgta                                                  19

<210> SEQ ID NO 298
<211> LENGTH: 19
<212> TYPE: DNA
<213> ORGANISM: Artificial Sequence
<220> FEATURE:
<223> OTHER INFORMATION: Description of Artificial Sequence: Synthetic
      probe
```

<220> FEATURE:
<223> OTHER INFORMATION: AYKAT315ICM03b

<400> SEQUENCE: 298
catcggcatc gaggtcgta                                                19

<210> SEQ ID NO 299
<211> LENGTH: 19
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYKAT315ICM03c

<400> SEQUENCE: 299
catcggcatc gaggtcgta                                                19

<210> SEQ ID NO 300
<211> LENGTH: 19
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYKAT315ICM03d

<400> SEQUENCE: 300
catcggcatc gaggtcgta                                                19

<210> SEQ ID NO 301
<211> LENGTH: 19
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYKAT315ICY03a1

<400> SEQUENCE: 301
catcggcatc gaggtcgta                                                19

<210> SEQ ID NO 302
<211> LENGTH: 19
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYKAT315ICY03a2

<400> SEQUENCE: 302
catcggcatc gaggtcgta                                                19

<210> SEQ ID NO 303
<211> LENGTH: 19
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYKAT315ICY03a3

<400> SEQUENCE: 303
catcggcatc gaggtcgta                                                19

<210> SEQ ID NO 304
<211> LENGTH: 19
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYKAT315ICY03a4

<400> SEQUENCE: 304
catcggcatc gaggtcgta                                                19

<210> SEQ ID NO 305
<211> LENGTH: 19
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYKAT315NCM01

<400> SEQUENCE: 305
caacggcatc gaggtcgta                                                19

<210> SEQ ID NO 306
<211> LENGTH: 19
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYKAT315NCM02

<400> SEQUENCE: 306
caacggcatc gaggtcgta                                                19

<210> SEQ ID NO 307
<211> LENGTH: 19
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYKAT315NCM03

<400> SEQUENCE: 307
caacggcatc gaggtcgta                                                19

<210> SEQ ID NO 308
<211> LENGTH: 19
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYKAT315NCM04

<400> SEQUENCE: 308
caacggcatc gaggtcgta                                                19

-continued

```
<210> SEQ ID NO 309
<211> LENGTH: 19
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYKAT315NCM05

<400> SEQUENCE: 309
caacggcatc gaggtcgta                                                19

<210> SEQ ID NO 310
<211> LENGTH: 19
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYKAT315NCM04a

<400> SEQUENCE: 310
caacggcatc gaggtcgta                                                19

<210> SEQ ID NO 311
<211> LENGTH: 19
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYKAT315NCM05a

<400> SEQUENCE: 311
caacggcatc gaggtcgta                                                19

<210> SEQ ID NO 312
<211> LENGTH: 19
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYKAT315NCM07

<400> SEQUENCE: 312
caacggcatc gaggtcgta                                                19

<210> SEQ ID NO 313
<211> LENGTH: 18
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYKAT315NCM08

<400> SEQUENCE: 313
aacggcatcg aggtcgta                                                 18

<210> SEQ ID NO 314
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      probe
<220> FEATURE:
<223> OTHER INFORMATION: AYKAT315NCM09

<400> SEQUENCE: 314
caccaacggc atcgaggtc                                                      19

<210> SEQ ID NO 315
<211> LENGTH: 22
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYKAT315NCM10

<400> SEQUENCE: 315
caccaacggc atcgaggtcg ta                                                  22

<210> SEQ ID NO 316
<211> LENGTH: 19
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYKAT315NCM11

<400> SEQUENCE: 316
caacggcatc gaggtcgta                                                      19

<210> SEQ ID NO 317
<211> LENGTH: 18
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYKAT315NCM12

<400> SEQUENCE: 317
aacggcatcg aggtcgta                                                       18

<210> SEQ ID NO 318
<211> LENGTH: 19
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYKAT315NCM13

<400> SEQUENCE: 318
caccaacggc atcgaggtc                                                      19

<210> SEQ ID NO 319
<211> LENGTH: 22
<212> TYPE: DNA
<213> ORGANISM: Artificial Sequence
<220> FEATURE:
<223> OTHER INFORMATION: Description of Artificial Sequence: Synthetic
      probe
<220> FEATURE:
```

-continued

<223> OTHER INFORMATION: AYKAT315NCM14

<400> SEQUENCE: 319
caccaacggc atcgaggtcg ta                                              22

<210> SEQ ID NO 320
<211> LENGTH: 19
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYKAT315NCM15

<400> SEQUENCE: 320
caacggcatc gaggtcgta                                                  19

<210> SEQ ID NO 321
<211> LENGTH: 18
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYKAT315NCM16

<400> SEQUENCE: 321
aacggcatcg aggtcgta                                                   18

<210> SEQ ID NO 322
<211> LENGTH: 19
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYKAT315NCM17

<400> SEQUENCE: 322
caccaacggc atcgaggtc                                                  19

<210> SEQ ID NO 323
<211> LENGTH: 22
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYKAT315NCM18

<400> SEQUENCE: 323
caccaacggc atcgaggtcg ta                                              22

<210> SEQ ID NO 324
<211> LENGTH: 19
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYKAT315NCM19

<400> SEQUENCE: 324
caacggcatc gaggtcgta                                                  19

<210> SEQ ID NO 325
<211> LENGTH: 20
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYKAT315NCM20

<400> SEQUENCE: 325
ccaacggcat cgaggtcgta                                                 20

<210> SEQ ID NO 326
<211> LENGTH: 20
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYKAT315NCM21

<400> SEQUENCE: 326
ccaacggcat cgaggtcgta                                                 20

<210> SEQ ID NO 327
<211> LENGTH: 21
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYKAT315NCM22

<400> SEQUENCE: 327
accaacggca tcgaggtcgt a                                               21

<210> SEQ ID NO 328
<211> LENGTH: 21
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYKAT315NCM23

<400> SEQUENCE: 328
accaacggca tcgaggtcgt a                                               21

<210> SEQ ID NO 329
<211> LENGTH: 19
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYKAT315TCM01

<400> SEQUENCE: 329
caccaccggc atcgaggtc                                                  19

<210> SEQ ID NO 330

```
<211> LENGTH: 19
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYKAT315TCM02

<400> SEQUENCE: 330
caccaccggc atcgaggtc                                               19

<210> SEQ ID NO 331
<211> LENGTH: 19
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYKAT315TCM03

<400> SEQUENCE: 331
caccggcatc gaggtcgta                                               19

<210> SEQ ID NO 332
<211> LENGTH: 16
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYKAT315TCM04

<400> SEQUENCE: 332
caccggcatc gaggtc                                                  16

<210> SEQ ID NO 333
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYKAT315TCM05

<400> SEQUENCE: 333
caccaccggc atcga                                                   15

<210> SEQ ID NO 334
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYKAT315TCM05a

<400> SEQUENCE: 334
caccaccggc atcga                                                   15

<210> SEQ ID NO 335
<211> LENGTH: 15
<212> TYPE: DNA
<213> ORGANISM: Artificial Sequence
<220> FEATURE:
```

```
<223> OTHER INFORMATION: Description of Artificial Sequence: Synthetic
      probe
<220> FEATURE:
<223> OTHER INFORMATION: AYKAT315TCM05b

<400> SEQUENCE: 335
caccaccggc atcga                                                          15

<210> SEQ ID NO 336
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYKAT315TCM05c

<400> SEQUENCE: 336
caccaccggc atcga                                                          15

<210> SEQ ID NO 337
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYKAT315TCY05b1

<400> SEQUENCE: 337
caccaccggc atcga                                                          15

<210> SEQ ID NO 338
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: AYKAT315TCY05b2

<400> SEQUENCE: 338
caccaccggc atcga                                                          15

<210> SEQ ID NO 339
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYKAT315TCY05b3

<400> SEQUENCE: 339
caccaccggc atcga                                                          15

<210> SEQ ID NO 340
<211> LENGTH: 15
<212> TYPE: DNA
<213> ORGANISM: Artificial Sequence
<220> FEATURE:
<223> OTHER INFORMATION: Description of Artificial Sequence: Synthetic
```

```
      probe
<220> FEATURE:
<223> OTHER INFORMATION: AYKAT315TCY05b4

<400> SEQUENCE: 340
caccaccggc atcga                                                15

<210> SEQ ID NO 341
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYKAT315T2CM01

<400> SEQUENCE: 341
caccacaggc atcga                                                15

<210> SEQ ID NO 342
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYKAT315T2CM02

<400> SEQUENCE: 342
caccacaggc atcga                                                15

<210> SEQ ID NO 343
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYKAT315T2CM03

<400> SEQUENCE: 343
caccacaggc atcga                                                15

<210> SEQ ID NO 344
<211> LENGTH: 20
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYINHA15TCM01

<400> SEQUENCE: 344
gcgagatgat aggttgtcgg                                           20

<210> SEQ ID NO 345
<211> LENGTH: 23
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYINHA15TCM02
```

```
<400> SEQUENCE: 345
gagatgatag gttgtcgggg tga                                              23

<210> SEQ ID NO 346
<211> LENGTH: 20
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: AYINHA15TCM03

<400> SEQUENCE: 346
gcgagaugau agguugucgg                                                  20

<210> SEQ ID NO 347
<211> LENGTH: 22
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYINHA15TCM04

<400> SEQUENCE: 347
agatgatagg ttgtcggggt ga                                               22

<210> SEQ ID NO 348
<211> LENGTH: 22
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: AYINHA15TCM05

<400> SEQUENCE: 348
agaugauagg uugucggggu ga                                               22

<210> SEQ ID NO 349
<211> LENGTH: 21
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYINHA15TCM06

<400> SEQUENCE: 349
gatgataggt tgtcggggtg a                                                21

<210> SEQ ID NO 350
<211> LENGTH: 22
<212> TYPE: DNA
<213> ORGANISM: Artificial Sequence
<220> FEATURE:
<223> OTHER INFORMATION: Description of Artificial Sequence: Synthetic
      probe
<220> FEATURE:
```

<223> OTHER INFORMATION: AYINHA15TCM04a

<400> SEQUENCE: 350
agatgatagg ttgtcggggt ga                                              22

<210> SEQ ID NO 351
<211> LENGTH: 22
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYINHA15TCM04b

<400> SEQUENCE: 351
agatgatagg ttgtcggggt ga                                              22

<210> SEQ ID NO 352
<211> LENGTH: 22
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYINHA15TCM04c

<400> SEQUENCE: 352
agatgatagg ttgtcggggt ga                                              22

<210> SEQ ID NO 353
<211> LENGTH: 22
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYINHA15TCM04d

<400> SEQUENCE: 353
agatgatagg ttgtcggggt ga                                              22

<210> SEQ ID NO 354
<211> LENGTH: 22
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: AYINHA15TCM07

<400> SEQUENCE: 354
agaugauagg uugucggggu ga                                              22

<210> SEQ ID NO 355
<211> LENGTH: 21
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:

-continued

Synthetic probe
<220> FEATURE:
<223> OTHER INFORMATION: AYINHA15TCM08

<400> SEQUENCE: 355
gaugauaggu ugucggggug a                                              21

<210> SEQ ID NO 356
<211> LENGTH: 20
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: AYINHA15TCM09

<400> SEQUENCE: 356
augauagguu gucgggguga                                                20

<210> SEQ ID NO 357
<211> LENGTH: 20
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: AYINHA15TCM09a

<400> SEQUENCE: 357
augauagguu gucgggguga                                                20

<210> SEQ ID NO 358
<211> LENGTH: 20
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: AYINHA15TCM09b

<400> SEQUENCE: 358
atgauagguu gucgggguga                                                20

<210> SEQ ID NO 359
<211> LENGTH: 21
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: AYINHA15TCM06a

<400> SEQUENCE: 359
gaugauaggu ugucggggug a                                              21

```
<210> SEQ ID NO 360
<211> LENGTH: 21
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: AYINHA15TCM06b

<400> SEQUENCE: 360
gatgauaggu ugucggggug a                                              21

<210> SEQ ID NO 361
<211> LENGTH: 21
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: JFINHA15TCM06A_1

<400> SEQUENCE: 361
gaugauaggu ugucggggug a                                              21

<210> SEQ ID NO 362
<211> LENGTH: 21
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: JFINHA15TCM06A_2

<400> SEQUENCE: 362
gaugauaggu ugucggggug a                                              21

<210> SEQ ID NO 363
<211> LENGTH: 21
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: JFINHA15TCM06B_1

<400> SEQUENCE: 363
gatgauaggu ugucggggug a                                              21

<210> SEQ ID NO 364
<211> LENGTH: 21
<212> TYPE: DNA
<213> ORGANISM: Artificial Sequence
<220> FEATURE:
```

-continued

<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: JFINHA15TCM06B_2

<400> SEQUENCE: 364
gatgauaggu ugucggggug a                                           21

<210> SEQ ID NO 365
<211> LENGTH: 20
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: JFYINHA15TCM09A_1

<400> SEQUENCE: 365
augauagguu gucgggguga                                             20

<210> SEQ ID NO 366
<211> LENGTH: 20
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: JFINHA15TCM09A_1

<400> SEQUENCE: 366 augaagguu gucgggguga                                              20

<210> SEQ ID NO 367
<211> LENGTH: 20
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: JFINHA15TCM09B_1

<400> SEQUENCE: 367
atgauagguu gucgggguga                                             20

<210> SEQ ID NO 368
<211> LENGTH: 20
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: JFINHA15TCM09B_2

<400> SEQUENCE: 368
atgauagguu gucggggugu                                               20

<210> SEQ ID NO 369
<211> LENGTH: 18
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYINHAR15TCM01

<400> SEQUENCE: 369
ctatcatctc gccgcggc                                                 18

<210> SEQ ID NO 370
<211> LENGTH: 19
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYINHAR15TCM02

<400> SEQUENCE: 370
ctatcatctc gccgcggcc                                                19

<210> SEQ ID NO 371
<211> LENGTH: 20
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYINHAR15TCM03

<400> SEQUENCE: 371
ctatcatctc gccgcggccg                                               20

<210> SEQ ID NO 372
<211> LENGTH: 18
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYINHAR15TCM04

<400> SEQUENCE: 372
tatcatctcg ccgcggcc                                                 18

<210> SEQ ID NO 373
<211> LENGTH: 22
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYINHA8ACM01

<400> SEQUENCE: 373
taggatgtcg gggtgactgc ca                                            22

<210> SEQ ID NO 374
<211> LENGTH: 20
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYINHA8ACM02

<400> SEQUENCE: 374
taggatgtcg gggtgactgc                                              20

<210> SEQ ID NO 375
<211> LENGTH: 22
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYINHA8ACM03

<400> SEQUENCE: 375
gataggatgt cggggtgact gc                                           22

<210> SEQ ID NO 376
<211> LENGTH: 18
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: AYINHA8ACM04

<400> SEQUENCE: 376
uaggaugucg gggugacu                                                18

<210> SEQ ID NO 377
<211> LENGTH: 22
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYINHA8ACM05

<400> SEQUENCE: 377
taggatgtcg gggtgactgc ca                                           22

<210> SEQ ID NO 378
<211> LENGTH: 22
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYINHA8ACM06

<400> SEQUENCE: 378
taggatgtcg gggtgactgc ca                                           22

```
<210> SEQ ID NO 379
<211> LENGTH: 22
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYINHA8ACM07

<400> SEQUENCE: 379
taggatgtcg gggtgactgc ca                                              22

<210> SEQ ID NO 380
<211> LENGTH: 22
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYINHA8ACM08

<400> SEQUENCE: 380
taggatgtcg gggtgactgc ca                                              22

<210> SEQ ID NO 381
<211> LENGTH: 22
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: AYINHA8ACM08a

<400> SEQUENCE: 381
uaggaugucg gggugacugc ca                                              22

<210> SEQ ID NO 382
<211> LENGTH: 22
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: AYINHA8ACM08b

<400> SEQUENCE: 382
uaggaugucg gggugacugc ca                                              22

<210> SEQ ID NO 383
<211> LENGTH: 22
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYINHAR8ACM01

<400> SEQUENCE: 383
```
cgacatccta tcgtctcgcc gc             22

<210> SEQ ID NO 384
<211> LENGTH: 21
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYINHAR8ACM02

<400> SEQUENCE: 384
gacatcctat cgtctcgccg c             21

<210> SEQ ID NO 385
<211> LENGTH: 20
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYINHAR8ACM03

<400> SEQUENCE: 385
acatcctatc gtctcgccgc             20

<210> SEQ ID NO 386
<211> LENGTH: 19
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYINHAR8ACM04

<400> SEQUENCE: 386
catcctatcg tctcgccgc             19

<210> SEQ ID NO 387
<211> LENGTH: 20
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYINHAR8ACM05

<400> SEQUENCE: 387
cgacatccta tcgtctcgcc             20

<210> SEQ ID NO 388
<211> LENGTH: 21
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYINHAR8ACM02a

<400> SEQUENCE: 388
gacatcctat cgtctcgccg c             21

<210> SEQ ID NO 389

```
<211> LENGTH: 21
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYINHAR8ACM02b

<400> SEQUENCE: 389
gacatcctat cgtctcgccg c                                                   21

<210> SEQ ID NO 390
<211> LENGTH: 21
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYINHAR8ACM02c

<400> SEQUENCE: 390
gacatcctat cgtctcgccg c                                                   21

<210> SEQ ID NO 391
<211> LENGTH: 21
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYINHAR8ACM02d

<400> SEQUENCE: 391
gacatcctat cgtctcgccg c                                                   21

<210> SEQ ID NO 392
<211> LENGTH: 21
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: AYINHAR8ACM02e

<400> SEQUENCE: 392
gacatccuau cgucucgccg c                                                   21

<210> SEQ ID NO 393
<211> LENGTH: 21
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: AYINHAR8ACM02f

<400> SEQUENCE: 393
gacatccuau cgucucgccg c                                                   21
```

```
<210> SEQ ID NO 394
<211> LENGTH: 21
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: AYINHAR8ACM02g

<400> SEQUENCE: 394
gacatccuau cgucucgccg c                                            21

<210> SEQ ID NO 395
<211> LENGTH: 21
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: AYINHAR8ACM02h

<400> SEQUENCE: 395
gacatccuau cgucucgccg c                                            21

<210> SEQ ID NO 396
<211> LENGTH: 22
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: JFINHA8ACM08A_1

<400> SEQUENCE: 396
uaggaugucg gggugacugc ca                                           22

<210> SEQ ID NO 397
<211> LENGTH: 22
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: JFINHA8ACM08A_2

<400> SEQUENCE: 397
uaggaugucg gggugacugc ca                                           22

<210> SEQ ID NO 398
<211> LENGTH: 22
<212> TYPE: DNA
<213> ORGANISM: Artificial Sequence
<220> FEATURE:
<223> OTHER INFORMATION: Description of Artificial Sequence: Synthetic
```

```
        probe
<220> FEATURE:
<223> OTHER INFORMATION: Description of Combined DNA/RNA Molecule:
      Synthetic probe
<220> FEATURE:
<223> OTHER INFORMATION: JFINHA8ACM08B_1

<400> SEQUENCE: 398
uaggaugucg gggugacugc ca                                             22

<210> SEQ ID NO 399
<211> LENGTH: 22
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: JFINHA8ACM08B_2

<400> SEQUENCE: 399
uaggaugucg gggugacugc ca                                             22

<210> SEQ ID NO 400
<211> LENGTH: 20
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYINHA8ACM01

<400> SEQUENCE: 400
taggctgtcg gggtgactgc                                                20

<210> SEQ ID NO 401
<211> LENGTH: 20
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYINHA8ACM02

<400> SEQUENCE: 401
taggctgtcg gggtgactgc                                                20

<210> SEQ ID NO 402
<211> LENGTH: 22
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYINHA8ACM03

<400> SEQUENCE: 402
gataggctgt cggggtgact gc                                             22

<210> SEQ ID NO 403
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      probe
<220> FEATURE:
<223> OTHER INFORMATION: AYINHA8ACM04

<400> SEQUENCE: 403
ataggctgtc ggggtgactg c                                              21

<210> SEQ ID NO 404
<211> LENGTH: 19
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYINHA8ACM05

<400> SEQUENCE: 404
aggctgtcgg ggtgactgc                                                 19

<210> SEQ ID NO 405
<211> LENGTH: 22
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYINHAR8CCM01

<400> SEQUENCE: 405
cgacagccta tcgtctcgcc gc                                             22

<210> SEQ ID NO 406
<211> LENGTH: 21
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYINHAR8CCM02

<400> SEQUENCE: 406
gacagcctat cgtctcgccg c                                              21

<210> SEQ ID NO 407
<211> LENGTH: 20
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYINHAR8CCM03

<400> SEQUENCE: 407
acagcctatc gtctcgccgc                                                20

<210> SEQ ID NO 408
<211> LENGTH: 19
<212> TYPE: DNA
<213> ORGANISM: Artificial Sequence
<220> FEATURE:
<223> OTHER INFORMATION: Description of Artificial Sequence: Synthetic
      probe
<220> FEATURE:
```

<223> OTHER INFORMATION: AYINHAR8CCM04

<400> SEQUENCE: 408
cagcctatcg tctcgccgc                                                    19

<210> SEQ ID NO 409
<211> LENGTH: 20
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: AYINHAR8CCM05

<400> SEQUENCE: 409
cgacagccta tcgtctcgcc                                                   20

<210> SEQ ID NO 410
<211> LENGTH: 18
<212> TYPE: DNA
<213> ORGANISM: Artificial Sequence
<220> FEATURE:
<223> OTHER INFORMATION: Description of Artificial Sequence: Synthetic
      forward primer
<220> FEATURE:
<223> OTHER INFORMATION: AYKATG003

<400> SEQUENCE: 410
gcggtcacac tttcggta                                                     18

<210> SEQ ID NO 411
<211> LENGTH: 16
<212> TYPE: DNA
<213> ORGANISM: Artificial Sequence
<220> FEATURE:
<223> OTHER INFORMATION: Description of Artificial Sequence: Synthetic
      reverse primer
<220> FEATURE:
<223> OTHER INFORMATION: AYKATG002

<400> SEQUENCE: 411
cttggcggtg tattgc                                                       16

<210> SEQ ID NO 412
<211> LENGTH: 20
<212> TYPE: DNA
<213> ORGANISM: Artificial Sequence
<220> FEATURE:
<223> OTHER INFORMATION: Description of Artificial Sequence: Synthetic
      forward primer
<220> FEATURE:
<223> OTHER INFORMATION: AYINHA001

<400> SEQUENCE: 412
gaagtgtgct gagtcacacc                                                   20

<210> SEQ ID NO 413
<211> LENGTH: 18
<212> TYPE: DNA
<213> ORGANISM: Artificial Sequence
<220> FEATURE:
<223> OTHER INFORMATION: Description of Artificial Sequence: Synthetic
      reverse primer
<220> FEATURE:
<223> OTHER INFORMATION: AYINHA002

<400> SEQUENCE: 413

```
ggactgaacg ggatacga                                                   18

<210> SEQ ID NO 414
<211> LENGTH: 266
<212> TYPE: DNA
<213> ORGANISM: Mycobacterium tuberculosis
<220> FEATURE:
<223> OTHER INFORMATION: katG WT amplicon

<400> SEQUENCE: 414
gcggtcacac tttcggtaag acccatggcg ccggcccggc cgatctggtc ggccccgaac     60
ccgaggctgc tccgctggag cagatgggct gggctggaa gagctcgtat ggcaccggaa     120
ccggtaagga cgcgatcacc agcggcatcg aggtcgtatg gacgaacacc ccgacgaaat    180
gggacaacag tttcctcgag atcctgtacg gctacgagtg ggagctgacg aagagccctg   240
ctggcgcttg gcaatacacc gccaag                                         266

<210> SEQ ID NO 415
<211> LENGTH: 191
<212> TYPE: DNA
<213> ORGANISM: Mycobacterium tuberculosis
<220> FEATURE:
<223> OTHER INFORMATION: inhA WT amplicon

<400> SEQUENCE: 415
gaagtgtgct gagtcacacc gacaaacgtc acgagcgtaa ccccagtgcg aaagttcccg    60
ccggaaatcg cagccacgtt acgctcgtgg acataccgat ttcggcccgg ccgcggcgag   120
acgataggtt gtcggggtga ctgccacagc cactgaaggg gccaaacccc cattcgtatc   180
ccgttcagtc c                                                         191

<210> SEQ ID NO 416
<211> LENGTH: 184
<212> TYPE: DNA
<213> ORGANISM: Mycobacterium tuberculosis
<220> FEATURE:
<223> OTHER INFORMATION: RIF WT amplicon

<400> SEQUENCE: 416
ggacgtggag gcgatcacac cgcagacgtt gatcaacatc cggccggtgg tcgccgcgat    60
caaggagttc ttcggcacca gccagctgag ccaattcatg gaccgaaaca acccgctgtc   120
ggggttgacc cacaagcgcc gactgtcggc gctggggccc ggcggtctgt cacgtgagcg   180
tgcc                                                                 184

<210> SEQ ID NO 417
<211> LENGTH: 184
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: RIF MT03 amplicon

<400> SEQUENCE: 417
ggacgtggag gcgatcacac cgcagacgtt gatcaacatc cggccggtgg tcgccgcgat    60
caaggagttc ttcggcacca gccagccgag ccaattcatg gaccagaaca acccgctgtc   120
ggggttgacc gacaagcgcc gactgtcggc gcctggggccc ggcggtctgt cacgtgagcg   180
tgcc                                                                 184
```

<210> SEQ ID NO 418
<211> LENGTH: 184
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: RIF MT04 amplicon

<400> SEQUENCE: 418
ggacgtggag gcgatcacac cgcagacgtt gatcaacatc cggccggtgg tcgccgcgat    60
caaggagttc ttcggcagca gccagctgag ccaattcatg gtccagaaca acccgctgtc   120
ggggttgacc aacaagcgcc gactgtcggc gctggggtcc ggcggtctgt cacgtgagcg   180
tgcc                                                                184

<210> SEQ ID NO 419
<211> LENGTH: 184
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: RIF MT05 amplicon

<400> SEQUENCE: 419
ggacgtggag gcgatcacac cgcagacgtt gatcaacatc cggccggtgg tcgccgcgat    60
caaggagttc ttcggcgcca gccagctgag ccaattcatg taccagaaca acccgctgtc   120
ggggttgacc cgcaagcgcc gactgtcggc gctggggcac ggcggtctgt cacgtgagcg   180
tgcc                                                                184

<210> SEQ ID NO 420
<211> LENGTH: 184
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: RIF MT06 amplicon

<400> SEQUENCE: 420
ggacgtggag gcgatcacac cgcagacgtt gatcaacatc cggccggtgg tcgccgcgat    60
caaggagttc ttcggcccca gccagctgag ccaattcatg gaccagaaca acccgctgtc   120
ggggttgacc tacaagcgcc gactgtcggc gccggggccc ggcggtctgt cacgtgagcg   180
tgcc                                                                184

<210> SEQ ID NO 421
<211> LENGTH: 184
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: RIF MT07 amplicon

<400> SEQUENCE: 421
ggacgtggag gcgatcacac cgcagacgtt gatcaacatc cggccggtgg tcgccgcgat    60
caaggagttc ttcggcacca gccagcggag ccaattcatg gaccagaaca acccgctgtc   120

```
ggggttgacc ctcaagcgcc gactgtcggc gctggggccc ggcggtccgt cacgtgagcg    180
tgcc                                                                 184
```

<210> SEQ ID NO 422
<211> LENGTH: 184
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: RIF MT08 amplicon

<400> SEQUENCE: 422

```
ggacgtggag gcgatcacac cgcagacgtt gatcaacatc cggccggtgg tcgccgcgat    60
caaggagttc ttcggcacca gccagctgag cctattcatg gaccagaaca cccgctgca    120 ggggttgacc cacaagcgcc gactgttggc gctggggccc ggcggtctgt cacgtgagcg    180
tgcc                                                                 184
```

<210> SEQ ID NO 423
<211> LENGTH: 184
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: RIF MT09 amplicon

<400> SEQUENCE: 423

```
ggacgtggag gcgatcacac cgcatacgtt gatcaacatc cggccggtgg tcgccgcgat    60
caaggagtcc ttcggcacca gccagctgag caaattcatg gaccagaaca cccgctgtt    120 ggggttgacc cacaagcgcc gactgtgggc gctggggccc ggcggtctgt cacgtgagcg    180
tgcc                                                                 184
```

<210> SEQ ID NO 424
<211> LENGTH: 184
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: RIF MT10 amplicon

<400> SEQUENCE: 424

```
ggacgtggag gcgatcacac cgcagacgtt gatcaacatc cggccggtgg tcgccgcgat    60
caaggagtta ttcggcacca gccagctgag cccattcatg gaccagaaca cccgctgtg    120 ggggttgacc cacaagcgcc gactgtttgc gctggggccc ggcggtctgt cacgtgagcg    180
tgcc                                                                 184
```

<210> SEQ ID NO 425
<211> LENGTH: 191
<212> TYPE: DNA
<213> ORGANISM: Mycobacterium tuberculosis
<220> FEATURE:
<223> OTHER INFORMATION: WT_INHA amplicon

<400> SEQUENCE: 425

```
gaagtgtgct gagtcacacc gacaaacgtc acgagcgtaa ccccagtgcg aaagttcccg    60
```

```
ccggaaatcg cagccacgtt acgctcgtgg acataccgat ttcggcccgg ccgcggcgag    120
acgataggtt gtcggggtga ctgccacagc cactgaaggg gccaaacccc cattcgtatc    180
ccgttcagtc c                                                        191

<210> SEQ ID NO 426
<211> LENGTH: 191
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: MT_INHA02 amplicon

<400> SEQUENCE: 426
gaagtgtgct gagtcacacc gacaaacgtc acgagcgtaa ccccagtgcg aaagttcccg     60
ccggaaatcg cagccacgtt acgctcgtgg acataccgat ttcggcccgg ccgcggcgag    120
atgataggtt gtcggggtga ctgccacagc cactgaaggg gccaaacccc cattcgtatc    180
ccgttcagtc c                                                        191

<210> SEQ ID NO 427
<211> LENGTH: 191
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: MT_INHA03 amplicon

<400> SEQUENCE: 427
gaagtgtgct gagtcacacc gacaaacgtc acgagcgtaa ccccagtgcg aaagttcccg     60
ccggaaatcg cagccacgtt acgctcgtgg acataccgat ttcggcccgg ccgcggcgag    120
acgataggta gtcggggtga ctgccacagc cactgaaggg gccaaacccc cattcgtatc    180
ccgttcagtc c                                                        191

<210> SEQ ID NO 428
<211> LENGTH: 191
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: MT_INHA04 amplicon

<400> SEQUENCE: 428
gaagtgtgct gagtcacacc gacaaacgtc acgagcgtaa ccccagtgcg aaagttcccg     60
ccggaaatcg cagccacgtt acgctcgtgg acataccgat ttcggcccgg ccgcggcgag    120
acgataggtc gtcggggtga ctgccacagc cactgaaggg gccaaacccc cattcgtatc    180
ccgttcagtc c                                                        191

<210> SEQ ID NO 429
<211> LENGTH: 266
<212> TYPE: DNA
<213> ORGANISM: Mycobacterium tuberculosis
<220> FEATURE:
<223> OTHER INFORMATION: WT_KATG01 amplicon

<400> SEQUENCE: 429
```

```
gcggtcacac tttcggtaag acccatggcg ccggcccggc cgatctggtc ggccccgaac      60
ccgaggctgc tccgctggag cagatgggct tgggctggaa gagctcgtat ggcaccggaa     120
ccggtaagga cgcgatcacc agcggcatcg aggtcgtatg gacgaacacc ccgacgaaat     180
gggacaacag tttcctcgag atcctgtacg gctacgagtg ggagctgacg aagagccctg     240
ctggcgcttg gcaataccac gccaag                                         266
```

```
<210> SEQ ID NO 430
<211> LENGTH: 266
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: MT_KATG02 amplicon

<400> SEQUENCE: 430
gcggtcacac tttcggtaag acccatggcg ccggcccggc cgatctggtc ggccccgaac      60
ccgaggctgc tccgctggag cagatgggct tgggctggaa gagctcgtat ggcaccggaa     120
ccggtaagga cgcgatcacc atcggcatcg aggtcgtatg gacgaacacc ccgacgaaat     180
gggacaacag tttcctcgag atcctgtacg gctacgagtg ggagctgacg aagagccctg     240
ctggcgcttg gcaataccac gccaag                                         266
```

```
<210> SEQ ID NO 431
<211> LENGTH: 266
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: MT_KATG03 amplicon

<400> SEQUENCE: 431
gcggtcacac tttcggtaag acccatggcg ccggcccggc cgatctggtc ggccccgaac      60
ccgaggctgc tccgctggag cagatgggct tgggctggaa gagctcgtat ggcaccggaa     120
ccggtaagga cgcgatcacc aacggcatcg aggtcgtatg gacgaacacc ccgacgaaat     180
gggacaacag tttcctcgag atcctgtacg gctacgagtg ggagctgacg aagagccctg     240
ctggcgcttg gcaataccac gccaag                                         266
```

```
<210> SEQ ID NO 432
<211> LENGTH: 266
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: MT_KATG04 amplicon

<400> SEQUENCE: 432
gcggtcacac tttcggtaag acccatggcg ccggcccggc cgatctggtc ggccccgaac      60
ccgaggctgc tccgctggag cagatgggct tgggctggaa gagctcgtat ggcaccggaa     120
ccggtaagga cgcgatcacc accggcatcg aggtcgtatg gacgaacacc ccgacgaaat     180
gggacaacag tttcctcgag atcctgtacg gctacgagtg ggagctgacg aagagccctg     240
ctggcgcttg gcaataccac gccaag                                         266
```

```
<210> SEQ ID NO 433
<211> LENGTH: 266
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: MT_KATG05 amplicon

<400> SEQUENCE: 433
gcggtcacac tttcggtaag acccatggcg ccggcccggc cgatctggtc ggccccgaac      60
ccgaggctgc tccgctggag cagatgggct tgggctggaa gagctcgtat ggcaccggaa     120
ccggtaagga cgcgatcacc acaggcatcg aggtcgtatg gacgaacacc ccgacgaaat     180
gggacaacag tttcctcgag atcctgtacg gctacgagtg ggagctgacg aagagccctg     240
ctggcgcttg gcaatacacc gccaag                                          266
```

COMPOSITIONS AND METHODS FOR DETECTION OF DRUG RESISTANT *MYCOBACTERIUM TUBERCULOSIS*

This application is a divisional of U.S. patent application Ser. No. 14/575,879, filed on Dec. 18, 2014, the content of which is incorporated by reference herein in its entirety.

SEQUENCE LISTING

The instant application contains a Sequence Listing which has been filed electronically in ASCII format and is hereby incorporated by reference in its entirety. Said ASCII copy, created on Dec. 17, 2014, is named 32319_US_SL.txt and is 138,013 bytes in size.

FIELD OF THE INVENTION

The present invention relates to the field of virus diagnostic, and more particularly, to PCR detection methods utilizing hydrolysis probes for detection of drug resistant *Mycobacterium tuberculosis*.

BACKGROUND OF THE INVENTION

Tuberculosis (TB) is a bacterial disease caused by various strains of mycobacteria, such as *Mycobacterium tuberculosis* (MTB) most often found in the lungs. It is transmitted from person to person through the air when individuals with pulmonary or laryngeal tuberculosis, cough, sneeze, or spit, and propel MTB into the air. It is estimated that one-third of the world population is infected with MTB and 9 million people develop TB each year. TB continues to be a leading cause of human infectious disease and drug-resistant strains of MTB are on the rise, especially in developing countries.

Two common first-line drugs for the treatment of MTB include isoniazid (INH) and rifampicin (RIF), and patients can acquire drug resistant MTB from living in or visiting a place where drug resistance is prevalent. Patients can also develop drug resistant MTB when their antibiotic treatment regimen is interrupted. Culturing on solid or liquid media is still considered the gold standard for MTB and MTB drug resistance detection, but culturing can take up to eight weeks for results. Many commercial nucleic acid tests for MTB drug resistance have a very fast turn-around time, but cannot detect a population with a small percentage of mutant species in a mixed infection containing both wild type and mutant species. Thus there is a need in the art for a quick and reliable method to specifically detect MTB resistant to rifampicin (MTB-RIF) and/or MTB resistant to isoniazid (MTB-INH) in a sensitive manner.

SUMMARY OF THE INVENTION

Embodiments described herein relate to methods for the rapid detection of the presence or absence of MTB-RIF and/or MTB-INH in a biological or non-biological sample, for example, multiplex detection of MTB-RIF and/or MTB-INH by real-time polymerase chain reaction in a single test tube. Embodiments include methods of detection of MTB-RIF and/or MTB-INH comprising performing at least one cycling step, which may include an amplifying step and a hybridizing step. Furthermore, embodiments include primers, probes, and kits that are designed for the detection of single MTB-RIF or MTB-INH, or MTB-RIF and MTB-INH co-infections in a single tube. The detection methods are designed to specifically identify single polymorphism (SNP) in target MTB genes for rpoB (beta subunit prokaryotic RNA polymerase), inhA (enoyl-acyl carrier protein reductase), and katG (catalase-peroxidase) simultaneously, which allows detection and differentiation of MTB-RIF and/or MTB-INH infections in a singlet test. For example, there are 17 SNPs in the rboB gene which confer resistance to rifampicin in MTB which include rpoB 531L, rpoB 531W, rpoB 526L, rpoB 526Y, rpoB 526D, rpoB 526N, rpoB 513L, rpoB 513K, rpoB 513P, rpoB 522L, rpoB 522Q, rpoB 522W, rpoB 516V, rpoB 516Y, rpoB 533P, rpoB 511P, and rpoB 526R; there are 3 SNPs in the inhA gene which confer resistance to isoniazid in MTB which include inhA-15T, inhA-8A, and inhA-8C; and there are 4 SNPs in the katG gene which also confer resistance to isoniazid in MTB which include katG 315I, katG 315N, katG 315T, and katG 315T2.

In one embodiment, a method of detecting MTB-RIF and/or MTB-INH in a sample is provided, including performing an amplifying step comprising contacting the sample with at least a set of rpoB primers, a set of inhA primers, and a set of katG primers to produce one or more amplification products if any rpoB, inhA, and katG target nucleic acid is present in the sample; performing a hybridizing step comprising contacting said one or more amplification products with a plurality of detectable rpoB probes, a plurality of detectable inhA probes, and a plurality of detectable katG probes, including: 17 rpoB probes for detection of one or more of 17 single nucleotide polymorphisms SNPs which confer rifampicin resistance to MTB; 3 inhA probes for detection of one or more of 3 SNPs which confer isoniazid resistance to MTB; and 4 katG probes for detection of one or more of 4 SNPs which confer isoniazid resistance to MTB; and detecting the presence or absence of said one or more amplification products, wherein the presence of said one or more amplification products is indicative of the presence of MTB-RIF and/or MTB-INH in the sample and wherein the absence of said one or more amplification products is indicative of the absence of MTB-RIF and/or MTB-INH in the sample; wherein said plurality of rpoB probes comprise hydrolysis probes for detection of each of the 17 SNPs which confer rifampicin resistance to MTB, comprising rpoB 531L, rpoB 531W, rpoB 526L, rpoB 526Y, rpoB 526D, rpoB 526N, rpoB 513L, rpoB 513K, rpoB 513P, rpoB 522L, rpoB 522Q, rpoB 522W, rpoB 516V, rpoB 516Y, rpoB 533P, rpoB 511P, and rpoB 526R; wherein said plurality of inhA probes comprise hydrolysis probes for detection of each of the 3 SNPs which confer isoniazid resistance to MTB, comprising inhA-15T, inhA-8A, and inhA-8C; and wherein said plurality of katG probes comprise hydrolysis probes for detection of each of the 4 SNPs which confer isoniazid resistance to MTB, comprising katG 315I, katG 315N, katG 315T, and katG 315T2.

Another embodiment provides an oligonucleotide comprising or consisting of a sequence of nucleotides selected from SEQ ID NOs: 1 through 409, or a complement thereof, which oligonucleotide has 100 or fewer nucleotides. In another aspect, the present disclosure provides an oligonucleotide that includes a nucleic acid having at least 70% sequence identity (e.g., at least 75%, 80%, 85%, 90% or 95%, etc.) to one of SEQ ID NOs: 1 through 409, or a complement thereof, which oligonucleotide has 100 or fewer nucleotides. Generally, these oligonucleotides may be primer nucleic acids, probe nucleic acids, or the like in these embodiments. In certain of these embodiments, the oligonucleotides have 40 or fewer nucleotides (e.g. 35 or fewer nucleotides, 30 or fewer nucleotides, etc.) In some embodiments, the oligonucleotides comprise at least one modified nucleotide, e.g. to alter nucleic acid hybridization stability relative to unmodified nucleotides. Optionally, the oligonucleotides comprise at least one label and/or at least one quencher moiety. In some embodiments, the oligonucleotides include at least one conservatively modified variation. "Conservatively modified variations" or, simply, "conservative variations" of a particular nucleic acid sequence refers to those nucleic acids, which encode identical or essentially identical amino acid sequences, or, where the nucleic acid does not encode an amino acid sequence, to essentially identical sequences. One of skill will recognize that individual substitutions, deletions or additions which alter, add or delete a single amino acid or a small percentage of amino acids (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid.

In one aspect, amplification can employ a polymerase enzyme having 5' to 3' nuclease activity. Thus, the first and second fluorescent moieties may be within no more than 8 nucleotides of each other along the length of the probe.

In a further embodiment, a kit for detecting one or more nucleic acids of MTB-RIF and/or MTB-INH is provided. The kit can include a plurality of sets of rpoB, inhA, and katG primers specific for amplification of a rpoB, inhA, and katG gene targets; and a plurality of detectable rpoB, inhA, and katG probes specific for detection of a rpoB, inhA, and katG amplification products.

In one aspect, the kit can include probes already labeled with donor and corresponding acceptor fluorescent moieties, or can include fluorophoric moieties for labeling the probes. The kit can also include nucleoside triphosphates, nucleic acid polymerase, and buffers necessary for the function of the nucleic acid polymerase. The kit can also include a package insert and instructions for using the primers, probes, and fluorophoric moieties to detect the presence or absence of MTB-RIF and/or MTB-INH in a sample.

Unless otherwise defined, all technical and scientific terms used herein have the same meaning as commonly understood by one of ordinary skill in the art to which this invention belongs. Although methods and materials similar or equivalent to those described herein can be used in the practice or testing of the present subject matter, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments are set forth in the accompanying drawings and the description below. Other features, objects, and advantages will be apparent from the drawings and detailed description, and from the claims.

BRIEF DESCRIPTION OF THE FIGURES

FIGS. 2A and 2B show wild type and mutant amplicon sequences for the inhA gene target and indication each of the 3 SNPs which confer isoniazid resistance to MTB.

Figure 3A:
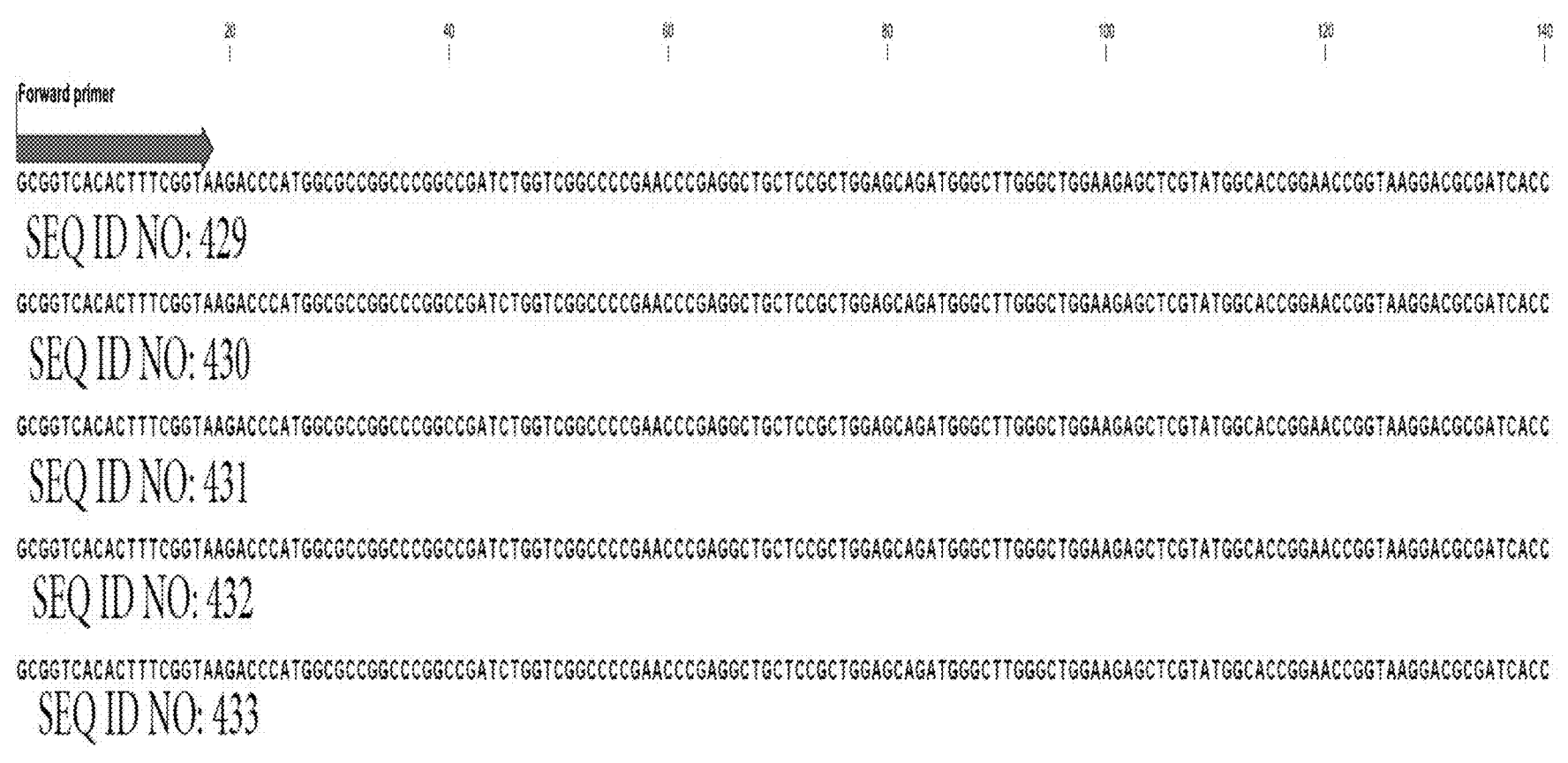

FIGS. 3A and 3B show wild type and mutant amplicon sequences for the katG gene target and indication each of the 4 SNPs which confer isoniazid resistance to MTB.

DETAILED DESCRIPTION OF THE INVENTION

Figure 1A:
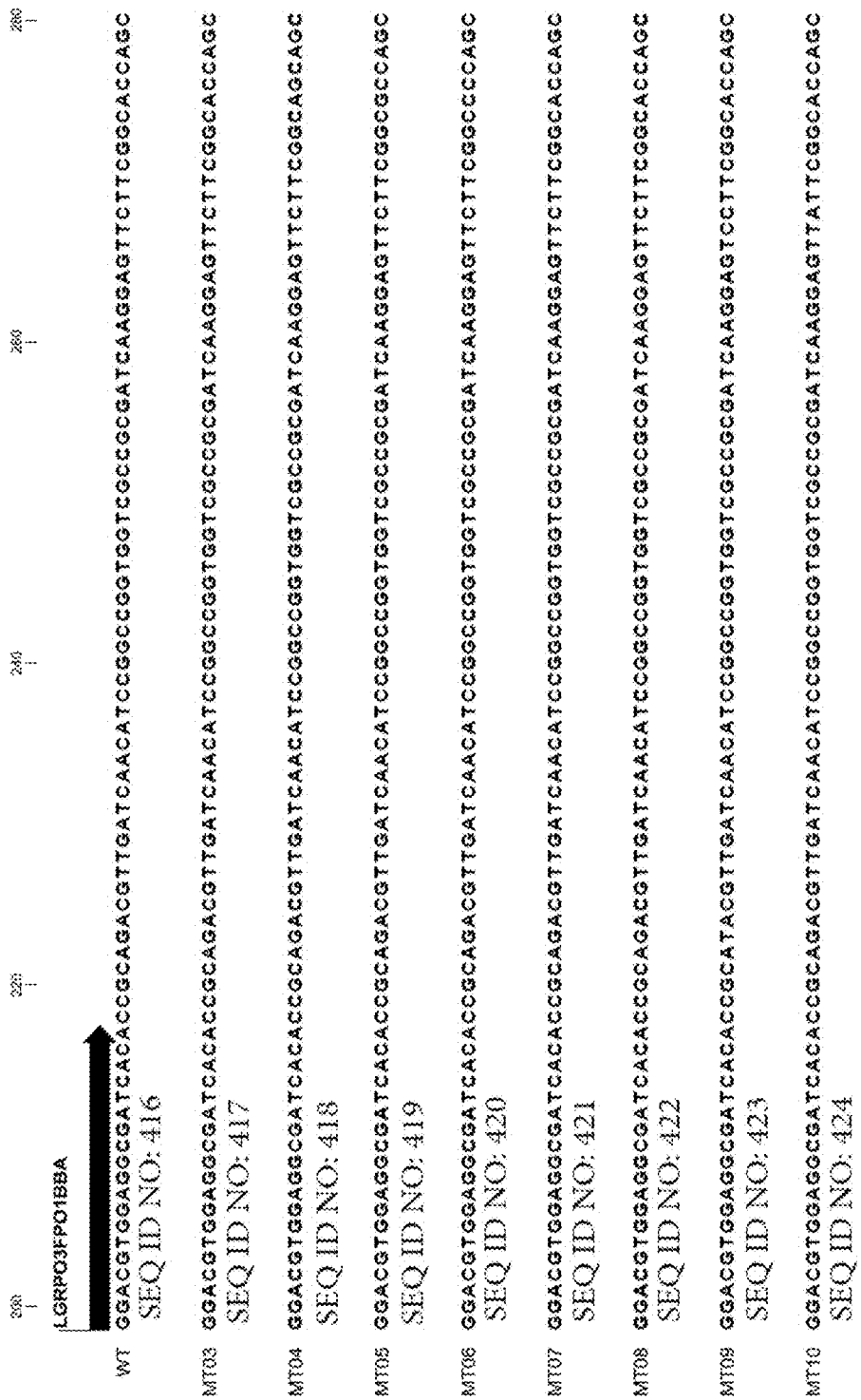
FIGS. 1A and 1B show wild type and mutant amplicon sequences for the rpoB gene target and indication each of the 17 SNPs which confer rifampicin resistance to MTB.
Figure 1B:
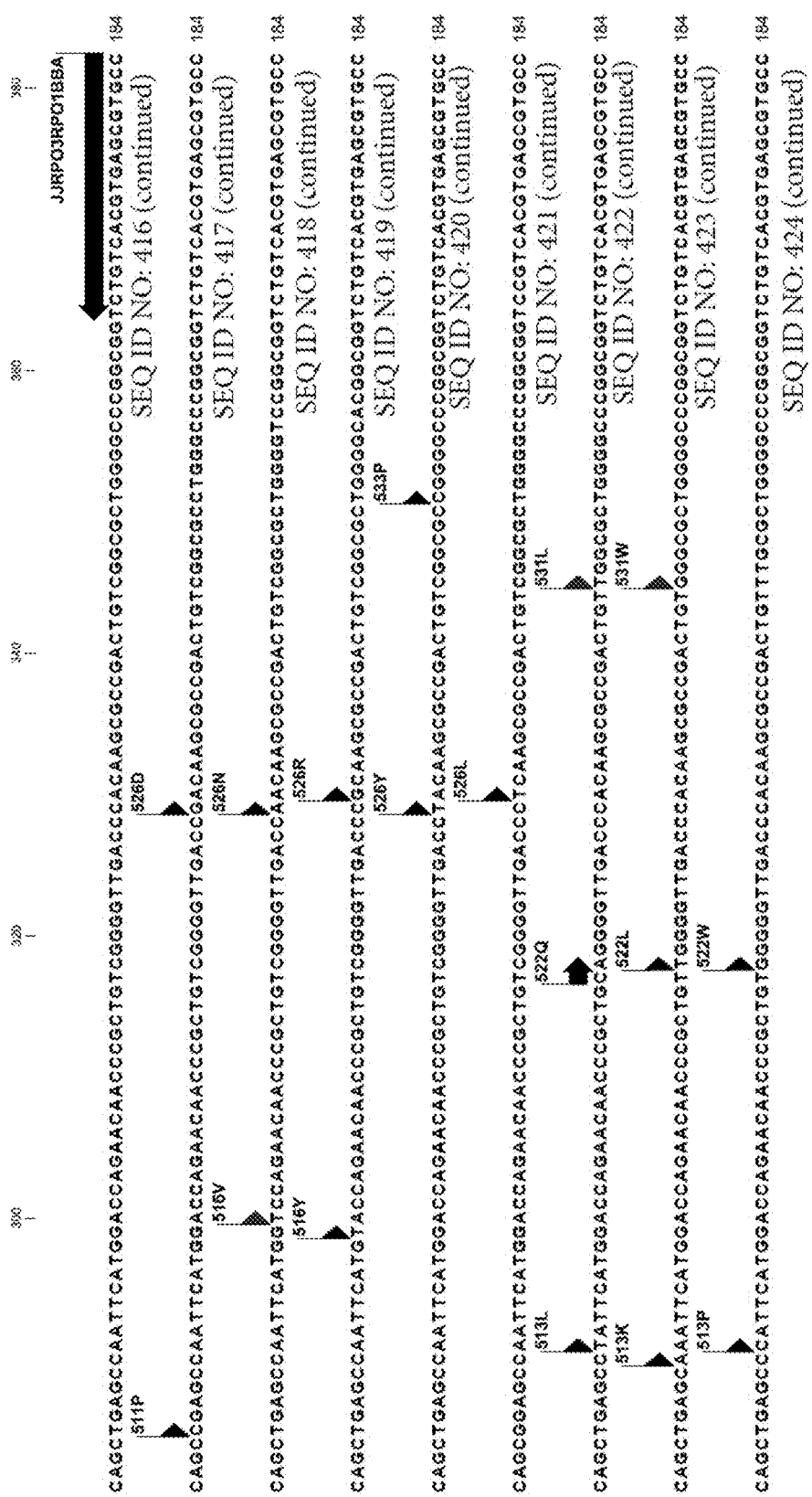
Figure 2A:
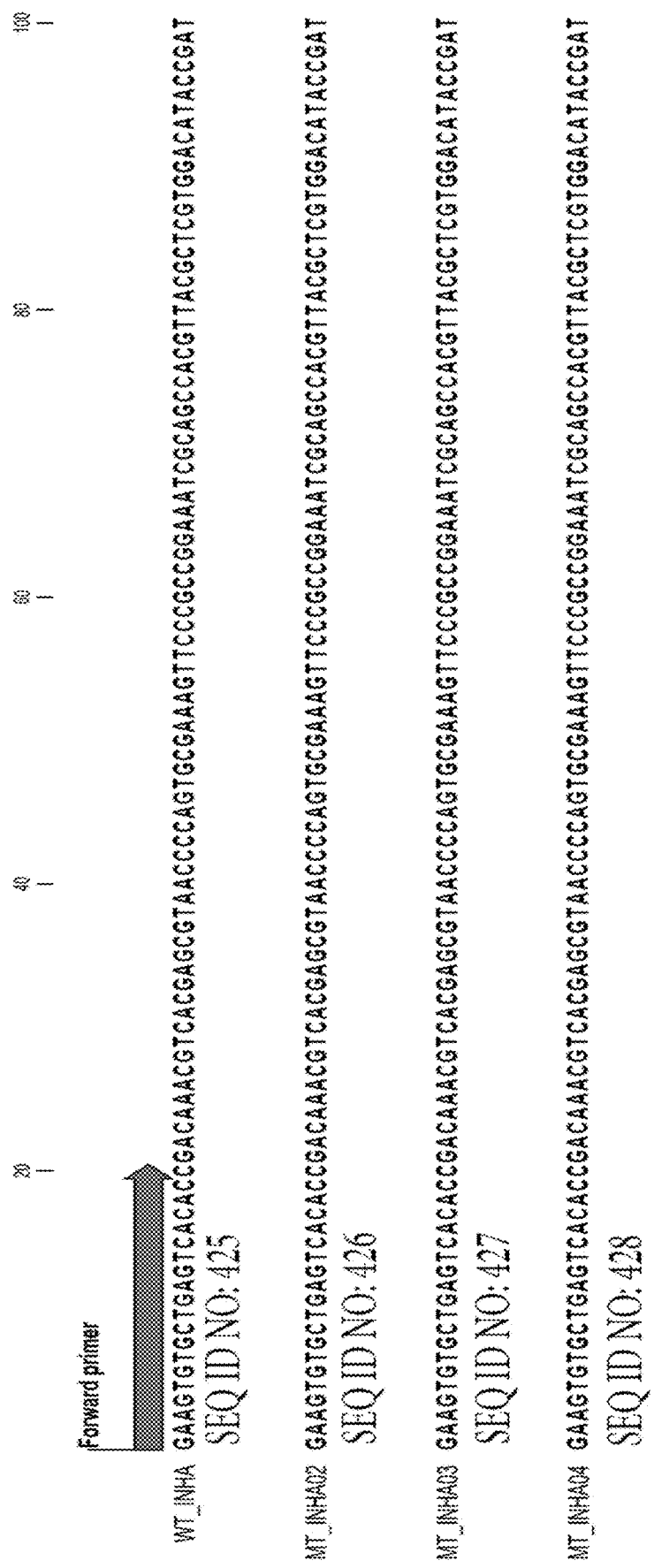
Figure 4A:
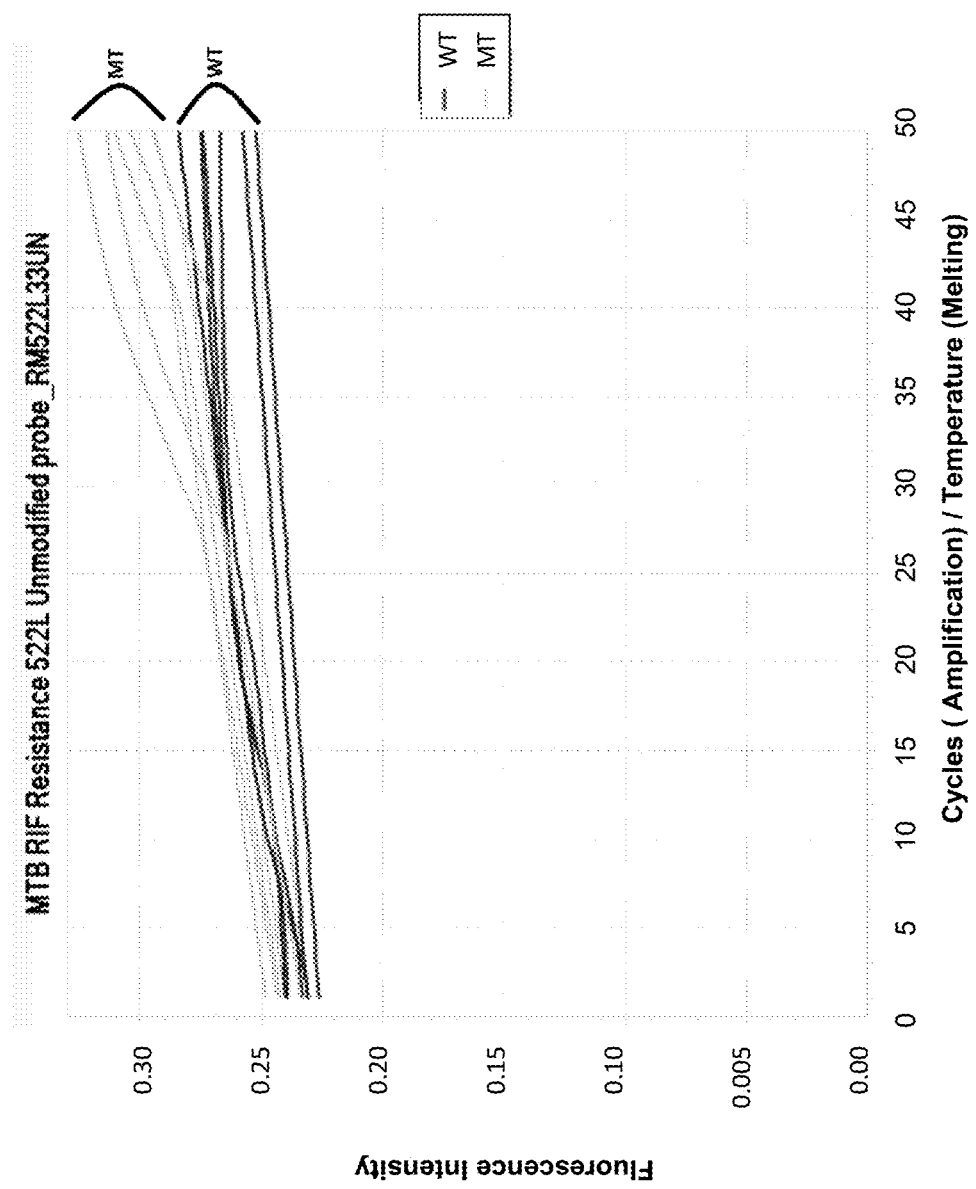
FIGS. 4 and 4B show growth curve assay for singleplex PCR SNP-specific probe detection using unmodified probe for 522L SNP compared to using modified probe for 522L SNP (MT target(~1 e6, 1 e2, 1 e3 10c/PCR) compared with WT).
Figure 4B:
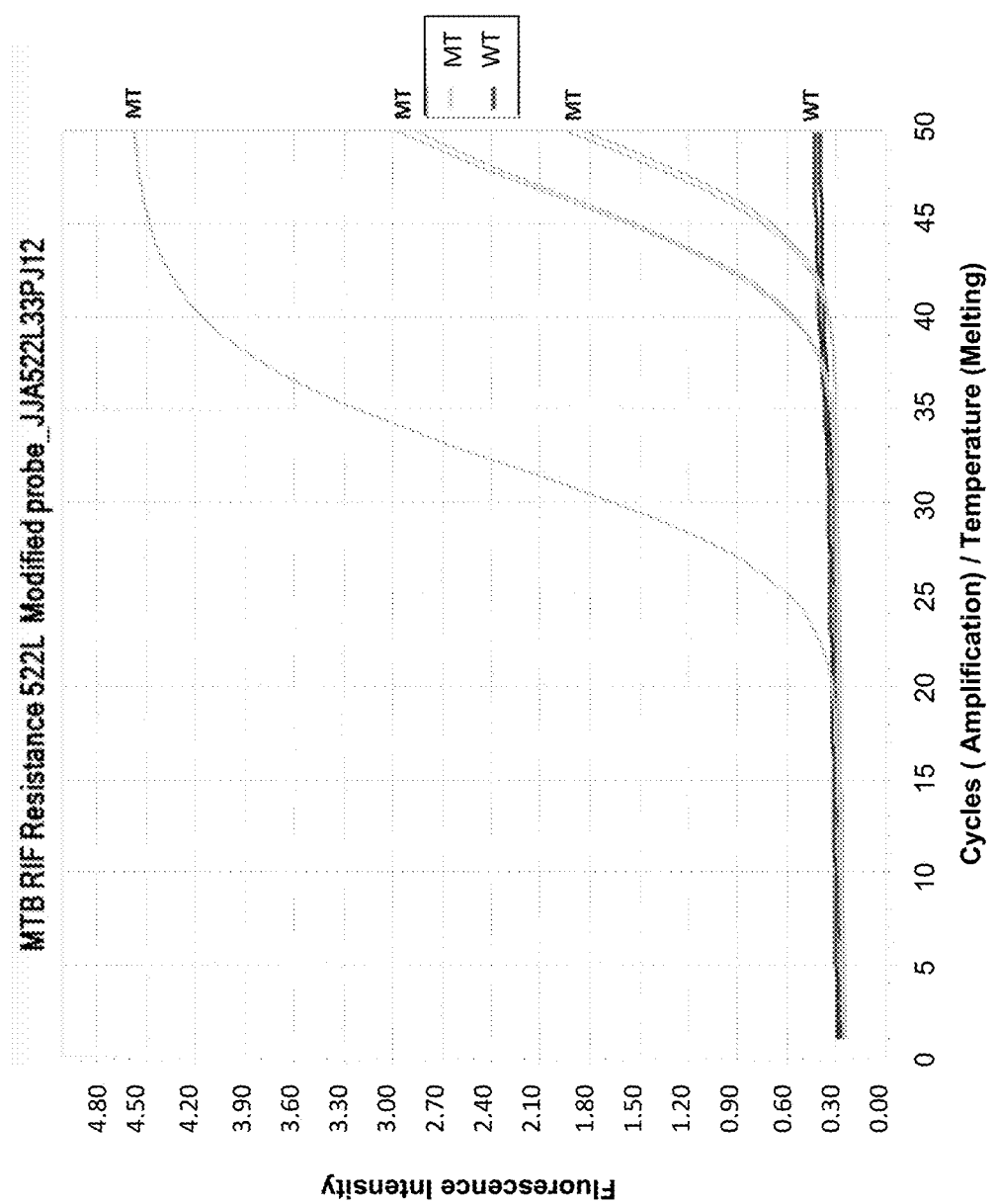

Diagnosis of MTB-RIF and/or MTB-INH infections by nucleic acid amplification provides a method for rapidly and accurately detecting MTB-RIF and/or MTB-INH infections. A real-time assay for detecting MTB-RIF and/or MTB-INH in a sample is described herein. Primers and probes for detecting the rpoB, inhA, and katG target nucleic acids of MTB-RIF and/or MTB-INH are provided, as are articles of manufacture or kits containing such primers and probes. The increased sensitivity of real-time PCR for detection of MTB-RIF and/or MTB-INH compared to other methods, as well as the improved features of real-time PCR including sample containment and real-time detection of the amplified product, make feasible the implementation of this technology for routine diagnosis of MTB-RIF and/or MTB-INH infections in the clinical laboratory.

Identification of drug resistant MTB requires detection of numerous single nucleotide polymorphisms (SNPs) in the MTB genome located on several different genes. Using a novel variation of hydrolysis probe (also known as TaqMan probe) design, a multiplex of highly discriminating TaqMan probes were created, wherein each TaqMan probe can detect a single SNP without cross reactivity. The probes are designed to be very short and highly stabilized in order to bind and cleave with great specificity only to a perfectly matched drug resistant (mutant) sequence.

The present disclosure provides Taqman probes for detection of the various SNPs which confer resistance to MTB-RIF and MTB-INH. TaqMan compatible probes are not generally able to detect single base pair mismatches. Generally, TaqMan probes are designed to be much longer, and have a significantly higher melting temperature than the associated PCR primers in order to ensure adequate probe binding to the target sequence prior to the primers and attain maximum probe cleavage during PCR. Due to the high melting temperature and length of such probes, they are generally very tolerant of a single base mismatch under the probe region and thus do not discriminate between two targets that differ by only a single base. In the present disclosures, the hydrolysis TaqMan probes are able to successfully detect only drug resistant MTB and not cross react with drug sensitive MTB, which can only differ by a single base. The present disclosure provides numerous short, highly modified probes that can detect a single base pair mismatch under the probe region. The modified bases that can be substituted in the probe designs include propynyl-dC, t-butyl-benzyl dC, propynyl-dU, G-clamps, methyl-dC, N6-methl dA, and 7-deaza-dG. In designing the probes, the present inventors strategically placed several modified base pairs within the probe sequences in order to maximize the discrimination ability of the probe. It was discovered that some modifications work better than others, and that the discrimination ability is affected by the placement of the modifications in the probe.

The present disclosure provide methods and kits for multiplexed assays which can utilize a plurality of highly modified TaqMan probes wherein each probe can detect a single SNP known to confer Rrifampicin (RIF) and Isoniazid (INH) drug resistance in the MTB genome without significantly cross reacting with drug sensitive (wild type) MTB. The unique ability of the disclosed TaqMan probes to detect mutant SNPs without significant WT cross reactivity enables the assay to detect a minor presence of drug resistant MTB when mixed in a background of wild type (WT). The presence of mixed infection has been reported, and it has been suggested that the prevalence of mixed infection is underreported due to the inability of current commercial assays to detect drug resistant MTB in the presence of drug sensitive MTB. It is reported by the Center for Disease Control (CDC) that a patient that is infected with as little as 1% drug resistant MTB in a background of WT may fail their proposed treatment regimen.

The methods may include performing at least one cycling step that includes amplifying one or more portions of rpoB, inhA, and katG nucleic acid molecule gene targets from a sample using a plurality of pairs of primers, including rpoB, inhA, and katG specific primers as used herein refer to oligonucleotide primers that specifically anneal to nucleic acid sequences encoding rpoB, inhA, and katG, respectively, and initiate synthesis therefrom under appropriate conditions. Each of the discussed rpoB, inhA, and katG primers anneals to a target within or adjacent to the respective rpoB, inhA, and katG target nucleic acid molecule such that at least a portion of each amplification product contains nucleic acid sequence corresponding to respective target. The one or more of rpoB, inhA, and katG amplification products are produced provided that one or more of rpoB, inhA, and katG nucleic acid is present in the sample, thus the presence of the one or more of rpoB, inhA, and katG amplification products is indicative of the presence of rpoB, inhA, and katG in the sample. The amplification product should contain the nucleic acid sequences that are complementary to one or more detectable probes for detection of the SNPs in rpoB, inhA, and katG which confer rifampicin and/or isoniazid resistance to MTB. Each cycling step includes an amplification step, a hybridization step, and a detection step, in which the sample is contacted with the one or more detectable probes for rpoB, inhA, and katG for detection of the presence or absence of MTB-RIF and/or MTB-INH in the sample.

As used herein, the term "amplifying" refers to the process of synthesizing nucleic acid molecules that are complementary to one or both strands of a template nucleic acid molecule (e.g., rpoB, inhA, and katG nucleic acid molecules). Amplifying a nucleic acid molecule typically includes denaturing the template nucleic acid, annealing primers to the template nucleic acid at a temperature that is below the melting temperatures of the primers, and enzymatically elongating from the primers to generate an amplification product. Amplification typically requires the presence of deoxyribonucleoside triphosphates, a DNA polymerase enzyme (e.g., Platinum® Taq) and an appropriate buffer and/or co-factors for optimal activity of the polymerase enzyme (e.g., $MgCl_2$ and/or KCl).

The term "primer" is used herein as known to those skilled in the art and refers to oligomeric compounds, primarily to oligonucleotides but also to modified oligonucleotides that are able to "prime" DNA synthesis by a template-dependent DNA polymerase, i.e., the 3'-end of the, e.g., oligonucleotide provides a free 3'-OH group whereto further "nucleotides" may be attached by a template-dependent DNA polymerase establishing 3' to 5' phosphodiester linkage whereby deoxynucleoside triphosphates are used and whereby pyrophosphate is released. Therefore, there is—except possibly for the intended function—no fundamental difference between a "primer", an "oligonucleotide", or a "probe".

The term "hybridizing" refers to the annealing of one or more probes to an amplification product. Hybridization conditions typically include a temperature that is below the melting temperature of the probes but that avoids non-specific hybridization of the probes.

The term "5' to 3' nuclease activity" refers to an activity of a nucleic acid polymerase, typically associated with the nucleic acid strand synthesis, whereby nucleotides are removed from the 5' end of nucleic acid strand.

The term "thermostable polymerase" refers to a polymerase enzyme that is heat stable, i.e., the enzyme catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have been isolated from *Thermus flavus, T. ruber, T. thermophilus, T. aquaticus, T. lacteus, T. rubens, Bacillus stearothermophilus*, and *Methanothermus fervidus*. Nonetheless, polymerases that are not thermostable also can be employed in PCR assays provided the enzyme is replenished.

The term "complement thereof" refers to nucleic acid that is both the same length as, and exactly complementary to, a given nucleic acid.

The term "extension" or "elongation" when used with respect to nucleic acids refers to when additional nucleotides (or other analogous molecules) are incorporated into the nucleic acids. For example, a nucleic acid is optionally extended by a nucleotide incorporating biocatalyst, such as a polymerase that typically adds nucleotides at the 3' terminal end of a nucleic acid.

The terms "identical" or percent "identity" in the context of two or more nucleic acid sequences, refer to two or more sequences or subsequences that are the same or have a specified percentage of nucleotides that are the same, when compared and aligned for maximum correspondence, e.g., as measured using one of the sequence comparison algorithms available to persons of skill or by visual inspection. Exemplary algorithms that are suitable for determining percent sequence identity and sequence similarity are the BLAST programs, which are described in, e.g., Altschul et al. (1990) "Basic local alignment search tool" *J. Mol. Biol.* 215:403-410, Gish et al. (1993) "Identification of protein coding regions by database similarity search" *Nature Genet.* 3:266-272, Madden et al. (1996) "Applications of network BLAST server" *Meth. Enzymol.* 266:131-141, Altschul et al. (1997) "Gapped BLAST and PSI-BLAST: a new generation of protein database search programs" *Nucleic Acids Res.* 25:3389-3402, and Zhang et al. (1997) "PowerBLAST: A new network BLAST application for interactive or automated sequence analysis and annotation" *Genome Res.* 7:649-656, which are each incorporated herein by reference.

A "modified nucleotide" in the context of an oligonucleotide refers to an alteration in which at least one nucleotide of the oligonucleotide sequence is replaced by a different nucleotide that provides a desired property to the oligonucleotide. Exemplary modified nucleotides that can be substituted in the oligonucleotides described herein include, e.g., a C5-methyl-dC, a C5-ethyl-dC, a C5-methyl-dU, a C5-ethyl-dU, a 2,6-diaminopurine, a C5-propynyl-dC, a C5-propynyl-dU, a C7-propynyl-dA, a C7-propynyl-dG, a C5-propargylamino-dC, a C5-propargylamino-dU, a C7-propargylamino-dA, a C7-propargylamino-dG, a 7-deaza-2-deoxyxanthosine, a pyrazolopyrimidine analog, a pseudo-dU, a nitro pyrrole, a nitro indole, 2'-0-methyl Ribo-U, 2'-0-methyl Ribo-C, an N4-ethyl-dC, an N6-methyl-dA, and the like. Many other modified nucleotides that can be substituted in the oligonucleotides are referred to herein or are otherwise known in the art. In certain embodiments, modified nucleotide substitutions modify melting temperatures (Tm) of the oligonucleotides relative to the melting temperatures of corresponding unmodified oligonucleotides. To further illustrate, certain modified nucleotide substitutions can reduce non-specific nucleic acid amplification (e.g., minimize primer dimer formation or the like), increase the yield of an intended target amplicon, and/or the like in some embodiments. Examples of these types of nucleic acid modifications are described in, e.g., U.S. Pat. No. 6,001,611, which is incorporated herein by reference.

MTB-RIF and/or MTB-INH Nucleic Acids and Oligonucleotides

The present disclosure provides methods to detect MTB-RIF and/or MTB-INH by amplifying, for example, a portion of one or more of the rpoB, inhA, and katG nucleic acid sequences. Nucleic acid sequences for rpoB, inhA, and katG are available, e.g., through GenBank. Specifically, primers and probes to amplify and detect rpoB, inhA, and katG nucleic acid molecule targets are provided by the embodiments in the present disclosure.

More specifically, embodiments of the oligonucleotides each include a nucleic acid with a sequence selected from SEQ ID NOs: 1 through 409, a substantially identical variant thereof in which the variant has at least, e.g., 80%, 90%, or 95% sequence identity to one of SEQ ID NOs: 1 through 409, or a complement of SEQ ID NOs: 1 through 409, and the variant.

TABLE I

Probe for rpoB, inhA, and katG nucleic acid molecule targets

| rpoB 531L Oligo Name | SEQ ID NO: | TCG/TTG Sequence | Ser/Leu Modifications |
|---|---|---|---|
| RMRPO3SP531L09 | 1 | FGTTGGQJGCTGGGGCP | F-Threo-FAM::P-Phosphate::Q-BHQ-2, J-G-clamp |
| RMRPO3SP531L18 | 2 | FACTGTTQGGLGLTGGGP | F-Threo-FAM::P-Phosphate::Q-BHQ-2, L = Propynyl dC |
| RMRPO3SP531L19 | 3 | FCTGTTQGGLGLUGGGP | F-Threo-FAM::P-Phosphate::Q-BHQ-2, L = Propynyl dC, U = propynyl dU |
| RMRPO3S531L18B | 4 | FACTGTTQGGLGLUGGGP | F-Threo-FAM::P-Phosphate::Q-BHQ-2, L = Propynyl dC, U = propynyl dU |
| RMRPO3S531L18C | 5 | FCTGTUQGGLGLUGGGP | F-Threo-FAM::P-Phosphate::Q-BHQ-2, L = Propynyl dC, U = propynyl dU |
| RMRPO3531L1B | 6 | FCTGTTQGGLGCTGGGGCP | F-Threo-FAM::P-Phosphate::Q-BHQ-2, L = Propynyl dC |
| RMRPO3SP531L20 | 7 | FALUGTTQGGLGLUGGP | F-Threo-FAM::P-Phosphate::Q-BHQ-2, L = Propynyl dC, U = propynyl dU |
| RMRPO3S531L20 | 8 | JCCGALTGTTGQGLGLUP | J-Threo-JA270::P-Phosphate::Q-BHQ-2, L = Propynyl dC, U = propynyl dU |
| RMRPO3SP531L22 | 9 | JCTGTTGGCGLUGQGGP | J-Threo-JA270::P-Phosphate::Q-BHQ-2, L = Propynyl dC, U = propynyl dU |
| RMRPO3SP531L24 | 10 | FLUGUUQGGLGLTGGGGLP | F-Threo-FAM::P-Phosphate::Q-BHQ-2, L = Propynyl dC, U = propynyl dU |
| RMRPO3SP531L25 | 11 | FLUGUUQGGLGLTGGGGP | F-Threo-FAM::P-Phosphate::Q-BHQ-2, L = Propynyl dC, U = propynyl dU |
| RMRPO3SP531L26 | 12 | FUGUUGQGLGLTGGGGLLLP | F-Threo-FAM::P-Phosphate::Q-BHQ-2, L = Propynyl dC, U = propynyl dU |
| RMRPO3S531L20B | 13 | FALUGUUQGGLGLUGGP | F-Threo-FAM::P-Phosphate::Q-BHQ-2, L = Propynyl dC, U = propynyl dU |

TABLE I-continued

Probe for rpoB, inhA, and katG nucleic acid molecule targets

| | | | |
|---|---|---|---|
| RMRPO3S531L20C | 14 | EALUGUUQGGLGLUGGP | E-Threo-HEX::P-Phosphate::Q-BHQ-2, L = Propynyl dC, U = propynyl dU |
| RMRPO3S531L20D | 15 | EALUGUTQGGLGLUGGP | F-Threo-FAM::P-Phosphate::Q-BHQ-2, L = Propynyl dC, U = propynyl dU |
| RMRPO3S531L25B | 16 | ELUGUUQGGLGLUGGGP | E-Threo-HEX::P-Phosphate::Q-BHQ-2, L = Propynyl dC, U = propynyl dU |
| RMRPO3S531L25C | 17 | ELUGUUQGGLGLUGGLP | E-Threo-HEX::P-Phosphate::Q-BHQ-2, L = Propynyl dC, U = propynyl dU |
| RMRPO3S531L20F | 18 | EALUGUUQGGLGLUGLAGLP | E-Threo-HEX::P-Phosphate::Q-BHQ-2, L = Propynyl dC, U = propynyl dU |
| RMRPO3531L20HS | 19 | EALUGUUQJGGLGLUGGP | E-Threo-HEX::P-Phosphate::Q-BHQ-2, L = Propynyl dC, U = propynyl dU |
| RMRPO3531L25C2 | 20 | ELUGUUGQGLGLUGGLP | E-Threo-HEX::P-Phosphate::Q-BHQ-2, L = Propynyl dC, U = propynyl dU |
| RMRPO3531L20C2 | 21 | EALUGUUQGGLGLUGLP | E-Threo-HEX::P-Phosphate::Q-BHQ-2, L = Propynyl dC, U = propynyl dU |
| RMRPO3531L25C3 | 22 | EALUGUUQGGLGLUGGLP | E-Threo-HEX::P-Phosphate::Q-BHQ-2, L = Propynyl dC, U = propynyl dU |
| RMRPO3S531F1 | 23 | EALUGUUQLGLGLUGGP | E-Threo-HEX::P-Phosphate::Q-BHQ-2, L = Propynyl dC, U = propynyl dU |
| RMRPO3531L25B2 | 24 | ELUGUUQGGLGLTGGGP | E-Threo-HEX::P-Phosphate::Q-BHQ-2, L = Propynyl dC, U = propynyl dU |
| RMRPO3531L31 | 25 | EUGUUGQGLGLTGGGGP | E-Threo-HEX::P-Phosphate::Q-BHQ-2, L = Propynyl dC, U = propynyl dU |
| RMRPO3531L25B3 | 26 | ELUGUUGQGLGLTGGGP | E-Threo-HEX::P-Phosphate::Q-BHQ-2, L = Propynyl dC, U = propynyl dU |
| RMRPO3531L25B4 | 27 | ELUGUUGQGLGLTGGCP | E-Threo-HEX::P-Phosphate::Q-BHQ-2, L = Propynyl dC, U = propynyl dU |
| RMRPO3F531L | 28 | FCCJACAQGTCGGCGCTTGP | F-Threo-FAM::J-t-Butyl benzyl-dA::P-Phosphate::Q-BHQ-2 |
| RMRPO3F531L 02 | 29 | FCCJACAQGTCGGCGCTTGTGGGTCP | F-Threo-FAM::J-t-Butyl benzyl-dA::P-Phosphate::Q-BHQ-2 |
| RMRPO3F531L 04 | 30 | FCCAACAQGTLGGLGLTTGP | F-Threo-FAM::P-Phosphate::Q-BHQ-2, L = Propynyl dC |
| RMRPO3F531L05 | 31 | FCCAACQAGTLGGLGLTTGP | F-Threo-FAM::P-Phosphate::Q-BHQ-2, L = Propynyl dC |
| RMRPO3F531L06 | 32 | FCCAACAQGULGGLGLTUGP | F-Threo-FAM::P-Phosphate::Q-BHQ-2, L = Propynyl dC, U = propynyl dU |
| RMRPO3AP531L11 | 33 | FCCAACAQGTJGGCGCTTGP | F-Threo-FAM::P-Phosphate::Q-BHQ-2, J-G-clamp |
| RMRPO3AP531L12 | 34 | FCCAAJAQGTCGGCGCTTGP | F-Threo-FAM::P-Phosphate::Q-BHQ-2, J-G-clamp |

TABLE I-continued

Probe for rpoB, inhA, and katG nucleic acid molecule targets

| Oligo Name | SEQ ID NO: | Sequence | Modifications |
|---|---|---|---|
| RMRPO3AP531L13 | 35 | FCCAACAQGTCGGJGCTTGP | F-Threo-FAM::P-Phosphate::Q-BHQ-2, J-G-clamp |
| RMRPO3AP531L14 | 36 | FCCAACAQGTCGGCGJTTGP | F-Threo-FAM::P-Phosphate::Q-BHQ-2, J-G-clamp |
| RMRPO3A531L12B | 37 | FCCAALQAGUCGGCGCTTGP | F-Threo-FAM::P-Phosphate::Q-BHQ-2, L = Propynyl dC, U = propynyl dU |
| RMRPO3AP531L17 | 38 | FCCAALQAGTLGGLGLP | F-Threo-FAM::P-Phosphate::Q-BHQ-2, L = Propynyl dC |
| RMRPO3A531L17B | 39 | FCCAALQAGTLGGLGLP | F-Threo-FAM::P-Phosphate::Q-BHQ-2, L = Propynyl dC |
| RMRPO3A531L19 | 40 | FCCAALQAGTLGGLGCTP | F-Threo-FAM::P-Phosphate::Q-BHQ-2, L = Propynyl dC |
| RMRPO3A531L20 | 41 | ECCAALQAGTLGGLGCTP | E-Threo-HEX::P-Phosphate::Q-BHQ-2, L = Propynyl dC |
| RMRPO3A531L18D | 42 | JCCAALAGULGGCQGLTP | J-Threo-JA270::P-Phosphate::Q-BHQ-2, L = Propynyl dC, U = propynyl dU |
| RMRPO3A531L12C | 43 | ECCAALQAGUCGGCGCTTGP | E-Threo-HEX::P-Phosphate::Q-BHQ-2, L = Propynyl dC, U = propynyl dU |
| RMRPO3A531L12D | 44 | ECCAALQAGULGGCGCTTGP | E-Threo-HEX::P-Phosphate::Q-BHQ-2, L = Propynyl dC, U = propynyl dU |
| RMRPO3531L17B2 | 45 | ECCAALQAGULGGLGLP | E-Threo-HEX::P-Phosphate::Q-BHQ-2, L = Propynyl dC, U = propynyl dU |
| RMRPO3531L17B3 | 46 | ELLAALAQGULGGLGLP | E-Threo-HEX::P-Phosphate::Q-BHQ-2, L = Propynyl dC, U = propynyl dU |
| RMRPO3A531L21 | 47 | FLLAALQAGULGGLGLUP | F-Threo-FAM::P-Phosphate::Q-BHQ-2, L = Propynyl dC, U = propynyl dU |
| RMRPO3A531L22 | 48 | FLLJALQAGULGGLGLP | F-Threo-FAM::P-Phosphate::Q-BHQ-2, L = Propynyl dC, U = propynyl dU, J-G-clamp |
| RMRPO3531L17B4 | 49 | FLLAALQAGULGGLGLP | F-Threo-FAM::P-Phosphate::Q-BHQ-2, L = Propynyl dC, U = propynyl dU |
| RMRPO3531L17B5 | 50 | FLLJALQAGULGGLGLP | E-Threo-HEX::P-Phosphate::Q-BHQ-2, L = Propynyl dC, U = propynyl dU, t-Butyl benzyl-dA |
| RMRPO3A531L20B | 51 | ELLAALAQGULGGLGLP | E-Threo-HEX::P-Phosphate::Q-BHQ-2, L = Propynyl dC |
| RM5L17B3a | 52 | ELLAALAQGTLGGLGLP | E-Threo-HEX::P-Phosphate::Q-BHQ-2, L = Propynyl dC |

| rpoB 531W Oligo Name | SEQ ID NO: | TCG/TGG Sequence | Ser/Trp Modifications |
|---|---|---|---|
| RMRPO3F531W | 53 | FCCLACAQGTCGGCGCTTGP | F = Threo-FAM; Q = t-Butyl benzyl-dC; P = Phosphate; Q = BHQ-2 |
| RMRPO3F531W02 | 54 | FCCLACAQGTCGGCGCTTGTP | F = Threo-FAM; L = t-Butyl benzyl-dC; P = Phosphate; Q = BHQ-2 |
| RMRPO3F531W06 | 55 | FCCJACAQGTCGGCGCP | F-Threo-FAM::P-Phosphate::Q-BHQ-2, |

TABLE I-continued

| Probe for rpoB, inhA, and katG nucleic acid molecule targets | | | |
|---|---|---|---|
| | | | J-G-clamp |
| rpoB 526L Oligo Name | SEQ ID NO: | CAC/CTC Sequence | His/Leu Modifications |
| RMRPO3A07 | 56 | FLUUGAGQGGULAALLLLP | F-Threo-FAM::P-Phosphate::Q-BHQ-2,L = Propynyl dC:U = propynyl dU |
| RMRPO3A07B2 | 57 | FTTGAGGQGTLAALCCCGACGGGGP | F-Threo-FAM::P-Phosphate::Q-BHQ-2,L = Propynyl dC:U = propynyl dU |
| RMRPO3A08 | 58 | FALLLULQAAGLGLLGP | F-Threo-FAM::P-Phosphate::Q-BHQ-2,L = Propynyl dC:U = propynyl dU |
| RMRPO3A08B | 59 | FALLLULQAAGLGLLP | F-Threo-FAM::P-Phosphate::Q-BHQ-2,L = Propynyl dC:U = propynyl dU |
| RMRPO3A08C | 60 | FALLLULQAAGCGLLGP | F-Threo-FAM::P-Phosphate::Q-BHQ-2,L = Propynyl dC:U = propynyl dU |
| RMRPO3A09 | 61 | JLUUGAGGGULAAQLLLLP | J-JA270::P-Phosphate::Q-BHQ-2,L = Propynyl dC:U = propynyl dU |
| AYRPO3526LFM07 | 62 | FLUUGAGGGQULAALLLLGAP | F-Threo-FAM::P-Phosphate::Q-BHQ-2::L-pdC:: U-pdU |
| AYRPO3526LFM08 | 63 | FGLUUGAGQGGULAALLLLGAP | F-Threo-FAM::P-Phosphate::Q-BHQ-2::L-pdC:: U-pdU |
| AYRPO3526LFM09 | 64 | FGLUUGAGGQGULAALLLLGAP | F-Threo-FAM::P-Phosphate::Q-BHQ-2::L-pdC:: U-pdU |
| AYRPO3526LFM10 | 65 | FGLUUGAGGGQULAALLLLGAP | F-Threo-FAM::P-Phosphate::Q-BHQ-2::L-pdC:: U-pdU |
| AYRPO3526LFM11 | 66 | FGLUUGAGGQGJLAALLLLGAP | F-Threo-FAM::P-Phosphate::Q-BHQ-2::J-G-clamp::L-pdC:: U-pdU |
| AYRPO3526LFM12 | 67 | FGLUUGAGGGQUJAALLLLGAP | F-Threo-FAM::P-Phosphate::Q-BHQ-2::J-G-clamp::L-pdC:: U-pdU |
| AYRPO3526LJA01 | 68 | FGLUUGAGGQGULAALLLLGAP | F-th-JA270::P-Phosphate::Q-BHQ-2::L-pdC:: U-pdU |
| AYRPO3526LJA02 | 69 | FGLUUGAGGGQULAALLLLGAP | F-th-JA270::P-Phosphate::Q-BHQ-2::L-pdC:: U-pdU |
| AYRPO3526LJA03 | 70 | FGLUUGAGGQGJLAALLLLGAP | F-th-JA270::P-Phosphate::Q-BHQ-2::J-G-clamp::L-pdC:: U-pdU |
| AYRPO3526LJA04 | 71 | FGLUUGAGGGQUJAALLLLGAP | F-th-JA270::P-Phosphate::Q-BHQ-2::J-G-clamp::L-pdC:: U-pdU |
| AYRPO3526LJA05 | 72 | FGLUUGAGGGJQLAALLLLGAP | F-th-JA270::P-Phosphate::Q-BHQ-2::J-G-clamp::L-pdC:: U-pdU |
| AYRPO3526LJA06 | 73 | FGLUUGAGGGJLAAQIILLGAP | F-th-JA270::P-Phosphate::Q-BHQ-2::J-G-clamp::L-pdC:: U-pdU |

TABLE I-continued

Probe for rpoB, inhA, and katG nucleic acid molecule targets

| rpoB 526Y Oligo Name | SEQ ID NO: | CAC/TAC Sequence | His/Tyr Modifications |
|---|---|---|---|
| RMRPO3A06E | 74 | JUUGUAGGULAALQLLLGAP | J-JA270::P-Phosphate::Q-BHQ-2,L = Propynyl dC, U = propynyl dU |
| AYRPO3526YFM07 | 75 | FLUUGUJGGQULAALLLLGAP | F-Threo-FAM::P-Phosphate::Q-BHQ-2::J-T-propdA:L -pdC:: U pdU |
| AYRPO3526YFM08 | 76 | FLUUGQUJGGULAALLLLGAP | F-Threo-FAM::P-Phosphate::Q-BHQ-2::J-T-propdA::L -pdc:: U-pdU |
| AYRPO3526YFM09 | 77 | FLUUGUJGQGULAALLLLGAP | F-Threo-FAM::P-Phosphate::Q-BHQ-2::J-T-propdA::L -pdC:: U-pdU |
| AYRPO3526YFM10 | 78 | FLUUGUAGQGULAALLLLGAP | F-Threo-FAM::P-Phosphate::Q-BHQ-2::L -pdC:: U-pdU |
| AYRPO3526YHX01 | 79 | FLUUGUJGQGULAALLLLGAP | F-Threo-HEX::P-Phosphate::Q-BHQ-2::J-T-propdA:L -pdC:: U-pdU |
| AYRPO3526YHX02 | 80 | FLUUGUAGQGULAALLLLGAP | F-Threo-HEX::P-Phosphate::Q-BHQ-2::L -pdC:: U-pdU |
| AYRPO3526YHX03 | 81 | FUUGUJGQGULAALLLLGAP | F-Threo-HEX::P-Phosphate::Q-BHQ-2::J-T-propdA:L -pdC:: U-pdU |
| AYRPO3526YHX04 | 82 | FUUGUJGQGULAALLLLP | F-Threo-HEX::P-Phosphate::Q-BHQ-2::J-T-propdA:L -pdC:: U pdU |
| AYRPO3526YHX05 | 83 | FUUGUJQGGULAALLLLP | F-Threo-HEX::P-Phosphate::Q-BHQ-2::J-T-propdA:L -pdC:: U-pdU |
| AYRPO3526YHX06 | 84 | FLUUGUAGQGJLAALLLLGAP | F-Threo-HEX::P-Phosphate::Q-BHQ-2::J-G-clamp::L -pdC:: U-pdU |
| AYRPO3526YHX07 | 85 | FLUUGUAGQGULAALLLLGALAP | F-Threo-HEX::P-Phosphate::Q-BHQ-2::L -pdC:: U-pdU |
| AYRPO3526YHX08 | 86 | FLGLUUGUAGQGULAALLLLGAP | F-Threo-HEX::P-Phosphate::Q-BHQ-2::L -pdC:: U-pdU |
| AYRPO3526YHX09 | 87 | FGLUUGUAGQGULAALLLLGALAP | F-Threo-HEX::P-Phosphate::Q-BHQ-2::L -pdC:: U-pdU |
| AYRPO3526YHX10 | 88 | FLGLUUGUAGQGULAALLLLGALAP | F-Threo-HEX::P-Phosphate::Q-BHQ-2::L -pdC:: U-pdU |

| rpoB: 526D Name | SEQ ID NO: | CAC/GAC Sequence | His/Asp Modifications |
|---|---|---|---|
| RMRPO3A03C | 89 | FLUUGULQGGUCAACLLLP | F-Threo-FAM::P-Phosphate::Q-BHQ-2,L = Propynyl dC: U = propynyl dU |
| RMRPO3A03D | 90 | JLUUGULGGULAAQLLCCP | J-JA270::P-Phosphate::Q-BHQ-2,L = Propynyl dC, U = propynyl dU |
| AYRPO3526DFM03 | 91 | FTGTJGQGTCAACCCCGAP | F-Threo-FAM::P-Phosphate::Q-BHQ-2::J-G-Clamp |
| AYRPO3526DFM04 | 92 | FTGTJGGQTCAACCCCGAP | F-Threo-FAM::P-Phosphate::Q-BHQ-2::J-G-Clamp |
| AYRPO3526DFM05 | 93 | FGTTGTQJGGTCAACCCCGAP | F-Threo-FAM::P-Phosphate::Q-BHQ-2::J-G-Clamp |

TABLE I-continued

Probe for rpoB, inhA, and katG nucleic acid molecule targets

| | | | |
|---|---|---|---|
| AYRPO3526DFM06 | 94 | FGTTGTJGGQTCAACCCCGAP | F-Threo-FAM::P-Phosphate::Q-BHQ-2::J-G-Clamp |
| AYRPO3526DJA07 | 95 | FUUGUJGGULAQALLLLP | F-JA270::P-Phosphate::Q-BHQ-2::L-pdC:: U-pdU::J-G-Clamp |
| AYRPO3526DJA08 | 96 | FLUUGUJGGULAQALLLLP | F-JA270::P-Phosphate::Q-BHQ-2::L-pdC:: U pdU::J-G-Clamp |
| AYRPO3526DJA09 | 97 | FUUGUJGGULAQALLLLGAP | F-JA270::P-Phosphate::Q-BHQ-2::L-pdC:: U-pdU::J-G-Clamp |
| AYRPO3526DJA10 | 98 | FLUUGUJGGULAQALLLLGAP | F-JA270::P-Phosphate::Q-BHQ-2::L-pdC:: U-pdU::J-G-Clamp |
| AYRPO3526DJA11 | 99 | FGLUUGUJGGULAQALLLLGAP | F-JA270::P-Phosphate::Q-BHQ-2::L-pdC:: U pdU::J-G-Clamp |

| rpoB 526N Oligo Name | SEQ ID NO: | CAC/AAC Sequence | His/Asn Modifications |
|---|---|---|---|
| RMRPO3SP526R2 | 100 | FACCAAQLAAGLGLLGP | F-Threo-FAM::P-Phosphate::Q-BHQ-2,L = Propynyl dC |
| RMRPO3SP526R3 | 101 | FALLAAQLAAGLGLLGP | F-Threo-FAM::P-Phosphate::Q-BHQ-2,L = Propynyl dC |
| RMRPO3AP526R1 | 102 | FTTGTTQGGTLAALLCCGAP | F-Threo-FAM::P-Phosphate::Q-BHQ-2,L = Propynyl dC |
| RMRPO3AP526N1 | 103 | FUUGUUQGGULAALLLP | F-Threo-FAM::P-Phosphate::Q-BHQ-2,L = Propynyl dC |
| RMRPO3AP526N2 | 104 | FUUGUUQGGULAALLLGP | F-Threo-FAM::P-Phosphate::Q-BHQ-2,L = Propynyl dC |
| RMRPO3AP526N2B | 105 | FUUGUUQGGULJJLLLP | F-Threo-FAM::P-Phosphate::Q-BHQ-2,L = Propynyl dC:U = propynyl dU |
| RMRPO3SP526N4 | 106 | FALLAALQAAGLGLLGALUP | F-Threo-FAM::P-Phosphate::Q-BHQ-2,L = Propynyl dC:U = propynyl dU |
| RMRPO3SP526N4B | 107 | EALLAALQAAGLGLLGALUP | H-Threo-HEX::P-Phosphate::Q-BHQ-2,L = Propynyl dC:U = propynyl dU |
| RMRPO3SP526N4B2 | 108 | EALLAAQLAAGLGLLGALP | H-Threo-HEX::P-Phosphate::Q-BHQ-2,L = Propynyl dC:U = propynyl dU |
| RMRPO3SP526N4B2b | 109 | EALLAAQLAAGLGLLGAP | H-Threo-HEX::P-Phosphate::Q-BHQ-2,L = Propynyl dC:U = propynyl dU |
| RMRPO3SP526N4B3 | 110 | FLAALQAAGLGLLGALUGP | F-Threo-FAM::P-Phosphate::Q-BHQ-2,L = Propynyl dC:U = propynyl dU |
| RMRPO3SP526N4C | 111 | FALLAALQAAGLGLLGP | F-Threo-FAM::P-Phosphate::Q-BHQ-2,L = Propynyl dC |
| RMRPO3SP526N5 | 112 | FALLAAQLAAGLGLLGALUP | F-Threo-FAM::P-Phosphate::Q-BHQ-2,L = Propynyl dC:U = propynyl dU |
| RMRPO3AP526N6 | 113 | FUUGUUQGGULAALLLLGAP | F-Threo-FAM::P-Phosphate::Q-BHQ-2,L = Propynyl dC:U = propynyl dU |

TABLE I-continued

Probe for rpoB, inhA, and katG nucleic acid molecule targets

| | | | |
|---|---|---|---|
| RMRPO3AP526N7 | 114 | FUUGUQUGGULAALLLLGAP | F-Threo-FAM::P-Phosphate::Q-BHQ-2,L = Propynyl dC:U = propynyl dU |
| RMRPO3AP526N8 | 115 | FUUGUUQGGULAALLLLP | F-Threo-FAM::P-Phosphate::Q-BHQ-2,L = Propynyl dC:U = propynyl dU |
| RMRPO3AP526N9 | 116 | FUUGUUQGGULOOLLLLP | F-Threo-FAM::P-Phosphate::Q-BHQ-2,L = Propynyl dC:U = propynyl dU, O-t-butyl benzyl dA |
| RMRPO3AP526N1B | 117 | FUUGUUQGGULJJLLLP | F-Threo-FAM::P-Phosphate::Q-BHQ-2,L = Propynyl dC,J-N6 methyl dA |
| RMRPO3A526N8B | 118 | FUUGUUGQGULAALLLLP | F-Threo-FAM::P-Phosphate::Q-BHQ-2,L = Propynyl dC:U = propynyl dU |

| rpoB 533 Oligo Name | SEQ ID NO: | CTG/CCG Sequence | Leu/Pro Modifications |
|---|---|---|---|
| RMRPO3H533P10B | 119 | ECGCJGGQGGCCCGGCP | E-Threo-HEX::P-Phosphate::Q-BHQ-2, J-G-clamp |
| RMRPO3H533P10D | 120 | FLGLLGGQGGLLLGGLGGP | F-Threo-FAM::P-Phosphate::Q-BHQ-2, J-G-clamp,L = Propynyl dC |
| RMRPO3H533P10 | 121 | ECGCCGGQGGCCCGGCGGP | H-Threo-HEX::P-Phosphate::Q-BHQ-2 rpoB: 513L |

| rpoB: 513L Name | SEQ ID NO: | CAA/CTA Sequence | Gln/Leu Modifications |
|---|---|---|---|
| JJS513L44PJ12 | 122 | FLAGLUGAGLLUAQUULP | L = pdC, U = pdU, F = th-JA270, Q = BHQ2, p = phosphate |
| JJS513L68PJ12 | 123 | FLLUAUULAUGGAQLLAGP | L = pdC, U = pdU, F = th-JA270, Q = BHQ2, p = phosphate |
| JJS513L59PJ12 | 124 | FLLAGLUGAGLLUQAUULP | L = pdC, U = pdU, F = th-JA270, Q = BHQ2, p = phosphate |
| JJS513L101PJ12 | 125 | FAGLLUAUULAUGQGALLAGP | L = pdC, U = pdU, F = th-JA270, Q = BHQ2, p = phosphate |
| JJS513L84PJ12 | 126 | FGLLUAUULATGGQALLAGP | L = pdC, U = pdU, F = th-JA270, Q = BHQ2, p = phosphate |
| JJA513L60PJ12 | 127 | FUGAAUAGGLULAQGLUGP | L = pdC, U = pdU, F = th-JA270, Q = BHQ2, p = phosphate |
| JJA513L68PJ12 | 128 | FLUGGULLAUGAAQTAGGP | L = pdC, U = pdU, F = th-JA270, Q = BHQ2, p = phosphate |
| JJA513L103PJ12 | 129 | FUULGGULLAUGQAAUAGGP | L = pdC, U = pdU, F = th-JA270, Q = BHQ2, p = phosphate |
| JJA513L61PJ12 | 130 | FAUGAAUAGGLULQAGLUP | L = pdC, U = pdU, F = th-JA270, Q = BHQ2, p = phosphate |
| JJA513L76PJ12 | 131 | FUGAAUAGGLULAQGLUGGP | L = pdC, U = pdU, F = th-JA270, Q = BHQ2, p = phosphate |
| JJA513L59PJ12 | 132 | FGAAUAGGLULAGQLUGGP | L = pdC, U = pdU, F = th-JA270, Q = BHQ2, p = phosphate |
| JJA513L95PJ12 | 133 | FLAUGAAUAGGLUQLAGLUGP | L = pdC, U = pdU, F = th-JA270, Q = BHQ2, p = phosphate |
| JJA513L924PJ2 | 134 | FGAAUAGGLULAGQUUGGLUP | L = pdC, U = pdU, F = th-JA270, Q = BHQ2, p = phosphate |

TABLE I-continued

Probe for rpoB, inhA, and katG nucleic acid molecule targets

| Name | SEQ ID NO: | Sequence | Modifications |
| --- | --- | --- | --- |
| JJA513L928PJ2 | 135 | FGAAUAGGUULAGQLUGGLUP | L = pdC, U = pdU, F = th-JA270, Q = BHQ2, p = phosphate |
| JJA513L927PJ2 | 136 | FGAAUAGGLUUAGQLUGGLUP | L = pdC, U = pdU, F = th-JA270, Q = BHQ2, p = phosphate |
| JJA513L9232PJ2 | 137 | FGAAUAGGLUGAGQLUGGLUP | L = pdC, U = pdU, F = th-JA270, Q = BHQ2, p = phosphate |
| JJA513L9243PJ2 | 138 | FGAAUAGGLULLGQLUGGLUP | L = pdC, U = pdU, F = th-JA270, Q = BHQ2, p = phosphate |
| JJA513L9217PJ2 | 139 | FGAAUAGGLULAGQLAGGLUP | L = pdC, U = pdU, F = th-JA270, Q = BHQ2, p = phosphate |
| JJA513L9218PJ2 | 140 | FGAAUAGGLULAGQAUGGLUP | L = pdC, U = pdU, F = th-JA270, Q = BHQ2, p = phosphate |
| JJA513L9222PJ2 | 141 | FGAAUAGGAULAGQLUGGLUP | L = pdC, U = pdU, F = th-JA270, Q = BHQ2, p = phosphate |
| JJA513L75PJ12 | 142 | FGAAUAGGLULAGQLUGGLP | L = pdC, U = pdU, F = th-JA270, Q = BHQ2, p = phosphate |
| JJA513L75PCA12 | 143 | FGAAUAGGLULAGQLUGGLP | L = pdC, U = pdU, F = CAL Fluor Red 635, Q = BHQ2, p = phosphate |
| JJA513L75PCB12 | 144 | FGAAUAGGLULAGQLUGGLP | L = pdC, U = pdU, F = CAL Fluor Red 635 dT, Q = BHQ2, p = phosphate |
| JJA513L77PJ12 | 145 | FAUGAAUAGGLULQAGLUGP | L = pdC, U = pdU, F = th-JA270, Q = BHQ2, p = phosphate |
| JJA513L93PJ12 | 146 | FUGAAUAGGLULAQGLUGGLP | L = pdC, U = pdU, F = th-JA270, Q = BHQ2, p = phosphate |
| JJS513L85PJ12 | 147 | FLLUAUULAUGGAQLLAGAP | L = pdC, U = pdU, F = th-JA270, Q = BHQ2, p = phosphate |

| rpoB: 513K Name | SEQ ID NO: | CAA/AAA Sequence | Gln/Lys Modifications |
| --- | --- | --- | --- |
| JJS513K84PJ12 | 148 | FAGLAAAUULAUGQGALLAP | L = pdC, U = pdU, F = th-JA270, Q = BHQ2, p = phosphate |
| JJS513K77PJ12 | 149 | FLLAGLUGAGLAAQAUULAP | L = pdC, U = pdU, F = th-JA270, Q = BHQ2, p = phosphate |
| JJS513K79PJ12 | 150 | FAGLUGAGLAAAUQULAUGP | L = pdC, U = pdU, F = th-JA270, Q = BHQ2, p = phosphate |
| JJS513K85PJ12 | 151 | FGLAAAUULAUGGQALLAGP | L = pdC, U = pdU, F = th-JA270, Q = BHQ2, p = phosphate |
| JJA513K43PJ12 | 152 | FAUUUGLULAGLUQGGLP | L = pdC, U = pdU, F = th-JA270, Q = BHQ2, p = phosphate |
| JJA513K77PJ12 | 153 | FUGAAUUUGLULAQGLUGGP | L = pdC, U = pdU, F = th-JA270, Q = BHQ2, p = phosphate |
| JJA513K60PJ12 | 154 | FGAAUUUGLULAGQLUGGP | L = pdC, U = pdU, F = th-JA270, Q = BHQ2, p = phosphate |
| JJA513K76PJ12 | 155 | FGAAUUUGLULAGQLUGGLP | L = pdC, U = pdU, F = th-JA270, Q = BHQ2, p = phosphate |
| JJA513K76PCA12 | 156 | FGAAUUUGLULAGQLUGGLP | L = pdC, U = pdU, F = CAL Fluor Red 635, Q = BHQ2, p = phosphate |
| JJA513K76PCB12 | 157 | FGAAUUUGLULAGQLUGGLP | L = pdC, U = pdU, F = CAL Fluor Red 635 dT, Q = BHQ2, p = phosphate |
| JJA513K44PJ12 | 158 | FAAUUUGLULAGLQUGGP | L = pdC, U = pdU, F = th-JA270, Q = BHQ2, p = phosphate |

TABLE I-continued

Probe for rpoB, inhA, and katG nucleic acid molecule targets

| Name | SEQ ID NO: | Sequence | Modifications |
|---|---|---|---|
| JJA513K80PJ12 | 159 | FLLAUGAAUUUGLQULAGLP | L = pdC, U = pdU, F = th-JA270, Q = BHQ2, p = phosphate |
| JJA513K59PJ12 | 160 | FAAUUUGLULAGLQUGGLP | L = pdC, U = pdU, F = th-JA270, Q = BHQ2, p = phosphate |
| JJA513K75PJ12 | 161 | FAAUUUGLULAGQLUGGLUP | L = pdC, U = pdU, F = th-JA270, Q = BHQ2, p = phosphate |

| rpoB: 513P Name | SEQ ID NO: | CAA/CCA Sequence | Gln/Pro Modifications |
|---|---|---|---|
| JJS513P66PJ12 | 162 | FAGLLLAUULAUGQGALLP | L = pdC, U = pdU, F = th-JA270, Q = BHQ2, p = phosphate |
| JJS513P83PJ12 | 163 | FAGLLLAUULAUGQGALLAP | L = pdC, U = pdU, F = th-JA270, Q = BHQ2, p = phosphate |
| JJS513P68PJ12 | 164 | FLLLAUULAUGGAQLLAGP | L = pdC, U = pdU, F = th-JA270, Q = BHQ2, p = phosphate |
| JS513P81PJ12 | 165 | FUGAGLLLAUULAQUGGALP | L = pdC, U = pdU, F = th-JA270, Q = BHQ2, p = phosphate |
| JJA513P60PJ12 | 166 | FUGAAUGGGLULAQGLUGP | L = pdC, U = pdU, F = th-JA270, Q = BHQ2, p = phosphate |
| JJA513P76PJ12 | 167 | FUGAAUGGGLTLAQGLUGGP | L = pdC, U = pdU, F = th-JA270, Q = BHQ2, p = phosphate |
| JJS513P66GJ12 | 168 | FAGLLEAUULAUGQGALLP | E = G-clamp, L = pdC, U = pdU, F = th-JA270, Q = BHQ2, p = phosphate |
| JJS513P83GJ12 | 169 | FAGLLEAUULAUGQGALLAP | E = G-clamp, L = pdC, U = pdU, F = th-JA270, Q = BHQ2, p = phosphate |
| JJS513P84PJ12 | 170 | FGLLLAUULAUGGQALLAGP | L = pdC, U = pdU, F = th-JA270, Q = BHQ2, p = phosphate |
| JJS513P82PJ12 | 171 | FGAGLLLAUULAUQGGALLP | L = pdC, U = pdU, F = th-JA270, Q = BHQ2, p = phosphate |
| JJS513P84GJ12 | 172 | FGLLEAUUCAUGGQALLAGP | E = G-clamp, L = pdC, U = pdU, F = th-JA270, Q = BHQ2, p = phosphate |
| JJS513P82GJ12 | 173 | FGAGLLEAUULAUQGGALLP | E = G-clamp, L = pdC, U = pdU, F = th-JA270, Q = BHQ2, p = phosphate |

| rpoB: 522L Name | SEQ ID NO: | TCG/TTG Sequence | Ser/Leu Modifications |
|---|---|---|---|
| JJA522L50PJ12 | 174 | FGGULAALLLLAAQLAGP | L = pdC, U = pdU, F = th-JA270, Q = BHQ2, p = phosphate |
| JJA522L18PJ12 | 175 | FALLLLAALAGLGQGP | L = pdC, U = pdU, F = th-JA270, Q = BHQ2, p = phosphate |
| JJA522L16PJ12 | 176 | FLLLAALAGLGGGQUP | L = pdC, U = pdU, F = th-JA270, Q = BHQ2, p = phosphate |
| JJA522L17PJ12 | 177 | FLLLLAALAGLGGQGP | L = pdC, U = pdU, F = th-JA270, Q = BHQ2, p = phosphate |
| JJA522L83PJ12 | 178 | FUGGGULAALLLLQAALAGP | L = pdC, U = pdU, F = th-JA270, Q = BHQ2, p = phosphate |
| JJA522L32PJ12 | 179 | FAALLLLAALAGLQGGP | L = pdC, U = pdU, F = th-JA270, Q = BHQ2, p = phosphate |
| JJA522L33PJ12 | 180 | FLAALLLLAALAGQLGP | L = pdC, U = pdU, F = th-JA270, Q = BHQ2, p = phosphate |
| JJA522L48PJ12 | 181 | FULAALLLLAALAQGLGP | L = pdC, U = pdU, F = th-JA270, Q = BHQ2, p = phosphate |

TABLE I-continued

Probe for rpoB, inhA, and katG nucleic acid molecule targets

| | | | |
|---|---|---|---|
| JJA522L30PJ12 | 182 | FLLLLAALAGLGGQGUP | L = pdC, U = pdU, F = th-JA270, Q = BHQ2, p = phosphate |
| JJA522L31PJ12 | 183 | FALLLLAALAGLGQGGP | L = pdC, U = pdU, F = th-JA270, Q = BHQ2, p = phosphate |
| JJA522L63PJ12 | 184 | FULAALLLLAALAQGLGGP | L = pdC, U = pdU, F = th-JA270, Q = BHQ2, p = phosphate |
| JJA522L47PJ12 | 185 | FLAALLLLAALAGQLGGP | L = pdC, U = pdU, F = th-JA270, Q = BHQ2, p = phosphate |

| rpoB: 522Q Name | SEQ ID NO: | TCG/CAG Sequence | Ser/Gln Modifications |
|---|---|---|---|
| JJS522Q48J12 | 186 | FCCGCTGCAGGGGQTTGAP | F = th-JA270, Q = BHQ2, p = phosphate |
| JJS522Q32J12 | 187 | FCCCGCTGCAGGGQGTTP | F = th-JA270, Q = BHQ2, p = phosphate |
| JJS522Q49J12 | 188 | FCGCTGCAGGGGTQTGACP | F = th-JA270, Q = BHQ2, p = phosphate |
| JJA522Q31J12 | 189 | FACCCCTGCAGCGQGGTP | F = th-JA270, Q = BHQ2, p = phosphate |
| JJA522Q33J12 | 190 | FCAACCCCTGCAGQCGGP | F = th-JA270, Q = BHQ2, p = phosphate |
| JJA522Q43J12 | 191 | FCCCTGCAGCGGGQTTGTP | F = th-JA270, Q = BHQ2, p = phosphate |
| JJA522Q31PJ12 | 192 | FALLLLUGCAGLGQGGUP | L = pdC, U = pdU, F = th-JA270, Q = BHQ2, p = phosphate |
| JJS522Q49PJ12 | 193 | FLGLUGLAGGGGUQUGALP | L = pdC, U = pdU, F = th-JA270, Q = BHQ2, p = phosphate |
| JJA522Q18PJ12 | 194 | FALLLLUGLAGLGQGGP | L = pdC, U = pdU, F = th-JA270, Q = BHQ2, p = phosphate |
| JJS522Q34PJ12 | 195 | FLGLUGLAGGGGUQUGAP | L = pdC, U = pdU, F = th-JA270, Q = BHQ2, p = phosphate |
| JJA522Q20PJ12 | 196 | FLAALLLLUGLAGQLGP | L = pdC, U = pdU, F = th-JA270, Q = BHQ2, p = phosphate |
| JJA522Q33PJ12 | 197 | FLAALLLLUGLAGQLGGP | L = pdC, U = pdU, F = th-JA270, Q = BHQ2, p = phosphate |
| JJA522Q47PJ12 | 198 | FLAALLLLUGLAGQLGGGP | L = pdC, U = pdU, F = th-JA270, Q = BHQ2, p = phosphate |

| rpoB: 522W Name | SEQ ID NO: | TCG/TGG Sequence | Ser/Trp Modifications |
|---|---|---|---|
| JJA522W33PJ12 | 199 | FLAALLLLLALAGQLGP | L = pdC, U = pdU, F = th-JA270, Q = BHQ2, p = phosphate |
| JJA522W33GJ12 | 200 | FLAALLLLEALAGQLGP | E = G-clamp, L = pdC, U = pdU, F = th-JA270, Q = BHQ2, p = phosphate |
| JJA522W47J12 | 201 | FLAALLLLLALAGQLGGP | L = pdC, U = pdU, F = th-JA270, Q = BHQ2, p = phosphate |
| JJA522W47GJ12 | 202 | FLAALLLLEALAGQLGGP | E = G-clamp, L = pdC, U = pdU, F = th-JA270, Q = BHQ2, p = phosphate |
| JJA522W48PJ12 | 203 | FULAALLLLLALAQGLGP | L = pdC, U = pdU, F = th-JA270, Q = BHQ2, p = phosphate |
| JJA522W48GJ12 | 204 | FULAALLLLEALAQGLGP | E = G-clamp, L = pdC, U = pdU, F = th-JA270, Q = BHQ2, p = phosphate |

| rpoB 516V | | GAC/GTC | Asp/Val |
|---|---|---|---|
| RMRPO3F516V | 205 | FCTGGJCQCATGAATTGGCTCP | F-Threo-FAM::J-t-Butyl benzyl-dA::P-Phosphate::Q-BHQ-2 |

TABLE I-continued

Probe for rpoB, inhA, and katG nucleic acid molecule targets

| | | | |
|---|---|---|---|
| RMRPO3UNF516V | 206 | FCTGGACQCATGAATTGGCTCP | F-Threo-FAM::P-Phosphate::Q-BHQ-2 |
| RMRPO3SP516V | 207 | FTGGTCQCAGAACAACCCGCTP | F-Threo-FAM::P-Phosphate::Q-BHQ-2 |
| RMRPO3SP516Y | 208 | EATGTACQCAGAACAACCCGCTGP | F-Threo-HEX::P-Phosphate::Q-BHQ-2 |
| RMRPO3AP516Y | 209 | ECTGGTACQATGAATTGGCTCP | F-Threo-HEX::P-Phosphate::Q-BHQ-2 |
| RMRPO3A2P516Y | 210 | ECTGGTACQATGAATTGGCTCAGCP | F-Threo-HEX::P-Phosphate::Q-BHQ-2 |
| RMRPO3F516V02 | 211 | FCTGGJCQLATGAATTGGLTLP | F-Threo-FAM::P-Phosphate::Q-BHQ-2, L = Propynyl dC, J-t-Butyl benzyl-dA |
| RMRPO3SP516V03 | 212 | FTGGTCQCAGAACAACCCGCTGCGGP | F-Threo-FAM::P-Phosphate::Q-BHQ-2 |
| RMRPO3SP516VO4 | 213 | FTGGTCQCAAAACAACCCGCTP | F-Threo-FAM::P-Phosphate::Q-BHQ-2 |
| RMRPO3SP516V05 | 214 | FTGGTEQCAGAACAACCCGCTP | F-Threo-FAM::P-Phosphate::Q-BHQ-2, E-G-clamp |
| RMRPO3SP516V06 | 215 | FTGGTCQEAGAACAACCCGCTP | F-Threo-FAM::P-Phosphate::Q-BHQ-2, E-G-clamp |
| RMRPO3SP516Y02 | 216 | EATGTACQCAGAACAACCCGGGTP | E-Threo-HEX::P-Phosphate::Q-BHQ-2 |
| RMRPO3SP516V07 | 217 | FTGGTCQCAGAATAACCCGCTGCGGP | F-Threo-FAM::P-Phosphate::Q-BHQ-2 |
| RMRPO3SP516V08 | 218 | FTGGTCQCAAAACAACCCGCTGCGGP | F-Threo-FAM::P-Phosphate::Q-BHQ-2 |
| RMRPO3SP516V09 | 219 | FGGTCCQAGAACAACCCGCTGP | F-Threo-FAM::P-Phosphate::Q-BHQ-2 |
| RMRPO3SP516V10 | 220 | FATGGTCQCAGAACAACCCGCTP | F-Threo-FAM::P-Phosphate::Q-BHQ-2 |
| RMRPO3SP516V11 | 221 | ECATGGTCQCAGAACAACCCGP | H-Threo-HEX::P-Phosphate::Q-BHQ-2 |
| RMRPO3SP516V12 | 222 | FATGGTCQCAGAACAACCGGTTGP | F-Threo-FAM::P-Phosphate::Q-BHQ-2 |
| RMRPO3S516V11B | 223 | FCATGGTQCCAGAACAACCCGP | F-Threo-FAM::P-Phosphate::Q-BHQ-2 |
| RMRPO3S516V11C | 224 | FLAUGGUQLLAGAALAALLLGP | F-Threo-FAM::P-Phosphate::Q-BHQ-2, L = Propynyl dC, U = propynyl dU |
| RMRPO3S516V11D | 225 | FCATGGTCQCAGAACAACCCGP | F-Threo-FAM::P-Phosphate::Q-BHQ-2 |
| RMRPO3S516V11E | 226 | FATGGTQCCAGAACAACCCGP | F-Threo-FAM::P-Phosphate::Q-BHQ-2 |
| RMRPO3S516V11F | 227 | JCATGGTCCAGAAQCAACCCGP | J-JA270::P-Phosphate::Q-BHQ-2 |
| RMRPO3S516V11G | 228 | JLAUGGULLAGAAQLAALP | J-JA270::P-Phosphate::Q-BHQ-2 |
| RMRPO3516V11C2 | 229 | FLAUGGUQLLJGAJLAJLP | F-Threo-FAM::P-Phosphate::Q-BHQ-2, L = Propynyl dC, U = propynyl dU, J: N6-Benzyl dA |
| RM516V11G2 | 230 | FLLUGGUQLLAGAALAALP | F-Threo-FAM::P-Phosphate::Q-BHQ-2 |
| RMRPO3516V11G2 | 231 | JLAUGGULLAGAAQLAP | J-JA270::P-Phosphate::Q-BHQ-2, L = Propynyl dC, U = propynyl dU |
| RMRPO3516V11G3 | 232 | JLAUGGTLLAGAAQLAP | J-JA270::P-Phosphate::Q-BHQ-2, L = Propynyl dC, U = propynyl dU |
| RMRPO3S516V12B | 233 | FCATGGTCQCAGAACAACCGGTTGP | F-Threo-FAM::P-Phosphate::Q-BHQ-2 |
| RMRPO3516V11C4 | 234 | FLAUGGUQLLAGAALAALLP | F-Threo-FAM::P-Phosphate::Q-BHQ-2, L = Propynyl dC, U = propynyl dU |
| RMRPO3516V11E2 | 235 | FTGGTQCCAGAACAACCCGCTGP | F-Threo-FAM::P-Phosphate::Q-BHQ-2 |
| RMRPO3516V11E3 | 236 | FATGGTQCCAGAACAACAGTTGP | F-Threo-FAM::P-Phosphate::Q-BHQ-2 |

TABLE I-continued

Probe for rpoB, inhA, and katG nucleic acid molecule targets

| Oligo Name | SEQ ID NO: | Sequence | Modifications |
|---|---|---|---|
| RMRPO3516V11E5 | 237 | FTGGTQCCAGAACAACCCGCTP | F-Threo-FAM::P-Phosphate::Q-BHQ-2 |
| RMRPO3516V11E6 | 238 | FTGGTCCQAGAACAACCCGCTP | F-Threo-FAM::P-Phosphate::Q-BHQ-2 |

| rpoB 516Y Oligo Name | SEQ ID NO: | GAC/TAC Sequence | Asp/Tyr Modifications |
|---|---|---|---|
| RMRPO3SP516Y03 | 239 | EATGTAJCQAGAACAACCCGCP | E-Threo-HEX::P-Phosphate::Q-BHQ-2,J-G-clamp |
| RMRPO3S516YB2 | 240 | FATGTQACCAGAACAACCCGCTGP | F-Threo-FAM::P-Phosphate::Q-BHQ-2 |
| RMRPO3SP516Y | 241 | EATGTACQCAGAACAACCCGCTGP | E-Threo-HEX::P-Phosphate::Q-BHQ-2 |
| RMRPO3AP516Y | 242 | ECTGGTACQATGAATTGGCTCP | E-Threo-HEX::P-Phosphate::Q-BHQ-2 |
| RMRPO3A2P516Y | 243 | ECTGGTACQATGAATTGGCTCAGCP | E-Threo-HEX::P-Phosphate::Q-BHQ-2 |
| RMRPO3SP516Y02 | 244 | EATGTACQCAGAACAACCCGGGGTP | E-Threo-HEX::P-Phosphate::Q-BHQ-2 |
| RMRPO3SP516Y4B | 245 | EATGTACQCAGAACAACCCGCTGTP | E-Threo-HEX::P-Phosphate::Q-BHQ-2 |
| RMRPO3S516YB | 246 | FATGTACQCAGAACAACCCGCTGP | F-Threo-FAM::P-Phosphate::Q-BHQ-2 |
| RMRPO3S516YC | 247 | FATGTAQCCAGAACAACCCGCTGP | F-Threo-FAM::P-Phosphate::Q-BHQ-2 |

| rpoB 533P Oligo Name | SEQ ID NO: | CTG/CCG Sequence | Leu/Pro Modifications |
|---|---|---|---|
| RMRPO3H533P10B | 248 | ECGCJGGQGGCCCGGCP | E-Threo-HEX::P-Phosphate::Q-BHQ-2,J-G-clamp |
| RMRPO3H533P10D | 249 | FLGLLGGQGGLLLGGLGGP | F-Threo-FAM::P-Phosphate::Q-BHQ-2, J-G-clamp |
| RMRPO3H533 | 250 | ECCGGCGQCCGACAGTCGGCGP | H-Threo-HEX::P Phosphate::Q-BHQ-2 |
| RMRPO3H533P02 | 251 | ECCGGCGQCCGACAGTCGGP | H-Threo-HEX::P-Phosphate::Q-BHQ-2 |
| RMRPO3H533P03 | 252 | ECCGGCGQCCTACAGTCGGCGP | H-Threo-HEX::P Phosphate::Q-BHQ-2 |
| RMRPO3H533PO4 | 253 | ECCGGCGQCCAACAGTCGGCGP | H-Threo-HEX::P-Phosphate::Q-BHQ-2 |
| RMRPO3H533P05 | 254 | ECCGGCGQCCCACAGTCGGCGP | H-Threo-HEX::P-Phosphate::Q-BHQ-2 |
| RMRPO3H533P06 | 255 | ECCGGCQACCGACAGTCGGP | H-Threo-HEX::P Phosphate::Q-BHQ-2 |
| RMRPO3H533P07 | 256 | ECCGGCGQTCGACAGTCGGP | H-Threo-HEX::P-Phosphate::Q-BHQ-2 |
| RMRPO3H533P08 | 257 | ECCGGCGQCCGACAGTCGGCP | H-Threo-HEX::P Phosphate::Q-BHQ-2 |
| RMRPO3H533P09 | 258 | ECCGGCQACCGACAGTCGGCP | H-Threo-HEX::P-Phosphate::Q-BHQ-2 |
| RMRPO3H533P10 | 259 | ECGCCGGQGGCCCGGCGGP | H-Threo-HEX::P-Phosphate::Q-BHQ-2 |
| RMRPO3H533P11 | 260 | ECGCCGQGGGCCCGGCGP | H-Threo-HEX::P-Phosphate::Q-BHQ-2 |
| RMRPO3H533P12 | 261 | ECGCCGGQGGCCCGGCP | H-Threo-HEX::P-Phosphate::Q-BHQ-2 |
| RMRPO3H533P11 | 262 | ECCGGCGQCCGACAGTCGGP | H-Threo-HEX::P-Phosphate::Q-BHQ-2 |
| RMRPO3H533P8C | 263 | ECCGGCGQCCGACAGTCGP | H-Threo-HEX::P-Phosphate::Q-BHQ-2 |
| RMRPO3H533P13 | 264 | FCGCCGQGGGCCGGCCP | F-Threo-FAM::P-Phosphate::Q-BHQ-2 |
| RMRPO3H533P10C | 265 | FCGCCGGQGGCCCGGCGGP | F-Threo-FAM::P-Phosphate::Q-BHQ-2 |
| RMRPO3H533P1OE | 266 | FCGCCGQGGGCCCGGCGGP | F-Threo-FAM:P-Phosphate::Q-BHQ-2 |
| RMRPO3533P10C2 | 267 | FCGCCGGQGGCCCGGCP | F-Threo-FAM:P-Phosphate::Q-BHQ-2 |
| RMRPO3533P12B | 268 | FCGCCGQGGGCCCGGCP | F-Threo-FAM::P-Phosphate::Q-BHQ-2 |

TABLE I-continued

Probe for rpoB, inhA, and katG nucleic acid molecule targets

| | | | |
|---|---|---|---|
| RMRPO3533P12C | 269 | FCGCCQGGGGCCCGGCP | F-Threo-FAM::P-Phosphate::Q-BHQ-2 |
| RMRPO3533P12B2 | 270 | FCGCCGQGGGCCCGGCGCP | F-Threo-FAM::P-Phosphate::Q-BHQ-2 |
| RMRPO3533P12C2 | 271 | FCGCCQGGGGCCCGGCGGP | F-Threo-FAM::P-Phosphate::Q-BHQ-2 |
| RMRPO3533P12C3 | 272 | FCGCCQGAGGCCCGGCGGP | F-Threo-FAM::P-Phosphate::Q-BHQ-2 |
| RMRPO3533P12C4 | 273 | FAGCCQGGGGCCCGGCGGP | F-Threo-FAM::P-Phosphate::Q-BHQ-2 |
| RMRPO3533P13 | 274 | FCCGGGQGCCCGGCGGP | F-Threo-FAM::P-Phosphate::Q-BHQ-2 |
| RMRPO3533P14 | 275 | FCCGGGGQCCCGGCGGP | F-Threo-FAM::P-Phosphate::Q-BHQ-2 |
| RMRPO3H533P02B | 276 | ECCGGCGQCCGACAGTCP | H-Threo-HEX::P-Phosphate::Q-BHQ-2 |

| rpoB 511P | SEQ ID NO: | CTG/CCG | Leu/Pro |
|---|---|---|---|
| AYRPO3511PFM01 | 277 | FCAGCQCGAGCCAATTCATGP | F-Threo-FAM::P-Phosphate::Q-BHQ-2 |
| AYRPO3511PFM02 | 278 | FCAGCCQGAGCCAATTCATGP | F-Threo-FAM::P-Phosphate::Q-BHQ-2 |
| AYRPO3511PFM03 | 279 | FCAGCQJGAGCCAATTCATGP | F-Threo-FAM::P-Phosphate::Q-BHQ-2::J-G-Clamp |
| AYRPO3511PFM04 | 280 | FCAGCJGQAGCCAATTCATGP | F-Threo-FAM::P-Phosphate::Q-BHQ-2::J-G-Clamp |
| AYRPO3511PFM05 | 281 | FCAGCCGQAGCCAATTCATGP | F-Threo-FAM::P-Phosphate::Q-BHQ-2 |

| rpoB 526R | SEQ ID NO: | CAC/CGC | His/Arg |
|---|---|---|---|
| AYRPO3526RFM01 | 282 | FCTTGCGQGGTCAACCCCGAP | F-Threo-FAM::P-Phosphate::Q-BHQ-2 |
| AYRPO3526RFM02 | 283 | FTGCGGGQTCAACCCCGAP | F-Threo-FAM::P-Phosphate::Q-BHQ-2 |
| AYRPO3526RFM03 | 284 | FTGCGGGTCQAACCCCGAP | F-Threo-FAM::P-Phosphate::Q-BHQ-2 |
| AYRPO3526RFM04 | 285 | FCTTGCGGGQTCAACCCCGAP | F-Threo-FAM::P-Phosphate::Q-BHQ-2 |
| AYRPO3526RFM05 | 286 | FCTTGJGQGGTCAACCCCGAP | F-Threo-FAM::P-Phosphate::Q-BHQ-2::J-G-Clamp |
| AYRPO3526RFM06 | 287 | FTGJGGGQTCAACCCCGAP | F-Threo-FAM::P-Phosphate::Q-BHQ-2::J-G-Clamp |
| AYRPO3526RFM07 | 288 | FTGJGGGTCQAACCCCGAP | F-Threo-FAM::P-Phosphate::Q-BHQ-2::J-G-Clamp |
| AYRPO3526RFM08 | 289 | FCTTGJGGGQTCAACCCCGAP | F-Threo-FAM::P-Phosphate::Q-BHQ-2::J-G-Clamp |

| katG 315I Oligo Name | SEQ ID NO: | AGC/ATC Sequence | Modifications |
|---|---|---|---|
| AYKAT315ICM01 | 290 | FGATCACCATCGGCATCGAQ | F-Threo-Coum343::Q-BHQ-2 |
| AYKAT315ICM02 | 291 | FCACCATQCGGCATCGAGGTCP | F-Threo-Coum343::P-Phosphate::Q-BHQ-2 |
| AYKAT315ICM03 | 292 | FCATCGGQCATCGAGGTCGTAP | F-Threo-Coum343::P-Phosphate::Q-BHQ-2 |
| AYKAT315ICM04 | 293 | FCACCATQCGGCATCGAGGTCGTAP | F-Threo-Coum343::P-Phosphate::Q-BHQ-2 |
| AYKAT315ICM05 | 294 | FATCGGCQATCGAGGTCGTAP | F-Threo-Coum343::P-Phosphate::Q-BHQ-2 |
| AYKAT315ICM06 | 295 | FAUCGGCQAUCGAGGUCGUAP | F-Threo-Coum343::P-Phosphate::Q-BHQ-2::U-5-Propynyl dU |
| AYKAT315ICM07 | 296 | FAULGGLQAULGAGGULGUAP | F-Threo-Coum343::P-Phosphate::Q-BHQ-2::U-5-Propynyl dU::L-5-Propynyl dC |
| AYKAT315ICM03a | 297 | FCATCGQGCATCGAGGTCGTAP | F-Threo-Coum343::P-Phosphate::Q-BHQ-2 |

TABLE I-continued

Probe for rpoB, inhA, and katG nucleic acid molecule targets

| Oligo Name | SEQ ID NO: | Sequence | Modifications |
|---|---|---|---|
| AYKAT315ICM03b | 298 | FCATCGGCAYTCGAGGTCGTAP | F-Threo-Coum343::P-Phosphate::Q-BHQ-2 |
| AYKAT315ICM03c | 299 | FCATCGGCATCQGAGGTCGTAP | F-Threo-Coum343::P-Phosphate::Q-BHQ-2 |
| AYKAT315ICM03d | 300 | FCATCGGCQATCGAGGTCGTAP | F-Threo-Coum343::P-Phosphate::Q-BHQ-2 |
| AYKAT315ICY03a1 | 301 | FCATCGQGCATCGAGGTCGTAP | F-CY5.5::P-Phosphate::Q-BHQ-2 |
| AYKAT315ICY03a2 | 302 | FCATCGGCAYTCGAGGTCGTAP | F-CY5.5::P-Phosphate::Q-BHQ-2 |
| AYKAT315ICY03a3 | 303 | FCATCGGCATCQGAGGTCGTAP | F-CY5.5::P-Phosphate::Q-BHQ-2 |
| AYKAT315ICY03a4 | 304 | FCATCGGCATCGAQGGTCGTAP | F-CY5.5::P-Phosphate::Q-BHQ-2 |

| katG 315N Oligo Name | SEQ ID NO: | AGC/AAC Sequence | Modifications |
|---|---|---|---|
| AYKAT315NCM01 | 305 | FCAACGQGCATCGAGGTCGTAP | F-Threo-Coum343::P-Phosphate::Q-BHQ-2 |
| AYKAT315NCM02 | 306 | FCAACGGCAQTCGAGGTCGTAP | F-Threo-Coum343::P-Phosphate::Q-BHQ-2 |
| AYKAT315NCM03 | 307 | FCAACGGCATCQGAGGTCGTAP | F-Threo-Coum343::P-Phosphate::Q-BHQ-2 |
| AYKAT315NCM04 | 308 | FCAACGGQCATCGAGGTCGTAP | F-Threo-Coum343::P-Phosphate::Q-BHQ-2 |
| AYKAT315NCM05 | 309 | FCAACGGCQATCGAGGTCGTAP | F-Threo-Coum343::P-Phosphate::Q-BHQ-2 |
| AYKAT315NCM04a | 310 | FCAACGGQCATCGAGGTCGTAP | F-Threo-Coum343::P-Phosphate::Q-BHQ-2 |
| AYKAT315NCM05a | 311 | FCAACGGCQATCGAGGTCGTAP | F-Threo-Coum343::P-Phosphate::Q-BHQ-2 |
| AYKAT315NCM07 | 312 | FCAALGQGCATLGAGGTLGTAP | F-Threo-Coum343::P-Phosphate::Q-BHQ-2::L-5_Me_dC |
| AYKAT315NCM08 | 313 | FAACGGCQATCGAGGTCGTAP | F-Threo-Coum343::P-Phosphate::Q-BHQ-2 |
| AYKAT315NCM09 | 314 | FCACCAAQCGGCATCGAGGTCP | F-Threo-Coum343::P-Phosphate::Q-BHQ-2 |
| AYKAT315NCM10 | 315 | FCACCAAQCGGCATCGAGGTCGTAP | F-Threo-Coum343::P-Phosphate::Q-BHQ-2 |
| AYKAT315NCM11 | 316 | FLAALGQGLATLGAGGTLGTAP | F-Threo-Coum343::P-Phosphate::Q-BHQ-2 |
| AYKAT315NCM12 | 317 | FAALGGLQATLGAGGTLGTAP | F-Threo-Coum343::P-Phosphate::Q-BHQ-2::L-5_Me_dC |
| AYKAT315NCM13 | 318 | FLALLAAQLGGLATLGAGGTLP | F-Threo-Coum343::P-Phosphate::Q-BHQ-2::L-5_Me_dC |
| AYKAT315NCM14 | 319 | FLALLAAQLGGLATLGAGGTLGTAP | F-Threo-Coum343::P-Phosphate::Q-BHQ-2:1-5_Me_dC |
| AYKAT315NCM15 | 320 | FLAALGQGLATLGAGGTLGTAP | F-Threo-Coum343::P-Phosphate::Q-BHQ-2::L-5-Propynyl dC |
| AYKAT315NCM16 | 321 | FAALGGLQATLGAGGTLGTAP | F-Threo-Coum343::P-Phosphate::Q-BHQ-2::L-5-Propynyl dC |
| AYKAT315NCM17 | 322 | FLALLAAQLGGLATLGAGGTLP | F-Threo-Coum343::P-Phosphate::Q-BHQ-2::L-5-Propynyl dC |
| AYKAT315NCM18 | 323 | FLALLAAQLGGLATLGAGGTLGTAP | F-Threo-Coum343::P-Phosphate::Q-BHQ-2::L-5-Propynyl dC |
| AYKAT315NCM19 | 324 | FCAACQGGCATCGAGGTCGTAP | F-Threo-Coum343::P-Phosphate::Q-BHQ-2 |
| AYKAT315NCM20 | 325 | FCCAACGQGCATCGAGGTCGTAP | F-Threo-Coum343::P-Phosphate::Q-BHQ-2 |
| AYKAT315NCM21 | 326 | FCCAACQGGCATCGAGGTCGTAP | F-Threo-Coum343::P-Phosphate::Q-BHQ-2 |
| AYKAT315NCM22 | 327 | FACCAACQGGCATCGAGGTCGTAP | F-Threo-Coum343::P-Phosphate::Q-BHQ-2 |
| AYKAT315NCM23 | 328 | FACCAAQCGGCATCGAGGTCGTAP | F-Threo-Coum343::P-Phosphate::Q-BHQ-2 |

TABLE I-continued

Probe for rpoB, inhA, and katG nucleic acid molecule targets

| katG 315T Oligo Name | SEQ ID NO: | AGC/ACC Sequence | Modifications |
|---|---|---|---|
| AYKAT315TCM01 | 329 | FCACCACQCGGCATCGAGGTCP | F-Threo-Coum343::P-Phosphate::Q-BHQ-2 |
| AYKAT315TCM02 | 330 | FCACCAJQCGGCATCGAGGTCP | F-Threo-Coum343::P-Phosphate::Q-BHQ-2::J-G-Clamp |
| AYKAT315TCM03 | 331 | FCAJCGGQCATCGAGGTCGTAP | F-Threo-Coum343::P-Phosphate::Q-BHQ-2::J-G-Clamp |
| AYKAT315TCM04 | 332 | FCAJCGGQCATCGAGGTCP | F-Threo-Coum343::P-Phosphate::Q-BHQ-2::J-G-Clamp |
| AYKAT315TCM05 | 333 | FCACCAJQCGGCATCGAP | F-Threo-Coum343::P-Phosphate::Q-BHQ-2::J-G-Clamp |
| AYKAT315TCM05a | 334 | FCACCAQJCGGCATCGAP | F-Threo-Coum343::P-Phosphate::Q-BHQ-2::J-G-Clamp |
| AYKAT315TCM05b | 335 | FCACCAJCGQGCATCGAP | F-Threo-Coum343::P-Phosphate::Q-BHQ-2::J-G-Clamp |
| AYKAT315TCM05c | 336 | FCACCAJCGGCQATCGAP | F-Threo-Coum343::P-Phosphate::Q-BHQ-2::J-G-Clamp |
| AYKAT315TCY05b1 | 337 | FCACCAJCGQGCATCGAP | F-CY5.5::P-Phosphate::Q-BHQ-2::J-G-Clamp |
| AYKAT315TCY05b2 | 338 | FCACCAJCGGCQATCGAP | F-CY5.5::P-Phosphate::Q-BHQ-2::J-G-Clamp |
| AYKAT315TCY05b3 | 339 | FCACCAJCGGCATQCGAP | F-CY5.5::P-Phosphate::Q-BHQ-2::J-G-Clamp |
| AYKAT315TCY05b4 | 340 | FCACCAJCGGCATCGAQ | F-CY5.5::Q-BHQ-2::J-G-Clamp |

| katG 315T2 Oligo Name | SEQ ID NO: | AGC/ACA Sequence | Modifications |
|---|---|---|---|
| AYKAT315T2CM01 | 341 | FCACCAQJAGGCATCGAP | F-Threo-Coum343::P-Phosphate::Q-BHQ-2::J-G-Clamp |
| AYKAT315T2CM02 | 342 | FCACCAJAGQGCATCGAP | F-Threo-Coum343::P-Phosphate::Q-BHQ-2::J-G-Clamp |
| AYKAT315T2CM03 | 343 | FCACCAJAGGCQATCGAP | F-Threo-Coum343::P-Phosphate::Q-BHQ-2::J-G-Clamp |

| inhA Probe Designs inhA-15T Oligo Name | SEQ ID NO: | C -> T Sequence | Modifications |
|---|---|---|---|
| AYINHA15TCM01 | 344 | FGCGAGAQTGATAGGTTGTCGGP | F-Threo-Coum343::P-Phosphate::Q-BHQ-2 |
| AYINHA15TCM02 | 345 | FGAGATGQATAGGTTGTCGGGGTGAP | F-Threo-Coum343::P-Phosphate::Q-BHQ-2 |
| AYINHA15TCM03 | 346 | FGLGAGAQUGAUAGGUUGULGGP | F-Threo-Coum343::P-Phosphate::Q-BHQ-2::L-5-Propynyl dC::U-5-Propynyl dU |
| AYINHA15TCM04 | 347 | FAGATGAQTAGGTTGTCGGGGTGAP | F-Threo-Coum343::P-Phosphate::Q-BHQ-2 |
| AYINHA15TCM05 | 348 | FAGAUGAQUAGGUUGULGGGGUGAP | F-Threo-Coum343::P-Phosphate::Q-BHQ-2:1-5-Propynyl dC::U-5-Propynyl dU |
| AYINHA15TCM06 | 349 | FGATGATQAGGTTGTCGGGGTGAP | F-Threo-Coum343::P-Phosphate::Q-BHQ-2 |
| AYINHA15TCM04a | 350 | FAGATGATAQGGTTGTCGGGGTGAP | F-Threo-Coum343::P-Phosphate::Q-BHQ-2 |
| AYINHA15TCM04b | 351 | FAGATGATAGGQTTGTCGGGGTGAP | F-Threo-Coum343::P-Phosphate::Q-BHQ-2 |
| AYINHA15TCM04c | 352 | FAGATQGATAGGTTGTCGGGGTGAP | F-Threo-Coum343::P-Phosphate::Q-BHQ-2 |

TABLE I-continued

Probe for rpoB, inhA, and katG nucleic acid molecule targets

| | | | |
|---|---|---|---|
| AYINHA15TCM04d | 353 | FAGATQGATAGGTTGTCGGGGTGAP | F-Threo-Coum343::P-Phosphate::Q-BHQ-2 |
| AYINHA15TCM07 | 354 | FAGAUGAQUAGGUUGUCGGGGUGAP | F-Threo-Coum343::P-Phosphate::Q-BHQ-2::U-5-Propynyl dU |
| AYINHA15TCM08 | 355 | FGAUGAQUAGGUUGUCGGGGUGAP | F-Threo-Coum343::P-Phosphate::Q-BHQ-2::U-5-Propynyl dU |
| AYINHA15TCM09 | 356 | FAUGAQUAGGUUGUCGGGGUGAP | F-Threo-Coum343::P-Phosphate::Q-BHQ-2::U-5-Propynyl dU |
| AYINHA15TCM09a | 357 | FAUGAUQAGGUUGUCGGGGUGAP | F-Threo-Coum343::P-Phosphate::Q-BHQ-2::U-5-Propynyl dU |
| AYINHA15TCM09b | 358 | FATGAUQAGGUUGUCGGGGUGAP | F-Threo-Coum343::P-Phosphate::Q-BHQ-2::U-5-Propynyl dU |
| AYINHA15TCM06a | 359 | FGAUGAUQAGGUUGUCGGGGUGAP | F-Threo-Coum343::P-Phosphate::Q-BHQ-2::U-5-Propynyl dU |
| AYINHA15TCM06b | 360 | FGATGAQUAGGUUGUCGGGGUGAP | F-Threo-Coum343::P-Phosphate::Q-BHQ-2::U-5-Propynyl dU |
| JFINHA15TCM06A_1 | 361 | FGAUGAUQAGGUUGUCGJGGUGAP | F-Threo-Coum343::P-Phosphate::Q-BHQ-2::U-5-Propynyl dU::J-7_Dz_dG |
| JFINHA15TCM06A_2 | 362 | FGAUGAUQAGGUUGUCGGJGUGAP | F-Threo-Coum343::P-Phosphate::Q-BHQ-2::U-5-Propynyl dU::J-7_Dz_dG |
| JFINHA15TCM06B_1 | 363 | FGATGAQUAGGUUGUCGJGGUGAP | F-Threo-Coum343::P-Phosphate::Q-BHQ-2::U-5-Propynyl dU::J-7_Dz_dG |
| JFINHA15TCM06B_2 | 364 | FGATGAQUAGGUUGUCGGJGUGAP | F-Threo-Coum343::P-Phosphate::Q-BHQ-2::U-5-Propynyl dU::J-7_Dz_dG |
| JFYINHA15TCM09A_1 | 365 | FAUGAUQAGGUUGUCGJGGUGAP | F-Threo-Coum343::P-Phosphate::Q-BHQ-2::U-5-Propynyl dU::J-7_Dz_dG |
| JFINHA15TCM09A_1 | 366 | FAUGAUQAGGUUGUCGGJGUGAP | F-Threo-Coum343::P-Phosphate::Q-BHQ-2::U-5-Propynyl dU::J-7_Dz_dG |
| JFINHA15TCM09B_1 | 367 | FATGAUQAGGUUGUCGJGGUGAP | F-Threo-Coum343::P-Phosphate::Q-BHQ-2::U-5-Propynyl dU::J-7_Dz_dG |
| JFINHA15TCM09B_2 | 368 | FATGAUQAGGUUGUCGGJGUGAP | F-Threo-Coum343::P-Phosphate::Q-BHQ-2::U-5-Propynyl dU::J-7_Dz_dG |
| AYINHAR15TCM01 | 369 | FCTATCAQTCTCGCCGCGGCP | F-Threo-Coum343::P-Phosphate::Q-BHQ-2 |
| AYINHAR15TCM02 | 370 | FCTATCAQTCTCGCCGCGGCCP | F-Threo-Coum343::P-Phosphate::Q-BHQ-2 |
| AYINHAR15TCM03 | 371 | FCTATCAQTCTCGCCGCGGCCGP | F-Threo-Coum343::P-Phosphate::Q-BHQ-2 |
| AYINHAR15TCM04 | 372 | FTATCATQCTCGCCGCGGCCP | F-Threo-Coum343::P-Phosphate::Q-BHQ-2 |

| inhA-8A Oligo Name | SEQ ID NO: | T -> A Sequence | Modifications |
|---|---|---|---|
| AYINHA8ACM01 | 373 | FTAGGATQGTCGGGGTGACTGCCAP | F-Threo-Coum343::P-Phosphate::Q-BHQ-2 |
| AYINHA8ACM02 | 374 | FTAGGATQGTCGGGGTGACTGCP | F-Threo-Coum343::P-Phosphate::Q-BHQ-2 |
| AYINHA8ACM03 | 375 | FGATAGGQATGTCGGGGTGACTGCP | F-Threo-Coum343::P-Phosphate::Q-BHQ-2 |
| AYINHA8ACM04 | 376 | FUAGGAUQGULGGGGUGALUP | F-Threo-Coum343::P-Phosphate::Q-BHQ-2::U-5-Propynyl dU |
| AYINHA8ACM05 | 377 | FTAGGAQTGTCGGGGTGACTGCCAP | F-Threo-Coum343::P-Phosphate::Q-BHQ-2 |

TABLE I-continued

Probe for rpoB, inhA, and katG nucleic acid molecule targets

| Oligo Name | SEQ ID NO: | Sequence | Modifications |
|---|---|---|---|
| AYINHA8ACM06 | 378 | FTAGGATGTQCGGGGTGACTGCCAP | F-Threo-Coum343::P-Phosphate::Q-BHQ-2 |
| AYINHA8ACM07 | 379 | FTAGGATGTCGQGGGTGACTGCCAP | F-Threo-Coum343::P-Phosphate::Q-BHQ-2 |
| AYINHA8ACM08 | 380 | FTAGGQATGTCGGGGTGACTGCCAP | F-Threo-Coum343::P-Phosphate::Q-BHQ-2 |
| AYINHA8ACM08a | 381 | FUAGGQAUGUCGGGGUGACUGCCAP | F-Threo-Coum343::P-Phosphate::Q-BHQ-2::U-5-Propynyl dU |
| AYINHA8ACM08b | 382 | FUAGGQAUGULGGGGUGALUGLLAP | F-Threo-Coum343::P-Phosphate::Q-BHQ-2::U-5-Propynyl dU |
| AYINHAR8ACM01 | 383 | FCGACATQCCTATCGTCTCGCCGCP | F-Threo-Coum343::P-Phosphate::Q-BHQ-2 |
| AYINHAR8ACM02 | 384 | FGACATCQCTATCGTCTCGCCGCP | F-Threo-Coum343::P-Phosphate::Q-BHQ-2 |
| AYINHAR8ACM03 | 385 | FACATCCQTATCGTCTCGCCGCP | F-Threo-Coum343::P-Phosphate::Q-BHQ-2 |
| AYINHAR8ACM04 | 386 | FCATCCTQATCGTCTCGCCGCP | F-Threo-Coum343::P-Phosphate::Q-BHQ-2 |
| AYINHAR8ACM05 | 387 | FCGACATQCCTATCGTCTCGCCP | F-Threo-Coum343::P-Phosphate::Q-BHQ-2 |
| AYINHAR8ACM02a | 388 | FGACATCQCTATCGTCTCGCCGCP | F-Threo-Coum343::P-Phosphate::Q-BHQ-2 |
| AYINHAR8ACM02b | 389 | FGACATCCQTATCGTCTCGCCGCP | F-Threo-Coum343::P-Phosphate::Q-BHQ-2 |
| AYINHAR8ACM02c | 390 | FGACATCCTAQTCGTCTCGCCGCP | F-Threo-Coum343::P-Phosphate::Q-BHQ-2 |
| AYINHAR8ACM02d | 391 | FGACATQCCTATCGTCTCGCCGCP | F-Threo-Coum343::P-Phosphate::Q-BHQ-2 |
| AYINHAR8ACM02e | 392 | FGACATCQCUAUCGUCUCGCCGCP | F-Threo-Coum343::P-Phosphate::Q-BHQ-2::U-5-Propynyl dU |
| AYINHAR8ACM02f | 393 | FGACATCCQUAUCGUCUCGCCGCP | F-Threo-Coum343::P-Phosphate::Q-BHQ-2::U-5-Propynyl dU |
| AYINHAR8ACM02g | 394 | FGACATCCUAQUCGUCUCGCCGCP | F-Threo-Coum343::P-Phosphate::Q-BHQ-2::U-5-Propynyl dU |
| AYINHAR8ACM02h | 395 | FGACATQCCUAUCGUCUCGCCGCP | F-Threo-Coum343::P-Phosphate::Q-BHQ-2::U-5-Propynyl dU |
| JFINHA8ACM08A_1 | 396 | FUAGGQAUGUCGJGGUGACUGCCAP | F-Threo-Coum343::P-Phosphate::Q-BHQ-2::U-5-Propynyl dU::J-7_Dz_dG |
| JFINHA8ACM08A_2 | 397 | FUAGGQAUGUCGGJGUGACUGCCAP | F-Threo-Coum343::P-Phosphate::Q-BHQ-2::U-5-Propynyl dU::J-7_Dz_dG |
| JFINHA8ACM08B_1 | 398 | FUAGGQAUGULGJGGUGALUGLLAP | F-Threo-Coum343::P-Phosphate::Q-BHQ-2::U-5-Propynyl dU::J-7_Dz_dG:I-5_Me_dC |
| JFINHA8ACM08B_2 | 399 | FUAGGQAUGULGGJGUGALUGLLAP | F-Threo-Coum343::P-Phosphate::Q-BHQ-2::U-5-Propynyl dU::J-7_Dz_dG:I-5_Me_dC |

| inhA-8C Oligo Name | SEQ ID NO: | T -> C Sequence | Modifications |
|---|---|---|---|
| AYINHA8ACM01 | 400 | FTAGGCTQGTCGGGGTGACTGCP | F-Threo-Coum343::P-Phosphate::Q-BHQ-2 |
| AYINHA8ACM02 | 401 | FTAGGJTQGTCGGGGTGACTGCP | F-Threo-Coum343::P-Phosphate::Q-BHQ-2::J-G-Clamp |
| AYINHA8ACM03 | 402 | FGATAGGQJTGTCGGGGTGACTGCP | F-Threo-Coum343::P-Phosphate::Q-BHQ-2::J-G-Clamp |
| AYINHA8ACM04 | 403 | FATAGGJQTGTCGGGGTGACTGCP | F-Threo-Coum343::P-Phosphate::Q-BHQ-2::J-G-Clamp |
| AYINHA8ACM05 | 404 | FAGGJTGQTCGGGGTGACTGCP | F-Threo-Coum343::P-Phosphate::Q-BHQ-2::J-G-Clamp |
| AYINHAR8CCM01 | 405 | FCGACAGQCCTATCGTCTCGCCGCP | F-Threo-Coum343::P-Phosphate::Q-BHQ-2 |

TABLE I-continued

Probe for rpoB, inhA, and katG nucleic acid molecule targets

| | | | |
|---|---|---|---|
| AYINHAR8CCM02 | 406 | FGACAGCQCTATCGTCTCGCCGCP | F-Threo-Coum343::P-Phosphate::Q-BHQ-2 |
| AYINHAR8CCM03 | 407 | FACAGCCQTATCGTCTCGCCGCP | F-Threo-Coum343::P-Phosphate::Q-BHQ-2 |
| AYINHAR8CCM04 | 408 | FCAGCCTQATCGTCTCGCCGCP | F-Threo-Coum343::P-Phosphate::Q-BHQ-2 |
| AYINHAR8CCM05 | 409 | FCGACAGQCCTATCGTCTCGCCP | F-Threo-Coum343::P-Phosphate::Q-BHQ-2 |

In one embodiment, the above described a plurality of sets of rpoB, inhA, and katG primers and probes are used in order to provide for detection of MTB-RIF and/or MTB-INH in a biological sample suspected of containing MTB-RIF and/or MTB-INH. The sets of primers and probes may comprise or consist of the primers and probes specific for the rpoB, inhA, and katG nucleic acid sequences, comprising or consisting of the nucleic acid sequences of SEQ ID NOs: 1 through 409. In another embodiment, the primers and probes for the rpoB, inhA, and katG targets comprise or consist of a functionally active variant of any of the primers of SEQ ID NOs: 1 through 409.

A functionally active variant of any of the probes of SEQ ID NOs: 1 through 409 may be identified by using the probes in the disclosed method. A functionally active variant of a probe of any of the SEQ ID NOs: 1 through 409 pertains to a primer which provides a similar or higher specificity and sensitivity in the method or kit described herein as compared to the respective sequence of SEQ ID NOs: 1 through 409.

The variant may, e.g., vary from the sequence of SEQ ID NOs: 1 through 409 by one or more nucleotide additions, deletions or substitutions such as one or more nucleotide additions, deletions or substitutions at the 5' end and/or the 3' end of the respective sequence of SEQ ID NOs: 1 through 409. As detailed above, a primer (and/or probe) may be chemically modified, i.e., a primer and/or probe may comprise a modified nucleotide or a non-nucleotide compound. A probe (or a primer) is then a modified oligonucleotide. "Modified nucleotides" (or "nucleotide analogs") differ from a natural "nucleotide" by some modification but still consist of a base or base-like compound, a pentofuranosyl sugar or a pentofuranosyl sugar-like compound, a phosphate portion or phosphate-like portion, or combinations thereof. For example, a "label" may be attached to the base portion of a "nucleotide" whereby a "modified nucleotide" is obtained. A natural base in a "nucleotide" may also be replaced by, e.g., a 7-desazapurine whereby a "modified nucleotide" is obtained as well. The terms "modified nucleotide" or "nucleotide analog" are used interchangeably in the present application. A "modified nucleoside" (or "nucleoside analog") differs from a natural nucleoside by some modification in the manner as outlined above for a "modified nucleotide" (or a "nucleotide analog").

Oligonucleotides including modified oligonucleotides and oligonucleotide analogs that amplify a nucleic acid molecule encoding the rpoB, inhA, and katG nucleic acid sequences, e.g., nucleic acids encoding alternative portions of rpoB, inhA, and katG can be designed using, for example, a computer program such as OLIGO (Molecular Biology Insights Inc., Cascade, Colo.). Important features when designing oligonucleotides to be used as amplification primers include, but are not limited to, an appropriate size amplification product to facilitate detection (e.g., by electrophoresis), similar melting temperatures for the members of a pair of primers, and the length of each primer (i.e., the primers need to be long enough to anneal with sequence-specificity and to initiate synthesis but not so long that fidelity is reduced during oligonucleotide synthesis). Typically, oligonucleotide primers are 8 to 50 nucleotides in length (e.g., 8, 10, 12, 14, 16, 18, 20, 22, 24, 26, 28, 30, 32, 34, 36, 38, 40, 42, 44, 46, 48, or 50 nucleotides in length).

In addition to a set of primers, the disclosed methods may use one or more probes in order to detect the presence or absence of MTB-RIF and/or MTB-INH. The term "probe" refers to synthetically or biologically produced nucleic acids (DNA or RNA), which by design or selection, contain specific nucleotide sequences that allow them to hybridize under defined predetermined stringencies specifically (i.e., preferentially) to "target nucleic acids", in the present case to a MTB-RIF and/or MTB-INH (target) nucleic acid. A "probe" can be referred to as a "detection probe" meaning that it detects the target nucleic acid.

In some embodiments, the described rpoB, inhA, and katG probes can be labeled with at least one fluorescent label. In one embodiment, the rpoB, inhA, and katG probes can be labeled with a donor fluorescent moiety, e.g., a fluorescent dye, and a corresponding acceptor fluorescent moiety, e.g., a quencher.

In one embodiment, the probes comprise or consist of a fluorescent moiety and the nucleic acid sequences comprise or consist of SEQ ID NOs: 1 through 409.

Designing oligonucleotides to be used as hybridization probes can be performed in a manner similar to the design of primers. Embodiments may use a single probe or a pair of probes for detection of the amplification product. Depending on the embodiment, the probe(s) use may comprise at least one label and/or at least one quencher moiety. As with the primers, the probes usually have similar melting temperatures, and the length of each probe must be sufficient for sequence-specific hybridization to occur but not so long that fidelity is reduced during synthesis. Oligonucleotide probes are generally 15 to 30 (e.g., 16, 18, 20, 21, 22, 23, 24, or 25) nucleotides in length.

Polymerase Chain Reaction (PCR)

U.S. Pat. Nos. 4,683,202, 4,683,195, 4,800,159, and 4,965,188 disclose conventional PCR techniques. PCR typically employs two oligonucleotide primers that bind to a selected nucleic acid template (e.g., DNA or RNA). Primers useful in some embodiments include oligonucleotides capable of acting as points of initiation of nucleic acid synthesis within the described rpoB, inhA, and katG nucleic acid sequences. A primer can be purified from a restriction digest by conventional methods, or it can be produced synthetically. The primer is preferably single-stranded for maximum efficiency in amplification, but the primer can be double-stranded. Double-stranded primers are first denatured, i.e., treated to separate the strands. One method of denaturing double stranded nucleic acids is by heating.

If the template nucleic acid is double-stranded, it is necessary to separate the two strands before it can be used as a template in PCR. Strand separation can be accomplished by any suitable denaturing method including physical, chemical or enzymatic means. One method of separating the nucleic acid strands involves heating the nucleic acid until it is predominately denatured (e.g., greater than 50%, 60%, 70%, 80%, 90% or 95% denatured). The heating conditions necessary for denaturing template nucleic acid will depend, e.g., on the buffer salt concentration and the length and nucleotide composition of the nucleic acids being denatured, but typically range from about 90° C. to about 105° C. for a time depending on features of the reaction such as temperature and the nucleic acid length. Denaturation is typically performed for about 30 sec to 4 min (e.g., 1 min to 2 min 30 sec, or 1.5 min).

If the double-stranded template nucleic acid is denatured by heat, the reaction mixture is allowed to cool to a temperature that promotes annealing of each primer to its target sequence on the described rpoB, inhA, and katG nucleic acid molecules. The temperature for annealing is usually from about 35° C. to about 65° C. (e.g., about 40° C. to about 60° C.; about 45° C. to about 50° C.). Annealing times can be from about 10 sec to about 1 min (e.g., about 20 sec to about 50 sec; about 30 sec to about 40 sec). The reaction mixture is then adjusted to a temperature at which the activity of the polymerase is promoted or optimized, i.e., a temperature sufficient for extension to occur from the annealed primer to generate products complementary to the template nucleic acid. The temperature should be sufficient to synthesize an extension product from each primer that is annealed to a nucleic acid template, but should not be so high as to denature an extension product from its complementary template (e.g., the temperature for extension generally ranges from about 40° C. to about 80° C. (e.g., about 50° C. to about 70° C.; about 60° C.). Extension times can be from about 10 sec to about 5 min (e.g., about 30 sec to about 4 min; about 1 min to about 3 min; about 1 min 30 sec to about 2 min).

PCR assays can employ MTB-RIF and/or MTB-INH nucleic acid such as RNA or DNA (cDNA). The template nucleic acid need not be purified; it may be a minor fraction of a complex mixture, such as MTB-RIF and/or MTB-INH nucleic acid contained in human cells. MTB-RIF and/or MTB-INH nucleic acid molecules may be extracted from a biological sample by routine techniques such as those described in *Diagnostic Molecular Microbiology: Principles and Applications* (Persing et al. (eds), 1993, American Society for Microbiology, Washington D.C.). Nucleic acids can be obtained from any number of sources, such as plasmids, or natural sources including bacteria, yeast, viruses, organelles, or higher organisms such as plants or animals.

The oligonucleotide primers are combined with PCR reagents under reaction conditions that induce primer extension. For example, chain extension reactions generally include 50 mM KCl, 10 mM Tris-HCl (pH 8.3), 15 mM $MgCl_2$, 0.001% (w/v) gelatin, 0.5-1.0 µg denatured template DNA, 50 pmoles of each oligonucleotide primer, 2.5 U of Taq polymerase, and 10% DMSO). The reactions usually contain 150 to 320 µM each of dATP, dCTP, dTTP, dGTP, or one or more analogs thereof.

The newly synthesized strands form a double-stranded molecule that can be used in the succeeding steps of the reaction. The steps of strand separation, annealing, and elongation can be repeated as often as needed to produce the desired quantity of amplification products corresponding to the target MTB-RIF and/or MTB-INH nucleic acid molecules. The limiting factors in the reaction are the amounts of primers, thermostable enzyme, and nucleoside triphosphates present in the reaction. The cycling steps (i.e., denaturation, annealing, and extension) are preferably repeated at least once. For use in detection, the number of cycling steps will depend, e.g., on the nature of the sample. If the sample is a complex mixture of nucleic acids, more cycling steps will be required to amplify the target sequence sufficient for detection. Generally, the cycling steps are repeated at least about 20 times, but may be repeated as many as 40, 60, or even 100 times.

Fluorescence Resonance Energy Transfer (FRET)

FRET technology (see, for example, U.S. Pat. Nos. 4,996,143, 5,565,322, 5,849,489, and 6,162,603) is based on a concept that when a donor fluorescent moiety and a corresponding acceptor fluorescent moiety are positioned within a certain distance of each other, energy transfer takes place between the two fluorescent moieties that can be visualized or otherwise detected and/or quantitated. The donor typically transfers the energy to the acceptor when the donor is excited by light radiation with a suitable wavelength. The acceptor typically re-emits the transferred energy in the form of light radiation with a different wavelength.

In one example, a oligonucleotide probe can contain a donor fluorescent moiety and a corresponding quencher, which may or not be fluorescent, and which dissipates the transferred energy in a form other than light. When the probe is intact, energy transfer typically occurs between the two fluorescent moieties such that fluorescent emission from the donor fluorescent moiety is quenched. During an extension step of a polymerase chain reaction, a probe bound to an amplification product is cleaved by the 5' to 3' nuclease activity of, e.g., a Taq Polymerase such that the fluorescent emission of the donor fluorescent moiety is no longer quenched. Exemplary probes for this purpose are described in, e.g., U.S. Pat. Nos. 5,210,015, 5,994,056, and 6,171,785. Commonly used donor-acceptor pairs include the FAM-TAMRA pair. Commonly used quenchers are DABCYL and TAMRA. Commonly used dark quenchers include Black-Hole Quenchers™ (BHQ), (Biosearch Technologies, Inc., Novato, Calif.), Iowa Black™, (Integrated DNA Tech., Inc., Coralville, Iowa), BlackBerry™ Quencher 650 (BBQ-650), (Berry & Assoc., Dexter, Mich.).

In another example, two oligonucleotide probes, each containing a fluorescent moiety, can hybridize to an amplification product at particular positions determined by the complementarity of the oligonucleotide probes to the MTB-RIF and/or MTB-INH target nucleic acid sequence. Upon hybridization of the oligonucleotide probes to the amplification product nucleic acid at the appropriate positions, a FRET signal is generated. Hybridization temperatures can range from about 35° C. to about 65° C. for about 10 sec to about 1 min.

Fluorescent analysis can be carried out using, for example, a photon counting epifluorescent microscope system (containing the appropriate dichroic mirror and filters for monitoring fluorescent emission at the particular range), a photon counting photomultiplier system, or a fluorometer. Excitation to initiate energy transfer can be carried out with an argon ion laser, a high intensity mercury (Hg) arc lamp, a fiber optic light source, or other high intensity light source appropriately filtered for excitation in the desired range.

As used herein with respect to donor and corresponding acceptor fluorescent moieties "corresponding" refers to an acceptor fluorescent moiety having an emission spectrum that overlaps the excitation spectrum of the donor fluorescent moiety. The wavelength maximum of the emission spectrum of the acceptor fluorescent moiety should be at least 100 nm greater than the wavelength maximum of the excitation spectrum of the donor fluorescent moiety. Accordingly, efficient non-radiative energy transfer can be produced therebetween.

Fluorescent donor and corresponding acceptor moieties are generally chosen for (a) high efficiency Forster energy transfer; (b) a large final Stokes shift (>100 nm); (c) shift of the emission as far as possible into the red portion of the visible spectrum (>600 nm); and (d) shift of the emission to a higher wavelength than the Raman water fluorescent emission produced by excitation at the donor excitation wavelength. For example, a donor fluorescent moiety can be chosen that has its excitation maximum near a laser line (for example, Helium-Cadmium 442 nm or Argon 488 nm), a high extinction coefficient, a high quantum yield, and a good overlap of its fluorescent emission with the excitation spectrum of the corresponding acceptor fluorescent moiety. A corresponding acceptor fluorescent moiety can be chosen that has a high extinction coefficient, a high quantum yield, a good overlap of its excitation with the emission of the donor fluorescent moiety, and emission in the red part of the visible spectrum (>600 nm).

Representative donor fluorescent moieties that can be used with various acceptor fluorescent moieties in FRET technology include fluorescein, *Lucifer* Yellow, B-phycoerythrin, 9-acridineisothiocyanate, *Lucifer* Yellow VS, 4-acetamido-4'-isothio-cyanatostilbene-2,2'-disulfonic acid, 7-diethylamino-3-(4'-isothiocyanatophenyl)-4-methylcoumarin, succinimdyl 1-pyrenebutyrate, and 4-acetamido-4'-isothiocyanatostilbene-2,2'-disulfonic acid derivatives. Representative acceptor fluorescent moieties, depending upon the donor fluorescent moiety used, include LC Red 640, LC Red 705, Cy5, Cy5.5, Lissamine rhodamine B sulfonyl chloride, tetramethyl rhodamine isothiocyanate, rhodamine x isothiocyanate, erythrosine isothiocyanate, fluorescein, diethylenetriamine pentaacetate, or other chelates of Lanthanide ions (e.g., Europium, or Terbium). Donor and acceptor fluorescent moieties can be obtained, for example, from Molecular Probes (Junction City, Oreg.) or Sigma Chemical Co. (St. Louis, Mo.).

The donor and acceptor fluorescent moieties can be attached to the appropriate probe oligonucleotide via a linker arm. The length of each linker arm is important, as the linker arms will affect the distance between the donor and acceptor fluorescent moieties. The length of a linker arm is the distance in Angstroms (Å) from the nucleotide base to the fluorescent moiety. In general, a linker arm is from about 10 Å to about 25 Å. The linker arm may be of the kind described in WO 84/03285. WO 84/03285 also discloses methods for attaching linker arms to a particular nucleotide base, and also for attaching fluorescent moieties to a linker arm.

An acceptor fluorescent moiety, such as an LC Red 640, can be combined with an oligonucleotide which contains an amino linker (e.g., C6-amino phosphoramidites available from ABI (Foster City, Calif.) or Glen Research (Sterling, Va.)) to produce, for example, LC Red 640-labeled oligonucleotide. Frequently used linkers to couple a donor fluorescent moiety such as fluorescein to an oligonucleotide include thiourea linkers (FITC-derived, for example, fluorescein-CPG's from Glen Research or ChemGene (Ashland, Mass.)), amide-linkers (fluorescein-NHS-ester-derived, such as CX-fluorescein-CPG from BioGenex (San Ramon, Calif.)), or 3'-amino-CPGs that require coupling of a fluorescein-NHS-ester after oligonucleotide synthesis.

Detection of MTB-RIF and/or MTB-INH

The present disclosure provides methods for detecting the presence or absence of MTB-RIF and/or MTB-INH in a biological or non-biological sample. Methods provided herein avoid problems of sample contamination, false negatives, and false positives. The methods include performing at least one cycling step that includes amplifying a portion of rpoB, inhA, and katG target nucleic acid molecules from a sample using a plurality of pairs of rpoB, inhA, and katG primers, and a FRET detecting step. Multiple cycling steps are performed, preferably in a thermocycler. Methods described herein can be performed using the rpoB, inhA, and katG primers and probes to detect the presence of rpoB, inhA, and katG targets, and the detection of the described SNPs in the rpoB, inhA, and katG targets indicates the presence of MTB-RIF and/or MTB-INH in the sample.

As described herein, amplification products can be detected using labeled hybridization probes that take advantage of FRET technology. One FRET format utilizes TaqMan® technology to detect the presence or absence of an amplification product, and hence, the presence or absence of the target nucleic acid. TaqMan® technology utilizes one single-stranded hybridization probe labeled with, e.g., one fluorescent dye and one quencher, which may or may not be fluorescent. When a first fluorescent moiety is excited with light of a suitable wavelength, the absorbed energy is transferred to a second fluorescent moiety according to the principles of FRET. The second fluorescent moiety is generally a quencher molecule. During the annealing step of the PCR reaction, the labeled hybridization probe binds to the target DNA (i.e., the amplification product) and is degraded by the 5' to 3' nuclease activity of, e.g., the Taq Polymerase during the subsequent elongation phase. As a result, the fluorescent moiety and the quencher moiety become spatially separated from one another. As a consequence, upon excitation of the first fluorescent moiety in the absence of the quencher, the fluorescence emission from the first fluorescent moiety can be detected. By way of example, an ABI PRISM® 7700 Sequence Detection System (Applied Biosystems) uses TaqMan® technology, and is suitable for performing the methods described herein for detecting the presence or absence of the target nucleic acid in the sample.

Generally, the presence of FRET indicates the presence of MTB-RIF and/or MTB-INH in the sample, and the absence of FRET indicates the absence of MTB-RIF and/or MTB-INH in the sample. Inadequate specimen collection, transportation delays, inappropriate transportation conditions, or use of certain collection swabs (calcium alginate or aluminum shaft) are all conditions that can affect the success and/or accuracy of a test result, however. Using the methods disclosed herein, detection of FRET within, e.g., 45 cycling steps is indicative of an MTB-RIF and/or MTB-INH infection.

Representative biological samples that can be used include, but are not limited to dermal swabs, nasal swabs, wound swabs, blood cultures, skin, and soft tissue infections. Collection and storage methods of biological samples are known to those of skill in the art. Biological samples can be processed (e.g., by nucleic acid extraction methods and/or kits known in the art) to release MTB-RIF and/or MTB-INH nucleic acid or in some cases, the biological sample can be contacted directly with the PCR reaction components and the appropriate oligonucleotides.

Within each thermocycler run, control samples can be cycled as well. Positive control samples can amplify target nucleic acid control template (other than described amplification products of target genes) using, for example, control primers and control probes. Positive control samples can also amplify, for example, a plasmid construct containing the target nucleic acid molecules. Such a plasmid control can be amplified internally (e.g., within the sample) or in a separate sample run side-by-side with the patients' samples using the same primers and probe as used for detection of the intended target. Such controls are indicators of the success or failure of the amplification, hybridization, and/or FRET reaction. Each thermocycler run can also include a negative control that, for example, lacks target template DNA. Negative control can measure contamination. This ensures that the system and reagents would not give rise to a false positive signal. Therefore, control reactions can readily determine, for example, the ability of primers to anneal with sequence-specificity and to initiate elongation, as well as the ability of probes to hybridize with sequence-specificity and for FRET to occur.

In an embodiment, the methods include steps to avoid contamination. For example, an enzymatic method utilizing uracil-DNA glycosylase is described in U.S. Pat. Nos. 5,035,996, 5,683,896 and 5,945,313 to reduce or eliminate contamination between one thermocycler run and the next.

Conventional PCR methods in conjunction with FRET technology can be used. In one embodiment, a LightCycler® instrument is used. The following patent applications describe real-time PCR as used in the LightCycler® technology: WO 97/46707, WO 97/46714, and WO 97/46712.

The LightCycler® can be operated using a PC workstation and can utilize a Windows NT operating system. Signals from the samples are obtained as the machine positions the capillaries sequentially over the optical unit. The software can display the fluorescence signals in real-time immediately after each measurement. Fluorescent acquisition time is 10-100 milliseconds (msec). After each cycling step, a quantitative display of fluorescence vs. cycle number can be continually updated for all samples. The data generated can be stored for further analysis.

It is understood that the embodiments described herein are not limited by the configuration of one or more commercially available instruments.

Articles of Manufacture/Kits

Embodiments of the present disclosure further provide for articles of manufacture or kits to detect MTB-RIF and/or MTB-INH. An article of manufacture can include primers and probes used to detect rpoB, inhA, and katG, together with suitable packaging materials. Representative primers and probes for detection of MTB-RIF and/or MTB-INH are capable of hybridizing to rpoB, inhA, and katG target nucleic acid molecules. In addition, the kits may also include suitably packaged reagents and materials needed for DNA immobilization, hybridization, and detection, such solid supports, buffers, enzymes, and DNA standards. Methods of designing primers and probes are disclosed herein, and representative examples of primers and probes that amplify and hybridize to rpoB, inhA, and katG target nucleic acid molecules are provided.

Articles of manufacture can also include one or more fluorescent moieties for labeling the probes or, alternatively, the probes supplied with the kit can be labeled. For example, an article of manufacture may include a donor and/or an acceptor fluorescent moiety for labeling the rpoB, inhA, and katG probes. Examples of suitable FRET donor fluorescent moieties and corresponding acceptor fluorescent moieties are provided above.

Articles of manufacture can also contain a package insert or package label having instructions thereon for using the rpoB, inhA, and katG primers and probes to detect MTB-RIF and/or MTB-INH in a sample. Articles of manufacture may additionally include reagents for carrying out the methods disclosed herein (e.g., buffers, polymerase enzymes, co-factors, or agents to prevent contamination). Such reagents may be specific for one of the commercially available instruments described herein.

Embodiments of the present disclosure will be further described in the following examples, which do not limit the scope of the invention described in the claims.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed:

1. A kit for detecting nucleic acids encoding *Mycobacterium tuberculosis* (MTB) resistant to rifampicin (MTB-RIF) and MTB resistant to isoniazid (MTB-INH), comprising:
   a) a plurality of sets of rpoB, inhA, and katG primers for amplification of rpoB, inhA, and katG gene targets; and
   b) a plurality of fluorescently labeled probes for detecting all of the following SNPs: rpoB 531L, rpoB 531W, rpoB 526L, rpoB 526Y, rpoB 526D, rpoB 526N, rpoB 513L, rpoB 513K, rpoB 513P, rpoB 522L, rpoB 522Q, rpoB 522W, rpoB 516V, rpoB 516Y, rpoB 533P, rpoB 511P, rpoB 526R, inhA-15T, inhA-8A, inhA-8C, katG 315I, katG 315N, katG 315T, and katG 315T2, wherein the plurality of probes comprises:
      (i) at least 17 probes for detecting the 17 rpoB SNPs and wherein the probes are selected from the group consisting of SEQ ID NOS 1-289 or a complement thereof,
      (ii) at least 3 inhA probes for detecting the inhA SNPs and wherein the probes are selected from the group consisting of SEQ ID NO: 344-409 or a complement thereof, and
      (iii) at least 4 katG probes for detecting the katG SNPs and wherein the probes are selected from the group consisting of SEQ ID NOS: 290-343 or a complement thereof.

2. The kit of claim 1, wherein the at least 17 probes for detecting the 17 rpoB SNPs are selected from the group consisting of SEQ ID NOs: 52, 55, 58, 84, 99, 102, 108, 121, 142, 155, 162, 180, 196, 199, 238, 240, 280, and 286, or a complement thereof; the at least 3 inhA probes for detecting the inhA SNPs are SEQ ID NOs: 363, 384, and 407, or a complement thereof; and the at least 4 katG probes for detecting the katG SNPs are SEQ ID NOs: 297, 305, 335, and 341, or a complement thereof.

3. The kit of claim 1, wherein each probe of said plurality of fluorescently labeled rpoB, inhA, and katG probes comprises a donor fluorescent moiety and a corresponding acceptor fluorescent moiety.

4. The kit of claim 3, wherein the acceptor fluorescent moiety is a quencher.

5. The kit of claim 1, further comprising nucleoside triphosphates, nucleic acid polymerase, and buffers necessary for the function of the nucleic acid polymerase.

* * * * *